(12) United States Patent
Knowlton

(10) Patent No.: US 7,442,192 B2
(45) Date of Patent: Oct. 28, 2008

(54) METHOD AND APPARATUS FOR SURGICAL DISSECTION

(76) Inventor: Edward W. Knowlton, 5478 Blackhawk Dr., Danville, CA (US) 94526

( * ) Notice: Subject to any disclaimer, the term of this patent is extended or adjusted under 35 U.S.C. 154(b) by 186 days.

(21) Appl. No.: 10/620,311

(22) Filed: Jul. 14, 2003

(65) Prior Publication Data

US 2004/0049251 A1 Mar. 11, 2004

Related U.S. Application Data

(60) Provisional application No. 60/418,089, filed on Oct. 13, 2002, provisional application No. 60/416,206, filed on Oct. 3, 2002, provisional application No. 60/396,038, filed on Jul. 14, 2002.

(51) Int. Cl.
*A61B 18/18* (2006.01)
(52) U.S. Cl. .............. 606/45; 606/41; 607/101
(58) Field of Classification Search .............. 606/41, 606/45, 48–50, 190; 607/101
See application file for complete search history.

(56) References Cited

U.S. PATENT DOCUMENTS

| 5,919,219 | A | 7/1999 | Knowlton |
| 6,241,753 | B1 | 6/2001 | Knowlton |
| 6,311,090 | B1 | 10/2001 | Knowlton |
| 6,350,276 | B1 | 2/2002 | Knowlton |
| 6,377,854 | B1 | 4/2002 | Knowlton |
| 6,896,674 | B1 * | 5/2005 | Woloszko et al. ............. 606/41 |

FOREIGN PATENT DOCUMENTS

WO WO 02/053048 7/2002

\* cited by examiner

*Primary Examiner*—Michael Peffley
(74) *Attorney, Agent, or Firm*—Paul Davis; Heller Ehrman LLP

(57) ABSTRACT

An apparatus for dissecting tissue in a substantially uniform plane of dissection includes a housing configured to be advanced under a tissue layer, and control one of a depth of dissection or tissue flap thickness. The housing thermally shields at least a portion of the tissue flap. A roller is coupled to the housing. The roller is configured to smoothly advance housing over tissue. An energy delivery device is coupled to housing. The energy delivery device is configured to be coupled to an energy source. The energy delivery device has a geometry that substantially defines a plane of dissection.

4 Claims, 46 Drawing Sheets

$T_1$-$E_1$ ASPECT RATIO ≅ 1MM TO 2.5 CM $E_2$-$T_2$ ASPECT RATIO ≅ 0MM TO 1.5 CM $E_1$-$B_1$ ASPECT RATIO ≅ 0MM TO 1.5 CM $E_2$-$B_2$ ASPECT RATIO ≅ 0MM TO 1.5 CM

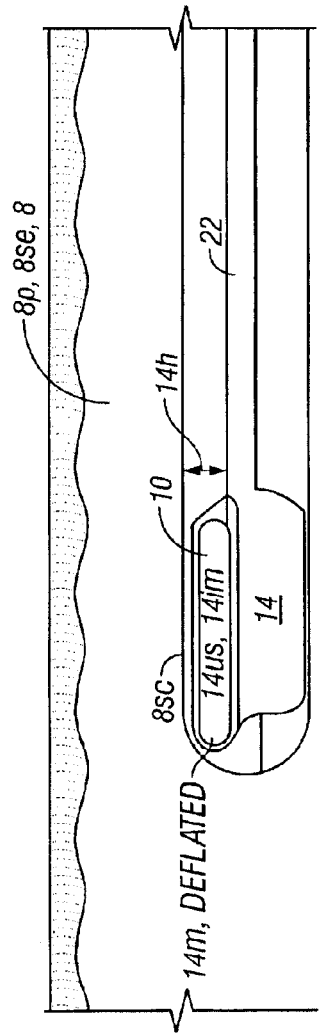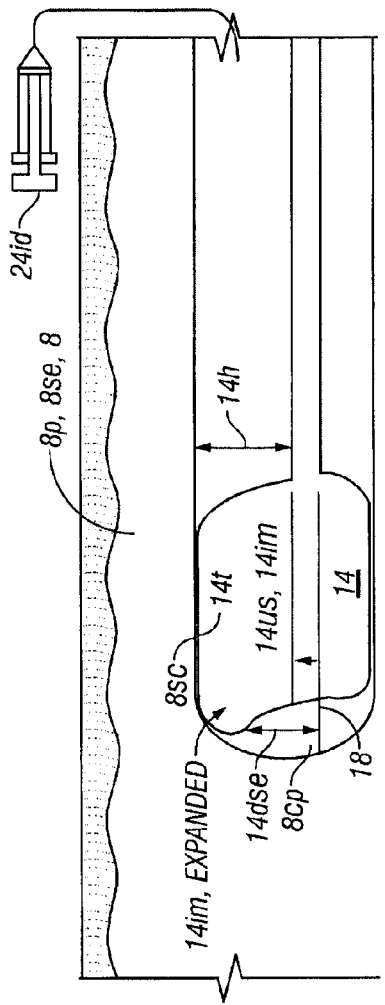
FIG. 20A
FIG. 20B

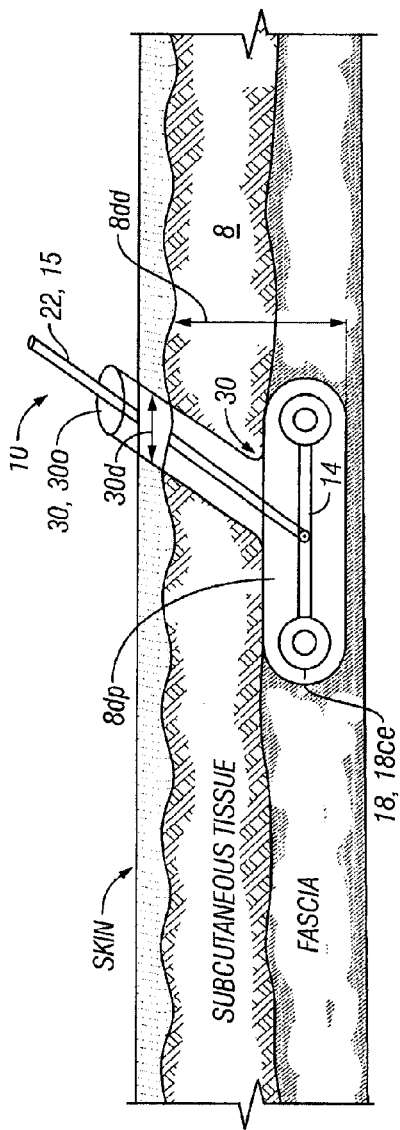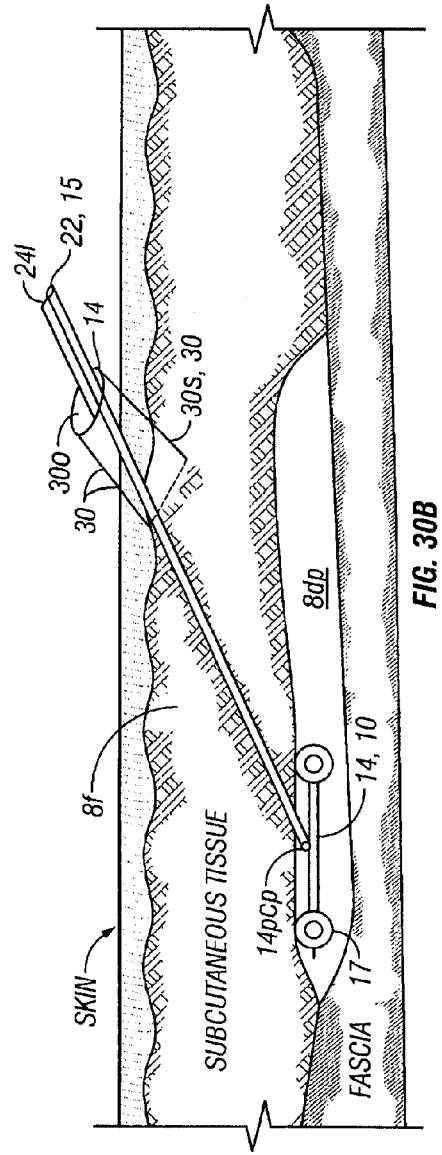
FIG. 30A
FIG. 30B

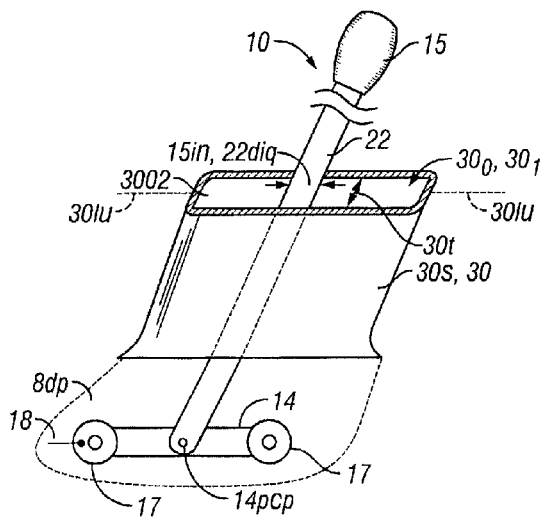
FIG. 30C
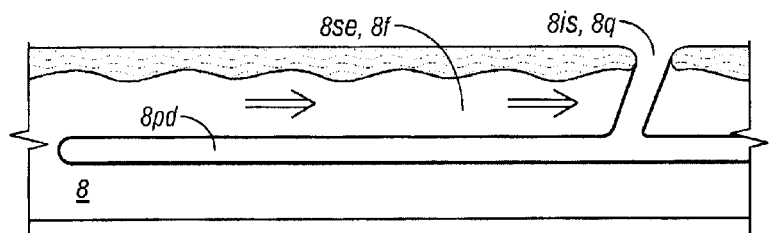
FIG. 31A
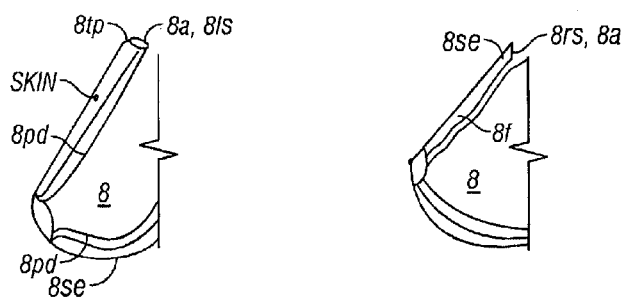
FIG. 31B  FIG. 31C

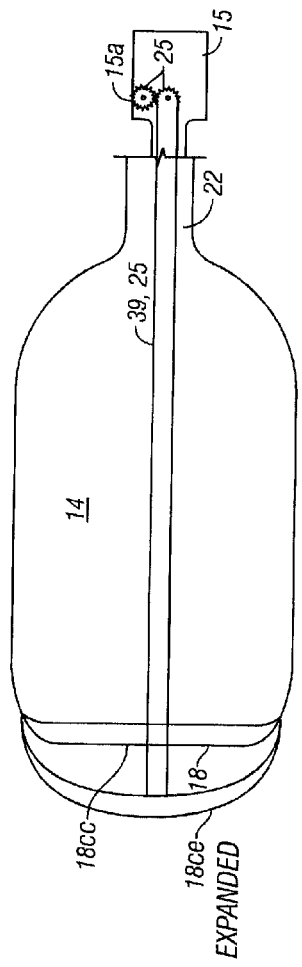
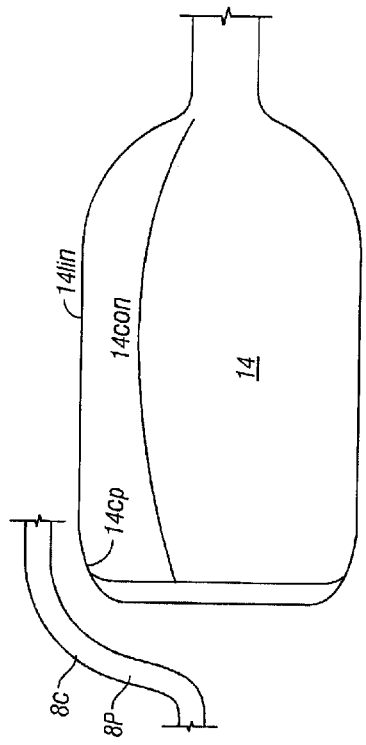
FIG. 35
FIG. 36A

METHOD AND APPARATUS FOR SURGICAL DISSECTION

CROSS-REFERENCE TO RELATED APPLICATIONS

This application claims the benefit of U.S. Ser. No. 60/396,038, filed Jul. 14, 2002, U.S. Ser. No. 60/416,206, filed Oct. 3, 2002, and U.S. Ser. No. 60/418,089, filed Oct. 13, 2002, all of which applications are fully incorporated herein by reference.

BACKGROUND OF THE INVENTION

FIELD OF THE INVENTION

This invention relates to a method and apparatus for treating tissue. More particularly, the invention relates to a method for treating tissue using the delivery of energy. Still more particularly the invention relates to a method and apparatus for treating tissue using the delivery of energy to perform electro-surgical procedures.

The human skin is composed of two elements: the epidermis and the underlying dermis. The epidermis with the stratum corneum serves as a biological barrier to the environment. In the basilar layer of the epidermis, pigment-forming cells called melanocytes are present. They are the main determinants of skin color. The dermis is composed mainly of an extra-cellular protein called collagen.

There are many causes of skin irregularities and deformities including skin laxity, sun damage etc. These irregularities are the result of changes in the structure and properties of the skin and underlying tissue layers. One of the more prominent causes of surface irregularities is cellulite which results in a dimpled, lumpy, or bulging skin surface. Cellulite appears in the subcutaneous level of skin tissue, that is the level below the dermis. Fat cells in the subcutaneous layer are arranged in chambers surrounded by connective tissue called septae. As fat cells increase in size to the deposition of intracellular of fat, the fibrous septae, which encase fat loculations and which connect the deep aspect of the dermis to the subjacent muscle fascia, are placed under increasing tension.

The growth in size of the fat loculations and the increase in tension of the fibrous septae are combined with a progressive laxity of skin due to age. This multifactorial complex of increasing tension of the fibrous septae, increasing size of fat loculations and progressive age related skin laxity results in a three dimensional dimpling of the skin. This results in areas of the skin being held down while other sections bulge outward, resulting in the lumpy, 'cottage-cheese' appearance.

As described above, the dermis is composed mainly of an extracellular protein called collagen. Collagen is produced by fibroblasts and synthesized as a triple helix with three polypeptide chains that are connected with heat labile and heat stable chemical bonds. When collagen-containing tissue is heated, alterations in the physical properties of this protein matrix occur at a characteristic temperature. The structural transition of collagen contraction occurs at a specific "shrinkage" temperature. The shrinkage and remodeling of the collagen matrix with heat is the basis for the technology.

Collagen crosslinks are either intramolecular (covalent or hydrogen bond) or intermolecular (covalent or ionic bonds). The thermal cleavage of intramolecular hydrogen crosslinks is a scalar process that is created by the balance between cleavage events and relaxation events (reforming of hydrogen bonds). No external force is required for this process to occur. As a result, intermolecular stress is created by the thermal cleavage of intramolecular hydrogen bonds. Essentially, the contraction of the tertiary structure of the molecule creates the initial intermolecular vector of contraction.

Collagen fibrils in a matrix exhibit a variety of spatial orientations. The matrix is lengthened if the sum of all vectors acts to distract the fibril. Contraction of the matrix is facilitated if the sum of all extrinsic vectors acts to shorten the fibril. Thermal disruption of intramolecular hydrogen bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming after lengthening or contraction of the fibril.

Hydrogen bond cleavage is a quantum mechanical event that requires a threshold of energy. The amount of (intramolecular) hydrogen bond cleavage required corresponds to the combined ionic and covalent intermolecular bond strengths within the collagen fibril. Until this threshold is reached, little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and non-polar regions in the lengthened or contracted fibril.

Cleavage of collagen bonds also occurs at lower temperatures but at a lower frequency. Low level thermal cleavage is frequently associated with relaxation phenomena in which bonds are reformed without a net change in molecular length. An external force that mechanically cleaves the fibril can reduce the probability of relaxation phenomena and provides a means to lengthen or contract the collagen matrix at lower temperatures while reducing the potential of surface ablation.

Soft tissue remodeling is a biophysical phenomenon that occurs at cellular and molecular levels. Molecular contraction or partial denaturization of collagen involves the application of an energy source, which destabilizes the longitudinal axis of the molecule by cleaving the heat labile bonds of the triple helix. As a result, stress is created to break the intermolecular bonds of the matrix. This is essentially an immediate extracellular process, whereas cellular contraction can require a lag period for the migration and multiplication of fibroblasts into the wound as provided by the wound healing sequence. In higher developed animal species, the wound healing response to injury involves an initial inflammatory process that subsequently leads to the deposition of scar tissue.

The initial inflammatory response consists of the infiltration by white blood cells or leukocytes that dispose of cellular debris. Seventy-two hours later, proliferation of fibroblasts at the injured site occurs. These cells differentiate into contractile myofibroblasts, which are the source of cellular soft tissue contraction. Following cellular contraction, collagen is laid down as a static supporting matrix in the tightened soft tissue structure. The deposition and subsequent remodeling of this nascent scar matrix provides the means to alter the consistency and geometry of soft tissue for aesthetic purposes.

Dissection is the surgical separation of soft tissue components or the creation of a separation interface within a soft tissue component. The plane of dissection is the surgical plane of soft tissue where different or the same soft tissue components have been separated from or within each other. The plane of dissection implies a horizontal orientation along soft tissue components. Incise implies a vertical orientation of dissection through soft tissue components. The undermined area is the area in a plane of dissection that is separated from the subjacent soft tissue. Referring to FIGS. 1(a)-1(f), the cutaneous flap, shown in FIG. 1(a) is a composite isolate of skin and subcutaneous soft tissue that has been surgically separated along a horizontal plane of dissection from the subjacent soft tissue. The subdermal plexus is the superficial vascular supply of a cutaneous flap. Flap can also mean an isolate of skin and soft tissue that will be advanced or moved to an adjacent recipient site or used to close an adjacent soft tissue defect. A synonymous term is 'random cutaneous flap'.

The myocutaneous flap, shown in FIG. 1(b) is a thicker composite isolate of skin, subcutaneous soft tissue and muscle that has been surgically separated from surrounding soft tissue. The myocutaneous perforators (e.g. arteries) are the deeper and more robust vascular supply of a myocutaneous flap. Flap necrosis is a nonviable portion of a flap that has an inadequate vascular supply. Flap necrosis is more likely to occur in cutaneous flaps because of their less robust vascular supply. Other types of flaps will exhibit a less or more robust vascular supply.

The fasciocutaneous flap shown in FIG. 1(c) that consists of the skin, subcutaneous layer, and fascia is more robust in it's circulation than the cutaneous flap which consists of the skin and a viable thickness of subcutaneous layer. In comparison, the fasciosubcutaneous flap (shown in FIG. 1(d)) which consists of the variable amount in the deep portion of the subcutaneous layer with the subjacent fascia, is less robust than the fasciocutaneous flap but more robust than a subcutaneous flap (shown in FIG. 1(e)) that consists only of the subcutaneous layer. However the most robust flap is the myofascial flap (shown in FIG. 1(f)) with has an axial circulation that runs longitudinally through the length of the flap. Flaps may also be combination flaps (shown in FIG. 1(g)) where the proximal portion of the flap involves a deeper tissue component such as the muscle or fascia but which extend distally with more superficial components such as the subcutaneous layer and/or skin.

There are a number of surgical, reconstructive, cosmetic, dermatological procedures tissue where it is useful to dissect a selected tissue layer having a uniform thickness while minimizing injury to surrounding tissue. Such procedures include tissue reconstructions, mastectomy and breast reconstruction, mastopexy, face lifts, liposuction, buttocks lifts and the like. There is a need for instruments for such procedures. Further, there are also a number of surgical, cosmetic, dermatological procedures that lend themselves to treatments which in addition to surgical remodeling, thermal energy is delivered to the skin and underlying tissue to cause a contraction of collagen, and/or initiate a wound healing response so as to tighten or rejuvenate the skin and underlying tissue at the tissue site. Such procedures include tissue reconstructions, breast reconstruction, breast repositioning, liposuction, face lift skin remodeling, resurfacing, skin tightening, wrinkle removal and the like.

There is a need for an improved dissection, cutting device that dissects tissues at a controlled depth.

SUMMARY OF THE INVENTION

Accordingly, an object of the present invention is to provide an apparatus, and its methods of use, that delivers energy to a tissue site and dissect a tissue plane at a controlled depth.

Another object of the present invention is to provide an apparatus, and its methods of use, that delivers energy to a tissue site, dissect a tissue plane at a controlled depth, produces a tissue flap with a substantially uniform thickness while protecting or minimizing injury to tissue or structures within the flap Still another object of the present invention is to provide an apparatus, and its methods of use, that used RF energy to dissect tissue and create one or more tissue flaps with a substantial uniform thickness.

A further object of the present invention is to provide an apparatus, and its methods of use, that creates a uniform surgical release and mass shifting of overlying soft tissue structures from subjacent tissue structures by uniformly dissecting the overlying structures from the underlying tissue.

Yet another object of the present invention is to provide an apparatus, and its methods of use, that creates a uniform surgical release and a shifting of overlying soft tissue structures.

Another object of the present invention is to provide an apparatus, and its methods of use, that creates a means to surgically shift soft tissue through smaller less visible incisions.

These and other objects of the present invention are achieved in an apparatus, for dissecting tissue in a substantially uniform plane of dissection. A housing is configured to be advanced under a tissue layer and control one of a depth of dissection or tissue flap thickness. The housing thermally shields at least a portion of the tissue flap. A roller is coupled to the housing. The roller is configured to smoothly advance housing over tissue. An energy delivery device is coupled to housing. The energy delivery device is configured to be coupled to an energy source. The energy delivery device has a geometry that substantially defines a plane of dissection.

In another embodiment, an electro-surgical apparatus includes an electrode with a cutting edge. A housing is coupled to the electrode. The housing includes a top with a top proximal section and a bottom with a bottom proximal section. The top proximal section has a geometry that facilitates creation of a skin flap with a substantially uniform thickness that includes a skin layer and an adjacent layer of subcutaneous tissue. The bottom proximal section has a geometry that preserves a plane of tissue that is positioned adjacent to the adjacent layer of subcutaneous tissue.

In another embodiment, a dissection apparatus includes an energy delivery device with an energy delivery surface. A housing is coupled to the energy delivery device. The housing includes a guide configured to permit the energy delivery surface provide a surgical plane of dissection to free a skin section and an underlying thickness of subcutaneous tissue while preserving an adjacent plane of tissue.

In another embodiment, a tissue dissection apparatus includes an electrosurgical energy delivery device with an electrosurgical cutting edge. A housing is coupled to the energy delivery device. The housing includes a guard that guides and facilitates a dissection to create a surgical plane of dissection to free a skin section and an underlying thickness of subcutaneous tissue while preserving an adjacent plane of tissue.

In another embodiment, a method of creating a tissue effect provides an electro-surgical device that includes an energy delivery device with an energy delivery surface. A housing is coupled to the electrode with a guide that provides for cutting a skin layer and an underlying thickness of subcutaneous tissue while preserving an adjacent plane of tissue. The energy delivery surface is positioned at the skin surface. Sufficient energy is delivered from the energy delivery device to cut the skin surface and the underlying thickness of subcutaneous tissue at a selected depth while preserving the adjacent plane of tissue.

In another embodiment, a method of creating a tissue effect provides an electro-surgical device that includes an electrode with a cutting edge, a housing coupled to the electrode with a guide that provides for cutting a skin layer and an underlying thickness of subcutaneous tissue while preserving an adjacent plane of tissue. The cutting edge is positioned at the skin surface. The skin surface and a layer of an adjacent underlying tissue are cut. A tissue effect is created.

BRIEF DESCRIPTION OF THE FIGURES

FIGS. 14-18 illustrate an apparatus of the present invention for dissecting or cutting tissue that include trans-cutaneous markers.

FIG. 17 illustrates an apparatus of the present invention for dissecting or cutting tissue with different bump shapes.

FIG. 18 illustrates an apparatus of the present invention for dissecting or cutting tissue with marking ridges to provide a visual bracketing or cue of the width of the plane of dissection.

FIGS. 19(a) through 20b illustrate an apparatus of the present invention for dissecting or cutting tissue with a detachable section or movable or variable shaped contour.

FIG. 24 illustrate an apparatus of the present invention for dissecting or cutting tissue with apertures to direct or infuse a cooling solution onto the skin envelope or tissue flap.

FIG. 25 illustrate an apparatus of the present invention for dissecting or cutting tissue with a porous section coupled to the housing 14 and fluidically coupled to one or more lumens.

FIGS. 30(a) through 30(c) illustrate an apparatus of the present invention for dissecting or cutting tissue that include a port device.

FIGS. 31(a) through 31(c) illustrate an apparatus of the present invention for dissecting or cutting tissue configured to provide a uniform surgical release and mass shifting of overlying soft tissue structures from subjacent tissue structures by uniformly dissecting the overlying structures from the underlying tissue.

FIG. 35 illustrate an apparatus of the present invention for dissecting or cutting tissue with a housing configured to vary the amount that the electrode can be advanced or retracted in an out of the housing.

FIG. 37 illustrates an apparatus of the present invention for dissecting or cutting tissue with a plurality of conformable portions having different flexural moduli.

FIGS. 42 and 43 illustrate an apparatus of the present invention for dissecting or cutting tissue with rollers located above and below the electrode 18.

FIG. 44 illustrate an apparatus of the present invention for dissecting or cutting tissue with a roller that can generate sufficient frictional force with the contacting tissue so as to put all or a portion of the subjacent tissue layers in contact with the housing.

DETAILED DESCRIPTION OF THE PREFERRED EMBODIMENT

Figure 1A:
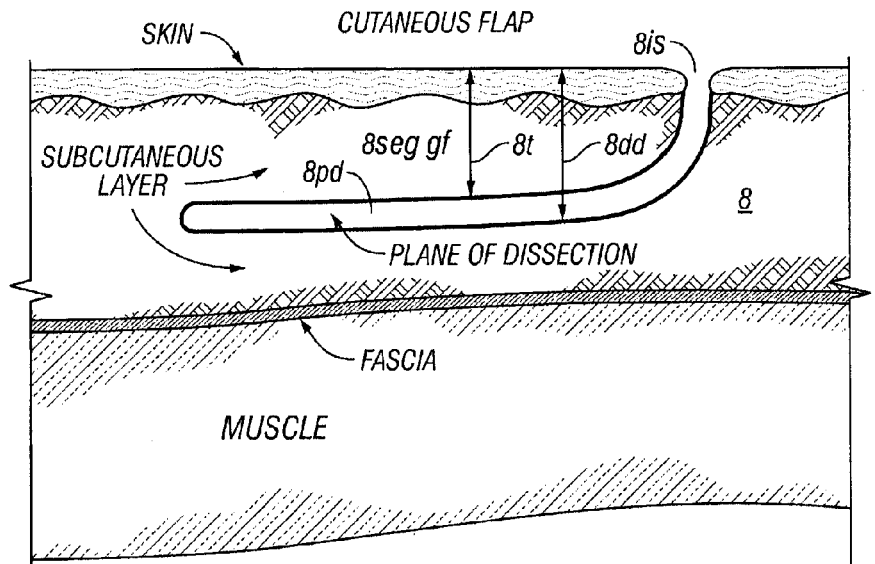
FIGS. 1(a) through 1(g) illustrated cross-sectional views of a skin surface, and various underlying structures.
Figure 1B:
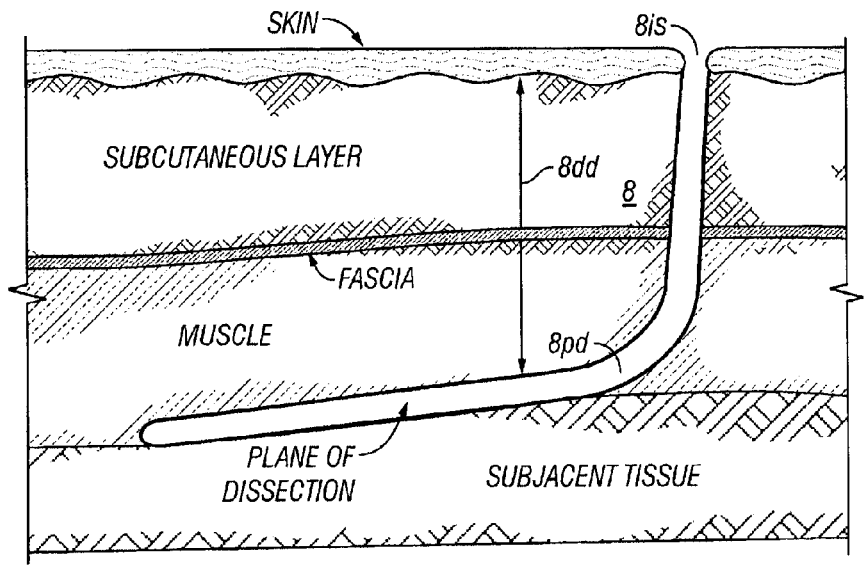
Figure 1C:
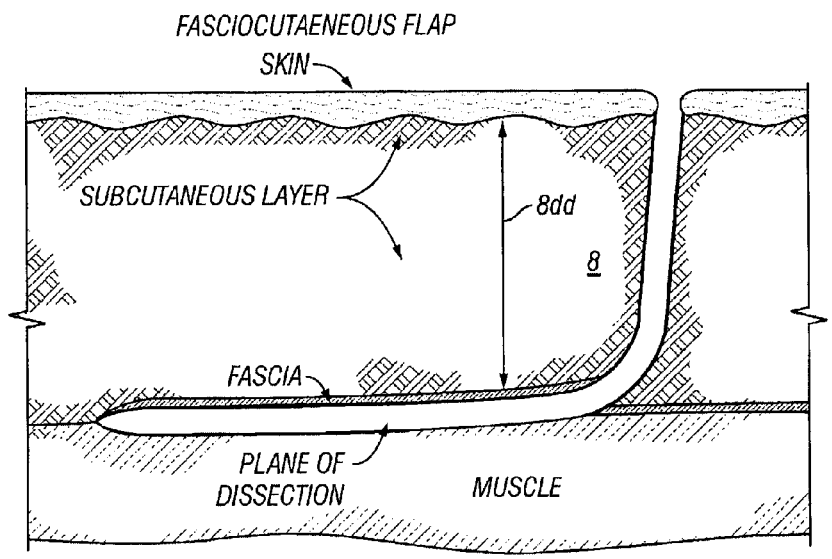
Figure 1D:
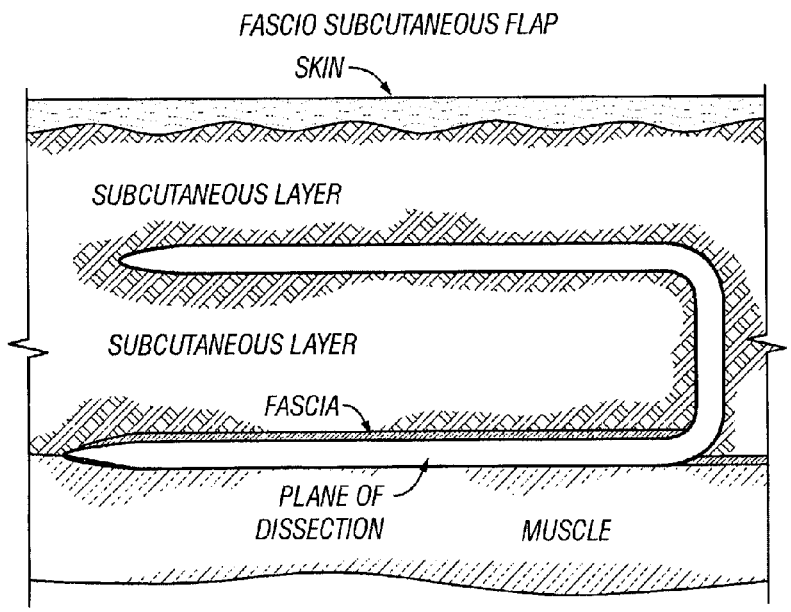
Figure 1E:
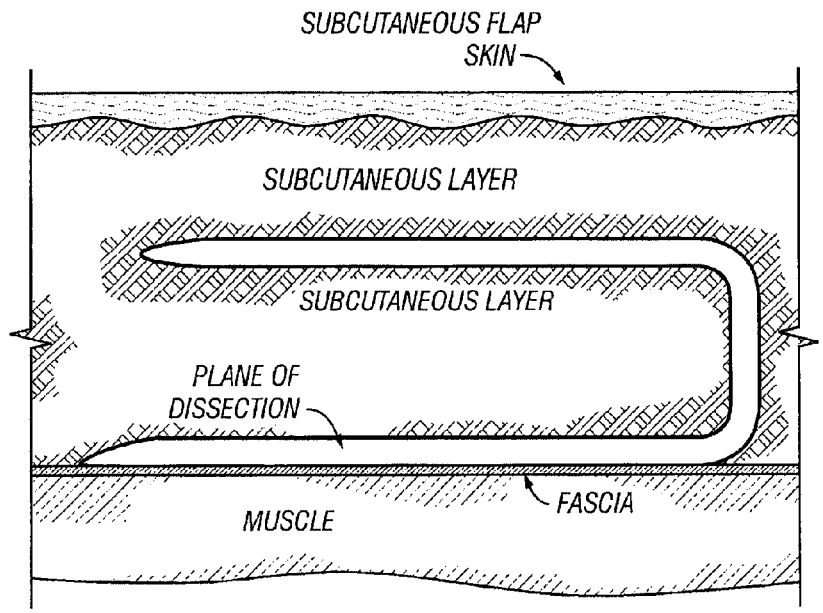
Figure 1F:
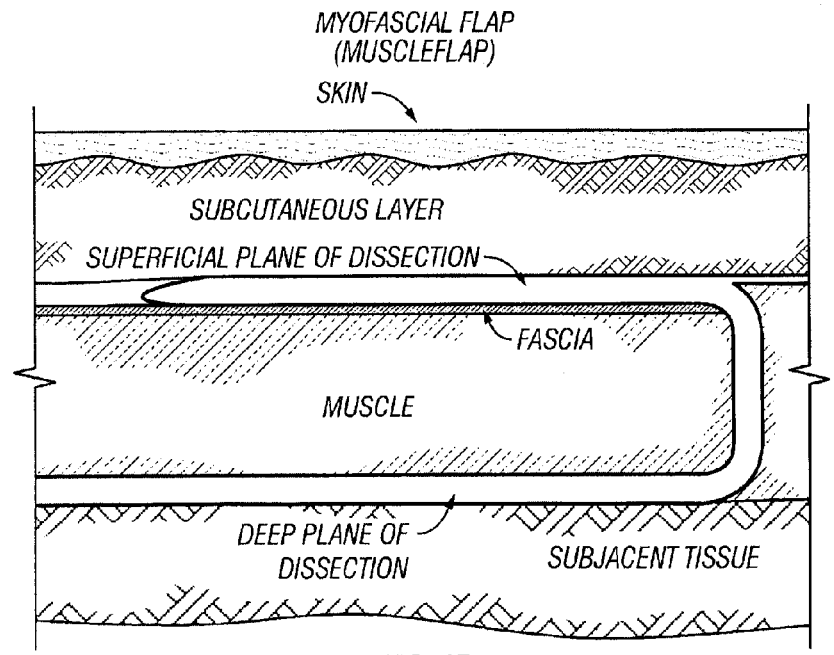
Figure 1G:
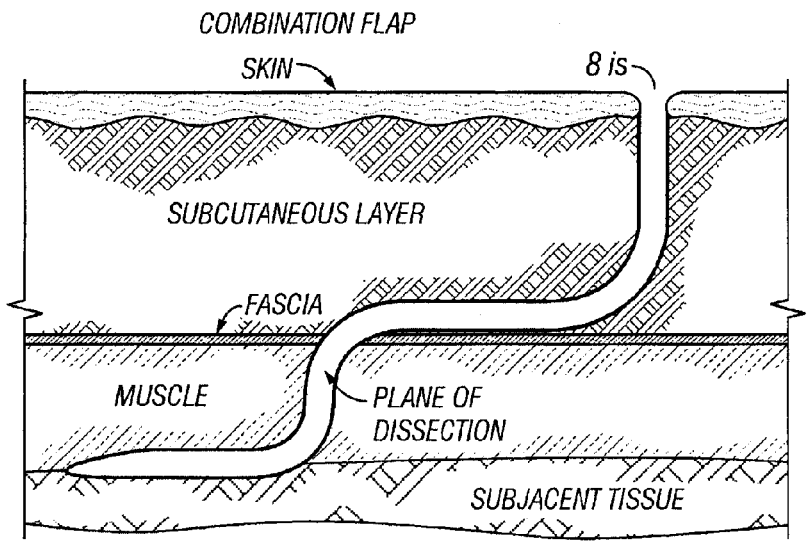

Embodiments of the invention provide a method and apparatus for use in various surgical procedures such as plastic surgery procedures and minimally invasive surgical procedures. In an embodiment, the apparatus can comprise an electro-surgical instrument configured to use radio-frequency (RF) or other electromagnetic energy to perform various surgical procedures including, but not limited to, cutting, dissection, coagulation and the like. In an embodiment, the apparatus can be configured to be used in surgical dissection procedures to produce one or more tissue flaps having a substantially uniform thickness.

Referring now to FIGS. 2(a) through 7, these figures illustrate embodiments of an apparatus 10 that can be configured to dissect tissue or treat tissue at a target tissue site 8 such as a subcutaneous tissue site and create a selected plane of dissection 8pd having a selectable and substantially uniform depth of dissection 8dd and a selectable and substantially uniform flap thickness 8t.

In various embodiments, apparatus 10 can create (i) a uniform plane of flap dissection, including but not limited to electrosurgical, a uniform flap thickness of or a uniform flap of variable thickness, (ii) a reduced surface area in a plane of dissection due to flap uniformity, (iii) a more uniform plane of wound healing with a reduction on volumetric scarring within the plane of dissection, uniform thermal tightening of the dissected skin flap, (iv) a uniform primary tightening, which is a thermal molecular collagen contraction within the plane of dissection, (v) a uniform secondary tightening: delayed secondary wound healing contraction within the plane of dissection, (vi) a reduction in iatrogenic surface contour irregularities of the flap surface, (vii) a uniform release of subjacent soft tissue structures, and the like.

Apparatus 10 can also be utilized to create secondary aesthetic guide effects including but not limited to, (i) 3 dimensional contour enhancement from flap advancement, (ii) 2 dimensional surface area tightening from primary and secondary thermal tightening of the skin flap, (iii) creation of a surgical portal for suction curettment of a liposuction treatment site that can provide a more uniform contour reduction than standard liposuction, (iv) provide a surgical portal for lifting plication of the subjacent soft tissue, (v) create a uniform release of pre-existing tethering fibrous septae which causes cellulite dimpling of the skin surface.

Apparatus 10 can have guard effects, relative to tissue dissection and/or cutting, that can be utilized for a variety of applications and result in, (i) a reduction of electrosurgical complications of flap dissection, (ii) a reduced incidence of full thickness flap lacerations (button holing), (iii) a reduced incidence of deep tissue injuries of the subjacent vital structures such as nerves, vessels and muscle either from transaction or thermal conductive damage, (iv) a reduced incidence of flap necrosis due to interruption of flap blood supply, (v) a reduced incidence of electrosurgical burns of the flap, and the like.

FIGS. 1 and 2(a) through 2(c) illustrate an embodiment of apparatus 10 that can include a housing 14 having proximal and distal portions 14p and 14d (here distal refers to the front of housing 14 that is advanced into tissue and proximal refers to the trailing end of housing 14). A hand piece 15 is coupled to proximal portions 14p and can be fixedly coupled or pivotally coupled via a pivotal coupling 14cop. Handpiece 15 can include or be coupled to an extension member 22. The distal portions 15d of the hand piece or extension member can be at least partially recessed within housing 14 to reduce friction or drag from the handpiece. An electrode or other energy delivery device 18 having an electrode cutting edge 18ce is coupled to distal portions 14d of housing 14 directly or via an insulative coupling 14icop.

Electrode 18 can be positioned distally to housing 14 and is configured to cut or dissect through tissue via the use of RF energy (other electromagnetic energy) to produce a selected plane of dissection within or between one or more tissue layers such as the subcutaneous layer of the skin or the muscle fascia. Electrode 18 and/or apparatus 10 can be configured to be coupled to a power source 20 via a power connecting member 20cm. In various embodiments, one or more rollers or roller elements 17 can be coupled to housing 14. Rollers 17 can be positioned at the distal portions 14d of housing 14, can be positioned adjacent, above or below electrode 18 or can be attached to the bottom 14b or the top of housing 14t. Rollers 17 positioned above the electrode, are configured to assist in rolling or advancing the nascently dissected tissue flap over housing 14. Rollers 17 positioned below can be configured to allow housing 14 to roll over underlying tissue as housing 14 is advanced in the dissection pocket 8dp at the target tissue site 8 or elsewhere.

Figure 2A:
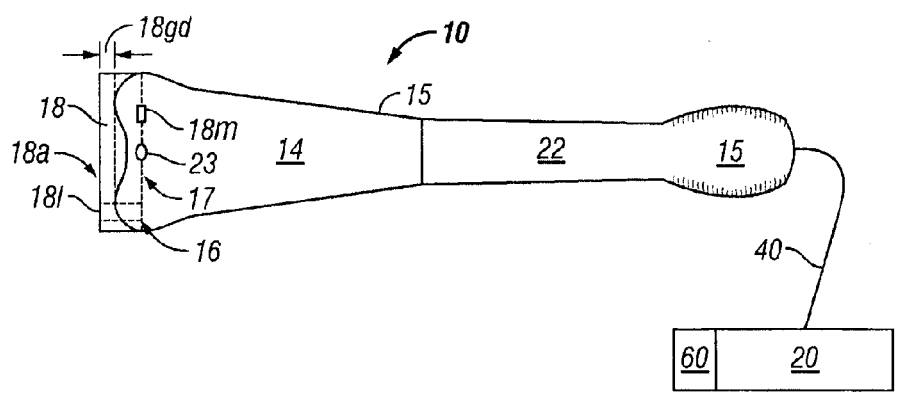
FIG. 2(a) is a cross-sectional view of one embodiment of an apparatus for dissecting or cutting tissue of the present invention.
Figure 2B:
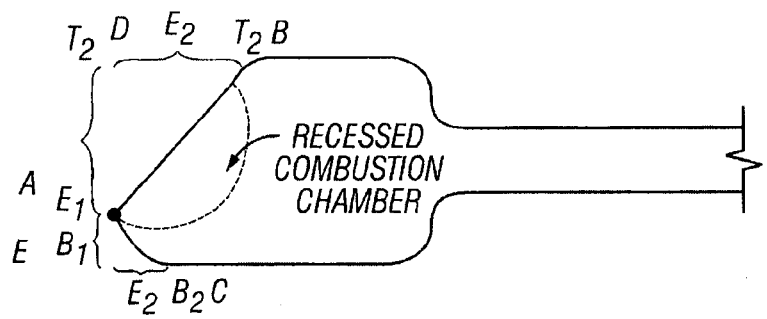
FIG. 2(b) is a cross-sectional view of another embodiment of the an apparatus for dissecting or cutting tissue of the present invention.
Figure 2C:
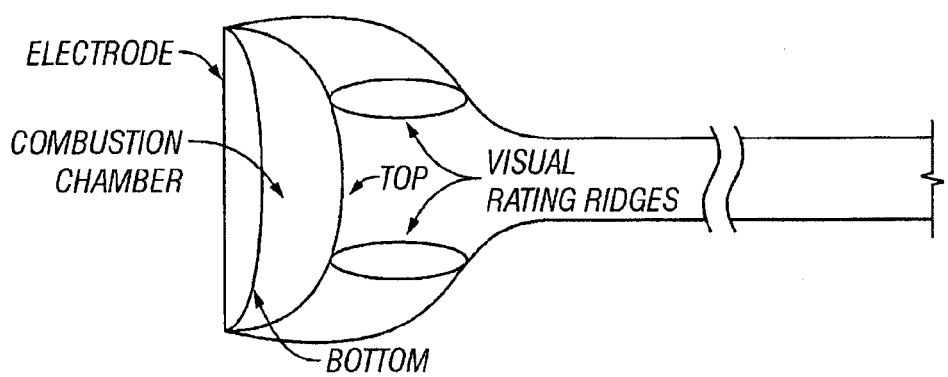
FIG. 2(c) is a top down view of another embodiment of the an apparatus for dissecting or cutting tissue of the present invention that includes a chamber.

Referring now to FIGS. 2(b) and 2(c), in one embodiment housing 14 is configured to be advanced under a tissue layer and control one of a depth of dissection or tissue flap thickness. Housing 14 thermally shields at least a portion of the tissue flap. Roller 17 can be coupled to housing 14, as more fully explained hereafter. Roller 17 is configured to smoothly advance housing 14 over tissue. Electrode 18 is coupled to housing 14 and has a geometry that substantially defines a plane of dissection.

In another embodiment, housing 14 includes a top with a top proximal section 14' and a bottom with a bottom proximal section 14". Top proximal section 14' has a geometry that facilitates creation of a skin flap with a substantially uniform thickness that includes a skin layer and an adjacent layer of subcutaneous tissue. Bottom proximal section 14" has a geometry that preserves a plane of tissue that is positioned adjacent to the adjacent layer of subcutaneous tissue.

In one embodiment, illustrated in FIG. 2(b), bottom proximal section 14" has a most proximal point at "A", and the top proximal section has a most proximal point at "B", wherein A is more proximal than B. Bottom proximal section 14" is defined by point A and a more distal point "C". Electrode 18 extends from point A to point B. Electrode 18 forms the hypoteneus of a triangle defined by points A, B, and a point D which is positioned at a more proximal position than point B. Bottom proximal section 14" forms a hypoteneuse of a triangle defined by points A, C and a point E, wherein E is more proximal than point C. In various embodiments, the distance between points D and A can be in the range of 1 mm to 2.5 cm, the distance between points D and B can be in the range of 0 mm to 1.5 cm, the distance between points A and E can be in the range of 0 mm to 1.5 cm, and the distance between points E and C can be in the range of 0 mm to 1.5 cm.

As illustrated in FIG. 2(c), housing 14 can include a chamber that facilitates creation of the skin flap.

In an embodiment shown in FIGS. 4 and 5(a), housing 14 can be substantially hood shaped with a configuration that allows housing 14 to function as a tissue guide and a tissue guard, or guide-guard to guide the electrode through tissue to produce a uniform plane of dissection and protect subjacent and overlying tissue layers from thermal injury as will be discussed more fully herein. The distal portion 14d of housing 14 or hood 14 can include a small recessed area 12 and the proximal portion of the hood can also include a recessed area 13, one or both of which can be substantially vertically centered on the vertical center line 14vc of the hood. The two recessed areas 12 and 13 can be curved or rectangular in profile.

Electrode 18 can be approximately positioned in the vertical center line 12vc of the recessed area with the cutting edge of the electrode 18ce protruding distally in front of housing 14 and out of recessed area 12 by a selectable distance (e.g. 1 to 40 mms). The electrode can be attached to housing 14 near the sides 12s of the recessed area 12. The distal portion of the hand piece 15d or extender 22d can be recessed under the proximal portions 14p of the hood housing 14 and can be attached in recessed area 13. The attachment can be via pivotal couple 14cop such as an axel that allows hand piece 15 to pivot up and down with respect to the vertical center 14vc of the hood. Alternatively, the hand piece 15 or extender 22 can be fixedly attached using a screw, nut, adhesive bond or other mechanical attachment 14am means known in the art.

In various embodiments, housing 14 can also be configured to avoid lacerating the skin envelope including full thickness lacerations. Such lacerations are also known in the surgical arts as "button holing". Means for avoiding skin lacerations or button holing (e.g. skin laceration avoidance means) can include one or more of the following configurations of housing 14: (i) configuring housing 14 such that the distal top portions of housing 14 are above the electrode (that is that 14he height of housing 14 is substantially above the electrode as is discussed herein, (ii) coupling the electrode to housing 14 the such that electrode and/or electrode plane is vertically bounded by the top an bottom portions of housing 14, (iii) positioning the electrode on housing 14 such that electrode plane or cutting plane is substantially aligned with the vertical center of housing 14, (iv) configuring housing 14 width to be greater than the electrode width (iv) configuring the electrode ends to be bounded on either side by housing 14 and (iv) configuring housing 14 to have a sheath portion on either end of the electrode.

One or more of these features can also be utilized to have housing 14 protect subjacent tissue from unwanted perforation, or laceration as housing 14 is advanced through tissue. Such subjacent tissue can include, without limitation, muscle, nerve, blood vessels, arteries, veins tendons and the like.

Figure 5A:
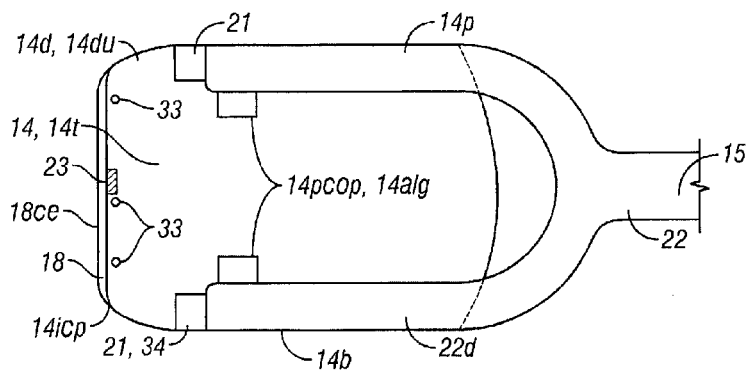
Figure 5B:
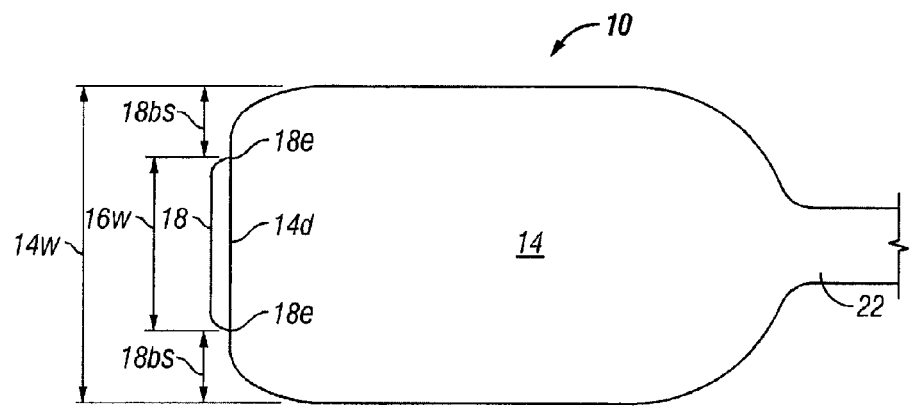
FIG. 5(b) is a cross-sectional view of an apparatus of the present invention for dissecting or cutting tissue that includes a buffer section on one or both electrode ends to bound the electrode.
Figure 5C:
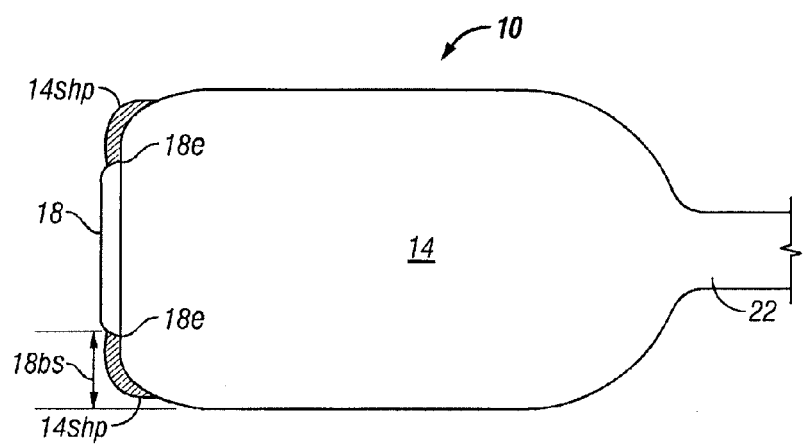
FIG. 5(c) is a cross-sectional view of an apparatus of the present invention for dissecting or cutting tissue with a housing that includes a sheath.

As shown in FIG. 5(b), in an embodiment for reducing button holing, housing 14 width 14w can be greater than the electrode width 18w and can be further configured to have a buffer section 14bs on one or both electrode ends 18e to bound the electrode. As shown in FIG. 5(c), housing 14 can also include sheath portions 14shp on either end of the electrode. Sheath portion 14shp can be configured to reduce button holing by shielding or overlying the electrode ends to keeping the electrode ends from protruding into the skin. This can be further facilitated by fabricating sheath portions 14shp from pliable polymers such that the sheath portions will at least partially deform when pressed into the skin envelope so as not to perforate or lacerate the skin envelope and also provide sufficient structural support and/or elastic cushioning to keep the electrode from do so.

Suitable pliable materials for sheath portions 14shp can include silicone and polyurethane elastomers and other resilient polymers known in the art such as PEBAX. Other means for reducing button holing can include the use of insulated sections 181 disposed near the electrode ends of the electrode as is discussed herein.

Figure 5D:
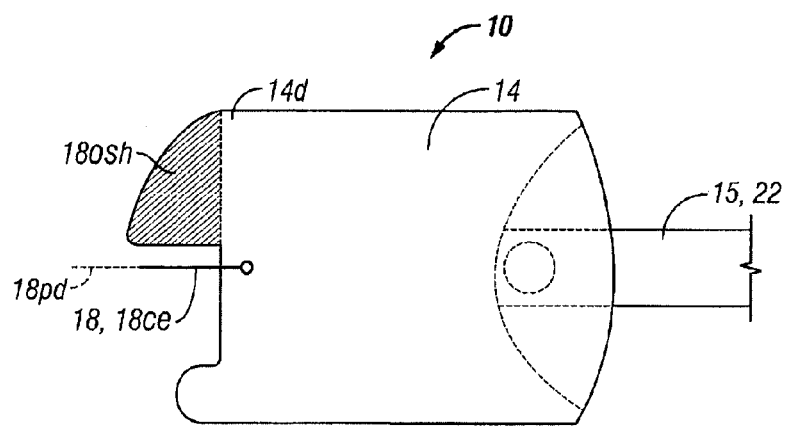
FIG. 5(d) is a cross-sectional view of an apparatus of the present invention for dissecting or cutting tissue that can be configured to allow the surgeon to advance the housing through the skin with the housing in a pitched-up fashion.
Figure 5E:
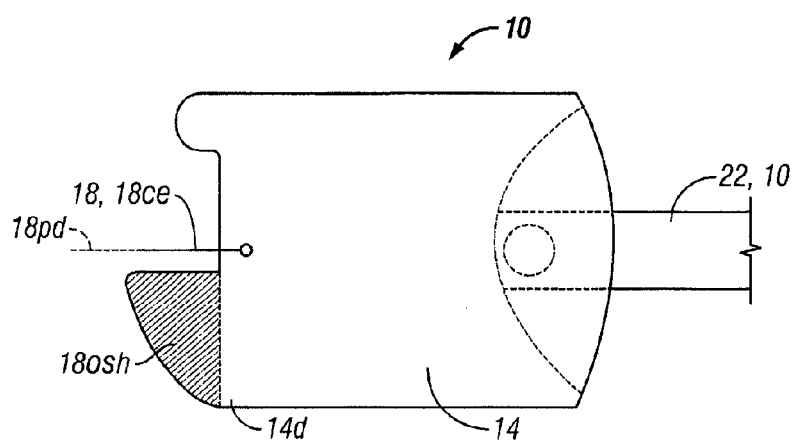
FIG. 5(e) is a cross-sectional view of an apparatus of the present invention for dissecting or cutting tissue that with an extender that can include a deflectable section.

In a related embodiments shown in FIGS. 5d and 5e, housing 14 can be configured to allow the surgeon to advance housing 14 through the skin with housing 14 in a pitched-up fashion. In use, advancing housing 14 in a pitched-up fashion helps to protect subjacent tissue layers (such as muscle, nerve and blood vessels, etc) as well as providing a tenting of the skin visually indicating to the surgeon where apparatus 10 is at least partially under the skin and that subjacent tissues are not being dissected. In various embodiments, housing 14 pitch can be accomplished by manual manipulation of the handpiece 15 and/extender 22 by the surgeon such that he or she sees the skin tenting or protuberance 8tent produced by and indicative of housing 14 being pitched up.

Alternatively in an embodiment shown in FIG. 5e, extender 22 can include a deflectable section 22def which the surgeon can manipulate by virtue of a actuating member 39 or deflection mechanism 25 and an actuator 15a' on the hand piece which can be configured to allow the surgeon to deflect extender selectable amount to pitch housing 14 at a selectable angel of attack 14aa with respect to skin surface or tissue layer 81 Actuator 15a' can be a slide mechanisms known in the art and can include graduated markings 15gm indicting angle of attack 14aa.

Also in this and related embodiments, electrode 18 can be configured to be swivelable through a selectable arc 18arc to have selected cutting angle 18aa by virtue of swivel or pivot mechanism 18sw. Swivel or pivot mechanism 18sw can be any swivel or pivot mechanism known in the art including a bearing mechanism. Also in an embodiment, swivel mechanism 18sw can be coupled to an actuator 15a" on hand piece 15 (by an actuating member 39), where actuator 15a" is configured to allow the surgeon to swivel electrode 18 to a selectable cutting angle 18aa.

Actuator 15a" can also be a slide mechanisms known in the art and can include graduated markings 15gm indicting cutting angle 18aa. In use, swivel mechanism 18sw can be configured to allow the surgeon to dissect tissue along a selected tissue plane 8pd (which can be substantially parallel to a select tissue layer 81) even while housing 14 is pitched up or pitched down.

Figure 6:
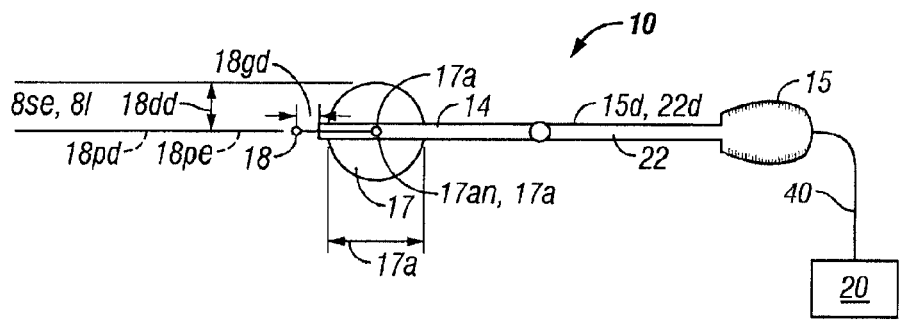
FIGS. 6, 7 and 8 are cross-sectional views of an apparatus of the present invention for dissecting or cutting tissue that include a roller.
Figure 7:
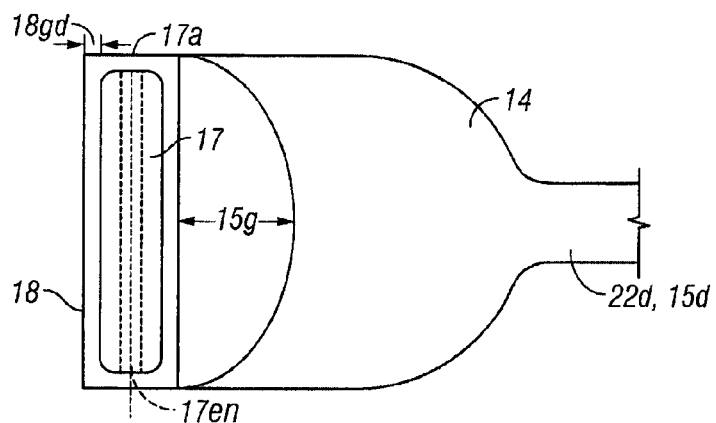

In an embodiment shown in FIGS. 6 and 7, apparatus 10 can comprise a roller 17 pivotably coupled to a hand piece 15 (or hand piece extender 22) via an axel 17a. The distal end 15d or 22d of the hand piece 15 or hand piece extender 22 can be substantially crescent shaped, with sufficient clearance space 15s to allow for movement of roller 17 and/or pivotal movement of the hand piece 15 or hand piece extender 22. Electrode 18 can be attached to the roller axis 17a, to the distal end 15d of the hand piece 15 or the distal end 22d of the hand piece extender 22.

In either configuration, the electrode and roller are in a fixed vertical relationship with each. The electrode can be positioned distally in front of the roller and preferably is substantially vertically aligned with the center of roller 17cen, but can also be positioned above or below the roller center. The electrode is positioned far enough in front of the roller to allow the developing skin envelope to slide over the roller after dissection by the electrode.

In various embodiments, this distance known as the electrode gap distance 18gd, can be 1 to 40 mm. Roller 17 can be configured to roll or advance subcutaneously over underlying tissue by the application of force from hand piece 15 and advance electrode 18 through tissue (such as subcutaneous tissue) to uniformly dissect a plane of dissection 8pd.

As described herein, in various embodiments, housing 14 can be configured to act as a tissue guide for advancing the electrode through tissue to produce a substantially uniform plane of dissection 8pd and also as guard to protect tissue and tissue layers 81 above and below the plane of dissection. In these embodiments, housing 14 can thus be a tissue guide-guard for performing uniform depth tissue flap dissection using an energized cutting means such an RF electrode. The above lying protected tissue layers can include the skin envelope including the dermal and sub-dermal plexus. The subjacent protected tissue can include nerves, muscle, tendon, arteries, veins and the like.

As a tissue guide, housing 14 can be configured to guide and stabilize the electrode through tissue to produce a plane of dissection 8pd having a uniform depth of dissection 8dd. More specifically it can be configured to function as a guide for generating a uniform depth of dissection 8dd during a minimally invasive procedure to undermine or dissect selected tissue layers 81 such as the skin envelope 8se using an electro-cautery cutting electrode 18 or other energy delivery device configured for tissue dissection or cutting.

The guiding function of housing 14 is to guide the electrode through tissue and control the dissection depth and the tissue flap thickness 8t can be accomplished by a variety of means including the shape, structure and material and mechanical properties of housing 14. For example, as described herein, the distal portion 14d of housing 14 can have a curved shape configured to facilitate smooth advancement of the dissected skin envelope 8se over the top of housing 14. This reduces the frictional and other forces, which may act on housing 14 to push the electrode and thus the electrode plane 18pe up or down and out of the selected plane of dissection 8pd.

In other embodiments the guiding function of housing 14 can also be accomplished by configuring housing 14 to function to stabilize the plane of the electrode 18pe (which substantially defines the plane of dissection) relative to the selected plane of dissection 8pd such that electrode plane 18pe does not substantially pitch up or pitch down into tissue as housing 14 is advanced or otherwise moved through tissue. This stabilization function can be accomplished through several means. First the plane of the electrode 18pe can be configured to resist tissue applied forces tending to deform its shape through the use of rigid materials for electrode 18 and/or strut members 19 (described herein) coupled to the electrode and housing 14 or a roller axel 17a described herein.

Figure 8:
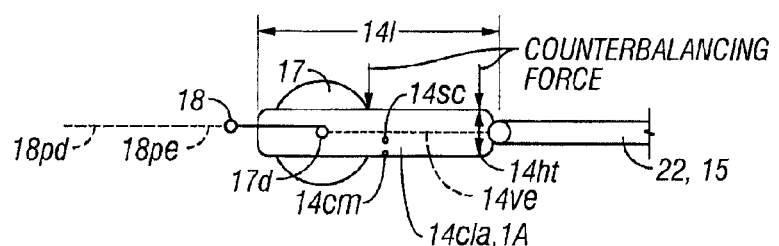

Housing 14 can be configured to resist or otherwise attenuate tissue applied forces causing the electrode plane to dip down or dip up. Referring now to FIG. 8, this can be accomplished by configuring housing 14 to act as a counterbalancing lever arm 14cla (at the point where housing 14 couples to the electrode such as the roller axel) to counter balance downward or upward tissue applied forces (or other forces) on the electrode. This in turn can be accomplished by configuring housing 14 to have sufficient length 141 and/or shape such that normal forces from tissue on housing 14 will counteract tissue applied forces on the electrode. In such embodiments the length of housing 14 can be between ¼ to 4 inches.

Housing 14 can have sufficient mass and/or length relative to the distance the electrode projects in front of housing 14 (also called electrode gap distance 18gd discussed herein) such that tissue applied forces and resulting torque or moment on the electrode will not be sufficient to overcome the counterbalancing torque/moment forces of housing 14. In embodiments the mass of housing 14 can exceed that of the electrode by a range of ratios from 1:10 to 1:100 and the length of housing 14 can exceed that of the electrode plane by a ratio range of 1:5 to 1:100. Also housing 14 can be configured to stabilize the electrode by having a center of mass 14cm (that of housing 14) located substantially at its geometric center 14gc or in a selected axis (e.g. x, y or z).

In other embodiments, stabilization can be achieved by configuring housing 14's center of mass 14cm to be located below housing 14s vertical center 14vc in a range of about 5 to 99% of half of housing 14 height 14ht with specific embodiments of 10, 25 and 75%.

Referring now to FIGS. 9-12 (showing embodiments of a stabilizing element) in other embodiments, stabilization of the electrode plane 18pe can be achieved by means of a stabilizing element 27 positioned proximally to housing 14 and coupled to housing 14 or the roller axis 17a. Similar to the description above, the stabilizing element serves to provide a counter balancing torque or moment arm opposing forces on the electrode or housing 14 causing the electrode plane 18pe to pitch up or down.

In an embodiment, stabilizing element 27 can be substantially planer having a thickness 27t thinner than the thickness 14t of housing 14 or roller diameter 17d, and having a plane 27p that this is substantially parallel to the electrode plane 18pe. Stabilizing element 27 can have a variety of shapes including, square, rectangular, rectangular with radiused edges, circular, semicircular, or fin-shaped.

Figure 9:
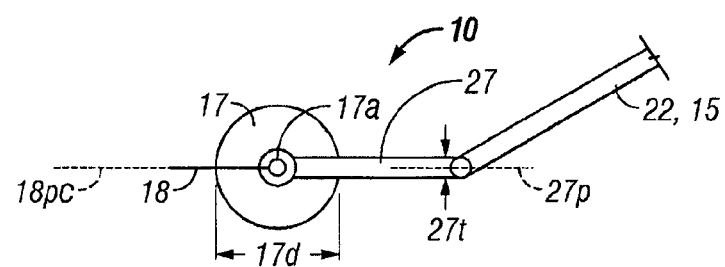
FIGS. 9 and 10 are cross-sectional views of an apparatus of the present invention for dissecting or cutting tissue that that has a flat rectangular section positioned proximally behind) the housing 14 and provide stabilization.
Figure 10:
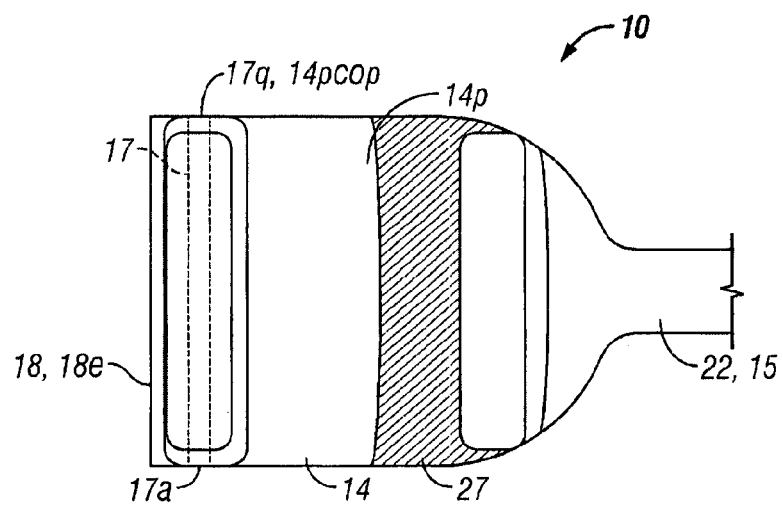
Figure 11A:
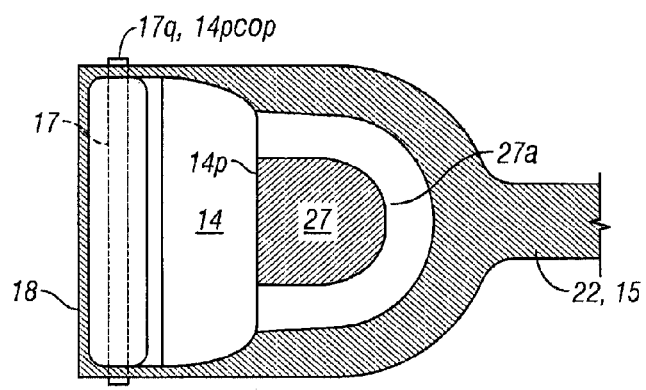
FIGS. 11(a) and 11(b) are cross-sectional view of an apparatus of the present invention for dissecting or cutting tissue that element with a substantially U-shaped section positioned proximal to housing.
Figure 11B:
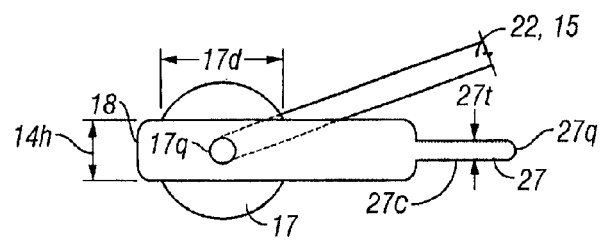

In an embodiment shown in FIGS. 9 and 10 the stabilizing element 27 can comprise a flat rectangular section positioned proximally (e.g. behind) housing 14 or roller 17. The element can be coupled to the roller axel 17a or the proximal section 14p of housing 14. In another embodiment, shown in FIGS. 11a and 11b element 27 can be a substantially U-shaped section positioned proximal to housing 14 or roller 17, with the apex of the U 27a, pointing away from the back (proximal direction) of housing 14.

Figure 12:
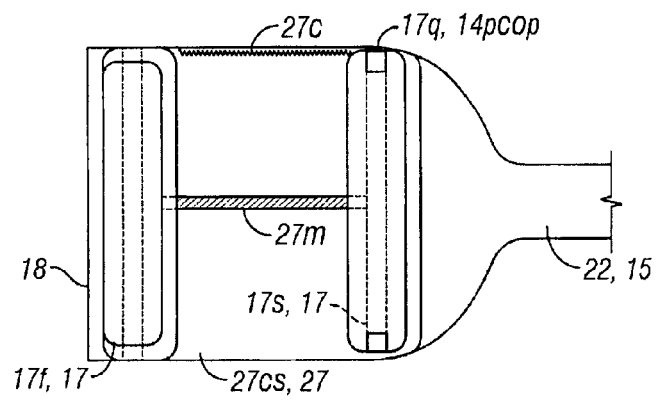
FIG. 12 is a cross-sectional view of an apparatus of the present invention for dissecting or cutting tissue that with a stabilizing element that can be positioned between a first roller and a second roller.

In yet another embodiment shown in FIG. 12, the stabilizing element 27 can be positioned between a first roller 17f and a second roller 17s. In a related embodiment, stabilizing element 27 can comprise a connecting section 27cs between the two rollers. In a related embodiment, the stabilizing element 27 can comprise a stabilizing strut member 27m connecting the first roller to the second roller.

In various embodiments, the thickness 27t of the stabilizing element can be in the range of 0.05 to 0.5 inches with specific embodiments of 0.1, 0.2 and 0.3 inches. Also the ratio of the thickness of the stabilizing element to the thickness/height of housing 14 14h or diameter 17d of roller 17 can be in the range of 1:1 to 10:1, with specific embodiments of 2:1, 4:1 and 6:1.

Element 27 can be fabricated from biocompatible polymers known in the art and described herein. In an embodiment, element 27 can be fabricated from low friction materials or have a lubricous coating 27c such as TEFLON® or other PTFE known in the art. In use the stabilization element, by stabilizing the electrode plane, helps the surgeon maintain a uniform depth of dissection as the electrode and housing 14 are advanced through tissue.

Figure 13A:
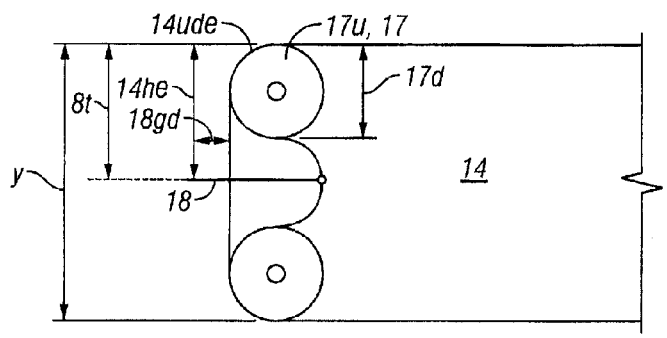
FIGS. 13a and 13b illustrate an apparatus of the present invention for dissecting or cutting tissue with a gap distance between the electrode and the roller configured to control or facilitate control of the thickness of the skin envelope or tissue flap and/or the dissection depth.
Figure 13B:
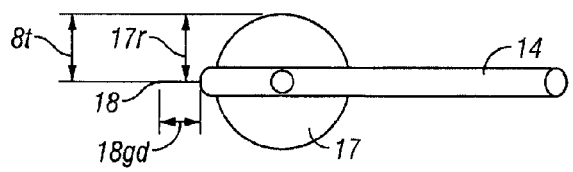

Referring now to FIGS. 13a and 13b, in various embodiments, the gap distance 18gd between the electrode and the roller and or between electrode and upper distal end of housing 14ude can be configured to control or facilitate control of the thickness 8t of the skin envelope or tissue flap and/or the dissection depth 8dd. The distance between the electrode and housing 14 can be in the range of 0.05 to 1 inch with specific embodiments of 0.1, 0.2, 0.25, 0.3. 0.5 and 0.75 inches. Smaller gaps can be employed for procedures utilizing smaller tissue flaps thickness and larger gaps for procedures using large flap thickness. Preferably, but not necessarily, electrode distance 18gd height is less than height 14he (the height of housing 14 above the electrode) and for embodiments using rollers 18gd is less than the radius 17r of 17 roller (or less than the diameter 17d for upper roller embodiments). Also height 14he can be configured to have the top of housing 14 high enough above the electrode to minimize button holing of apparatus 10 through the skin envelope (as discussed herein). In various embodiments this can be accomplished with a height 14he in the range of 0.25 to 2 inches with specific embodiments of 0.3, 0.5, 0.75, and 1.5 inches.

In related embodiments, flap thickness 8t and/or the depth of dissection 8dd can also be controlled by manipulation of (i) the ratio of the gap distance 18gd to distance 14he, defined as the gap to height ratio and/or (ii) the ratio of distance 18gd to the radius 17r (or less than the diameter 17d for upper roller embodiments) of roller 17, defined as the gap to radius ratio. In various embodiments, either of these two ratios can be in the range of 1:1 to 1:10 (i.e., the radius of the roller is 10 times greater than the electrode gap distance) with specific embodiment of 1:2, 1:4, 1:5 and 1:7. In addition, control of the depth of dissection and skin flap thickness manipulation of one or both of these ratios, can be used to control or affect (i) the amount of conductive heat transfer to the dissected skin envelope/tissue flap, (ii) temperature of the dissected skin envelope/tissue flap, (iii) the amount of tightening of the skin envelope, (iv) the tension of the nascent skin envelope and (v) the amount of cutting or separation force applied to tissue at the plane of dissection. Large ratios will more readily push the nascent skin envelope away from the electrode after dissection and thus reduce the amount of conductive heat transfer to portions of the envelope (from RF energy delivery) and also provide a thermal shielding to the envelope/tissue flap. Larger ratios may also by used to produce more of a cutting or wedge affect in the tissue.

Figure 14:
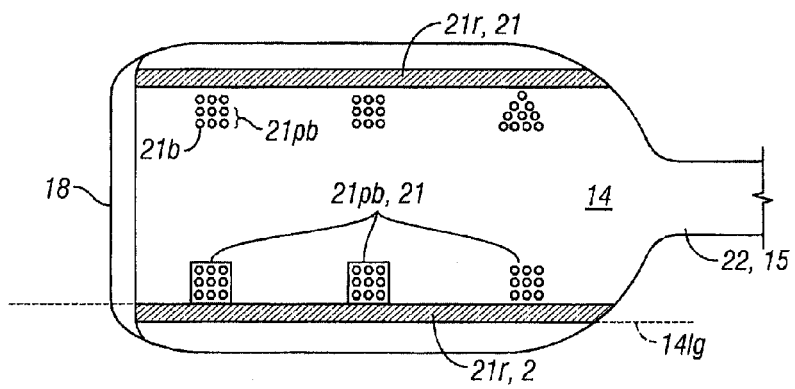
Figure 15:
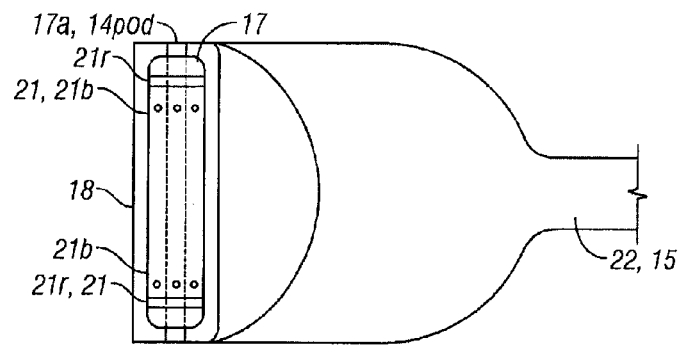

Referring now to FIGS. 14-18 (illustrations showing embodiments having trans-cutaneous markers), in another approach for facilitating control of dissection depth and flap thickness in various embodiments, housing 14 can have one or more ridges 21r, protuberances or bumps 21b or patterns 21pb of bumps having a substantially parallel orientation (or other selected orientation) to the longitudinal axis 141a of housing 14 as shown in FIG. 14. The ridges or bumps can be configured as trans-cutaneous markers 21 to provide trans-cutaneous visualization of one or more of the following: (i) the depth of dissection, (ii) the width of the dissection plane, and (iii) the path of the plane of dissection. In related an embodiment shown in FIG. 15, roller 17 can have one or more ridges 21r or bumps 21b configured as trans-cutaneous markers to provide similar visualizations.

Figure 16A:
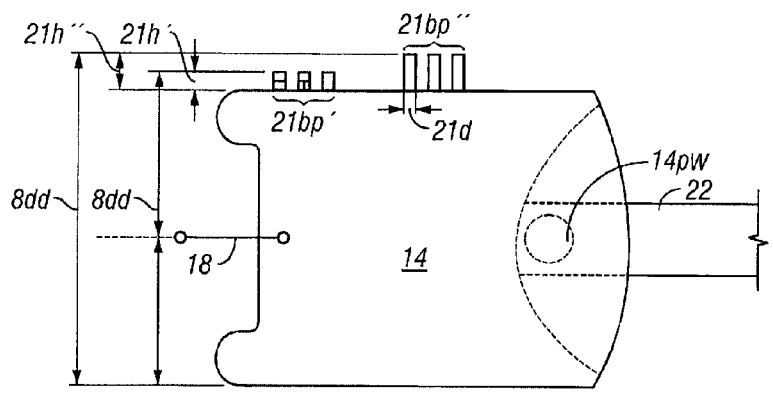
FIGS. 16(a) and 16(b) illustrate an apparatus of the present invention for dissecting or cutting tissue with a pattern of bumps which corresponding to different dissection depths, to provide the physician with a real time visual indication of the depth of dissection.
Figure 16B:
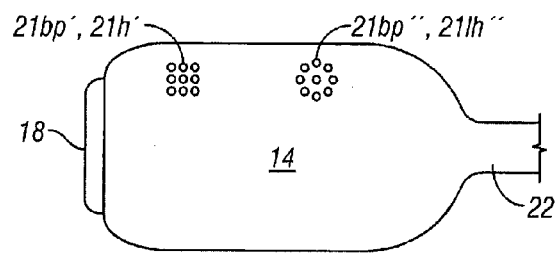
Figure 17:
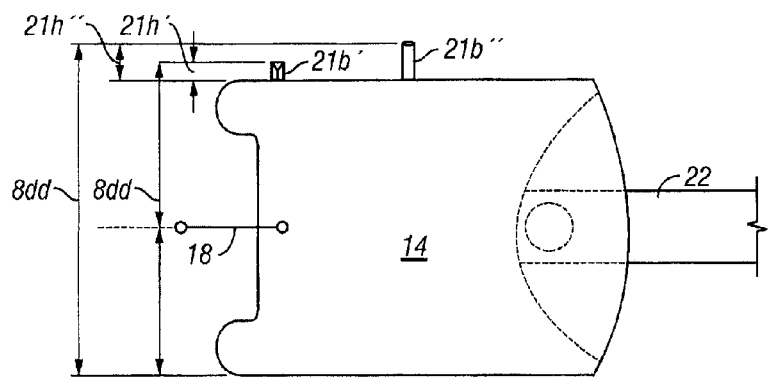

As shown in FIGS. 16a and 16b, the pattern of bumps 21bp can include different patterns of bumps (for example a first bump pattern 21bp' such as a square and a second bump pattern 21bp" such as a circle) having different heights 21h' and 21h" corresponding to different dissection depths 8dd, to provide the physician with a real time visual indication of the depth of dissection, including any variations in the desired depth as housing 14 is advanced over the selected tissue plane. In use, these and related embodiments can be configured to provide the physician with both a qualitative and quantitative indication of the depth of dissection. In related embodiments, the height of the ridges or bumps can be adjustable to allow the physician to have trans-cutaneous visualization of pr at different depths of dissection. This can be accomplished using an adjustment means $21a$ known in the art including a setscrew, ratchet, swage fitting, locking device, clamp and the like.

In various embodiments, the shape of the visualization bumps $21bs$ can include round, square, diamond oval triangular and combinations thereof. In an embodiment shown in FIG. 17, different bump shapes can have different heights $21h$, which correspond to different dissection depths $8dd$. Specifically bumps 21 can include a first bump $21b'$ having a first height $21h'$ and second bump $21b''$ having a second height $21h''$. For example, a diamond shape bump could have a height that correspond to a dissection depth of 4 mm and round shaped bump could have a height that corresponds to a dissection depths of 8 mm. In use these and related embodiments of housing 14 having a pattern-height specific visualization bumps 21 allows the surgeon to readily discern the dissection depth as well as changes there to without having to palpitate the skin, endoscopically view the plane of dissection or remove the device from the tissue site. Further these and related embodiments can also allow the surgeon to readily discern the slope of housing 14 advancement and thus readily make adjustment to maintain the plane of dissection or change it if so desired without having to remove either hand from the hand piece. This in turn provides for a greater degree of control of the dissection procedure.

Figure 18:
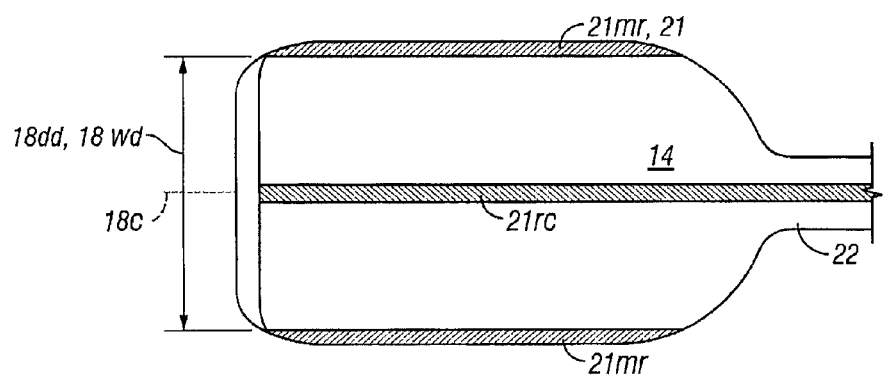
Figure 19A:
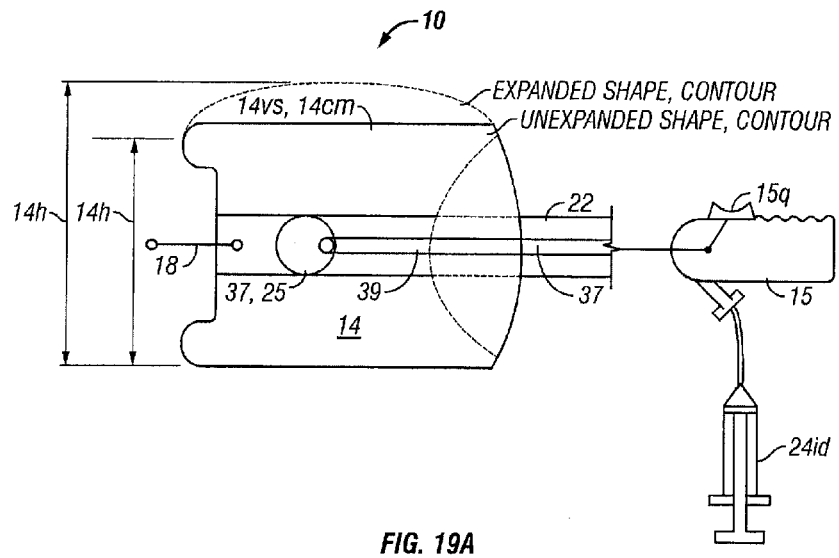
Figure 19B:
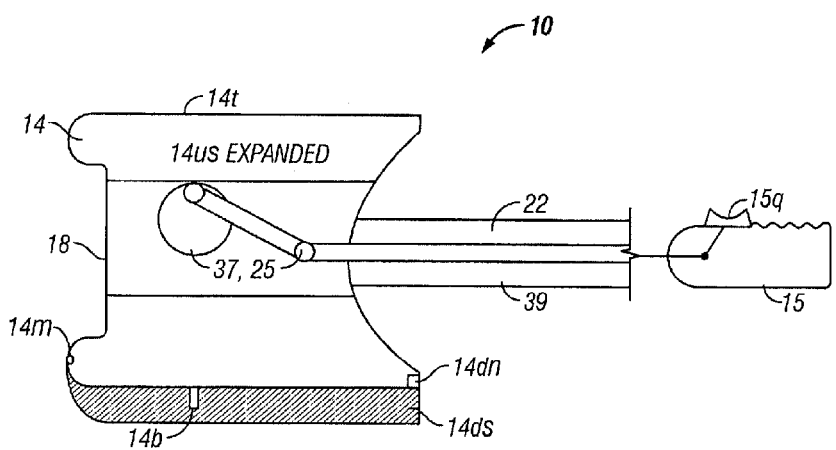

Also in an embodiment shown in FIG. 18, housing 14 or roller 17 can have a pair of marking ridges $21mr$, corresponding approximately to dissection width $18wd$ of the electrode to provide a visual bracketing or cue of the width $8wd$ of the plane of dissection. In a related embodiment, housing 14 or roller can include a third ridge $21rc$ whose position corresponds to the lateral center $18c$ of the electrode, to provide an indication of the center line $8cl$ of the plane of dissection. In another embodiment, the guard/guide components of housing 14 can be configured to mimic the visual impression that a surgical instrument, such as Metzenbaum scissors, make on the skin surface during the dissection process.

Referring now to FIGS. 19a-19b and 20a-20b (Figures illustrating an embodiment having a detachable section or movable or variable shaped contour). In various embodiments, the shape, contour or height of housing 14 can be selectable and can be adjustable using an adjustment mechanism known in the art such as a telescoping mechanism or articulated mechanism or using a variable size roller device 17. Also in various embodiments, the electrode housing can have different widths and different dissection depths. The width $14w$ and/or dissection depth $8dd$ of housing 14 can be pre-selected or adjusted depending on the surgical application (e.g. cutting into dermal, fascia or fat tissue, face lift etc). In various embodiments, the dissection depth $8dd$ can be in the range of 0 to 2 inches with specific embodiments of 0.1, 0.2, 0.25, 0.5, 0.75 and 1.0 inches.

An embodiment for adjusting the height or other dimension of housing 14 can include a detachable section or shim $14ds$. Detachable section $14ds$ can attach to the bottom $14b$, top $14t$ or other area of housing 14 using a snap fit, spring loaded latch or other reversible detachment mechanism $14dm$ known in the art. Detachable section $14ds$ can be of varying height, but can otherwise have the same dimensional footprint or profile as housing 14. In various embodiments, all or portions of housing 14 can be variable shape portions $14vs$ configured to be variable in shape, contour and/or dimension.

Means for varying the shape and dimensions of housing 14 can include configuring portions of housing 14 to be expandable or include an integral expandable member $14im$ (such as expandable balloon described herein and also known in the medical device arts) or use of a lifting or force generating mechanism 37 such as a spring, cam or lever that is integral or otherwise disposed within housing 14. Expandable member $14im$ can be configured to be operator actuable via device $15a$ which is coupled to an inflation device $24id$ which can be pressure source $24p$.

Lifting mechanism 37 can also be configured to be operator actuable via mean of a control wire, rod or other actuating member 39 coupled to the hand piece 15 via an actuating device $15a$. In embodiment actuating device $15a$ can be a slide, thumb switch, rocker arm and the like. In embodiment force generating mechanism 37 can also comprise deflection mechanism 25 described herein.

In various embodiments, variable shaped portions $14vs$ can be configured to control or alter one more of the following parameters: (i) change the electrode gap distance $18gd$, (ii) change the height of housing 14, (iii) change the height of housing 14 above the electrode, (iv) change the contour of housing 14 for example increase or decrease an amount of taper or concavity (v) change the angle at which the skin envelope slides over housing 14, (vi) change the height of the nascent dissected skin envelope above housing 14, (vi) change the distance between the newly dissected superior and inferior tissue layers, (vii) change the amount of tension in the developing skin envelope, (viii) change the stabilizing function of housing 14 and (ix) change the wedge or tissue separating qualities of housing 14. Manipulation of one or more of these parameters can in turn allow the physician to vary the shape of housing 14 to control one or more of (i) tissue flap thickness, (ii) the angle of the plane of dissection, (iii) the amount of heat transfer to the selected portions of the skin envelop/tissue flap and the associated temperature of those portions, (iv) the amount of thermal conductive tightening of selected portions of the skin envelope/tissue flap and (v) the amount of thermal injury of selected portions of the skin envelope/tissue flap.

For example, in an embodiment shown in FIGS. 20a and 20b (drawing showing use of a variable shaped housing 14 to expand or contract an insulatory pocket between the electrode and the skin envelope) tissue expandable variable shape portion $14vs$ can be used to vary the height $14h$ of housing 14 to vary the vertical distance $14dse$ between the electrode 18 and where the nascent skin envelope/tissue flap $8se$ first contacts the top of housing $14t$ so as to create, increase or decrease an insulatory space or pocket $8ip$ between the electrode and the developing skin envelope/tissue flap. This serves in turn to decrease or increase the amount of conductive heat transfer to the skin envelope which can be used to control the amount of collagen contraction and/or thermal injury of selected portions of the skin envelope.

Referring now to FIGS. 1-4, 13, 21, 22a and 22b in various embodiments, the guarding function of housing 14 can be configured to protect the dermal and sub-dermal vascular and neural plexus or other selected layer of the skin envelope or tissue flap from thermal injury and/or necrosis directly or indirectly resulting from the delivery of energy from electrode 18 (or other energy delivery device) during the dissection procedure. This is accomplished by configuring housing 14 to shield, insulate or otherwise distance portions of the skin envelope or tissue flap from RF current and/or thermal current (e.g. via conduction heat transfer) resulting from RF energy delivery to the target tissue site 8 (e.g. the plane of dissection).

One or more of these functions of housing 14 can in turn be accomplished through selection of one or more of the shape, dimensions, mechanical and material properties of housing 14. For example, in an embodiment shown in FIG. 4, the top of housing 14t can have a curved or curved tapered shape 14cs at or near its distal portion 14d that is configured to guide or direct the nascent skin envelope 8se over housing 14 and away from the electrode 17. By directing the skin envelope in the manner, the shape of housing 14 reduces the amount of heat transfer from the electrode to the skin envelope after dissection.

This skin envelope/tissue flap directing function can also be facilitated by selection of the electrode gap distance 18gd described herein. The electrode gap 18gd distance can be adjusted (by electrode advancement means described herein) for variations in flap thickness, tissue type and tissue mechanical properties (e.g. bending modulus) to optimize flap/envelope slide over. For example, electrode gap distance can be increased for more rigid tissue (e.g. cartilage or muscle one versus adipose tissue) and similarly, the degree of curvature of section 14cs can be decreased (e.g. the radius of curvature is increased). In various embodiments, electrode gap distance can be adjusted between 1 and 60 mm.

Figure 21:
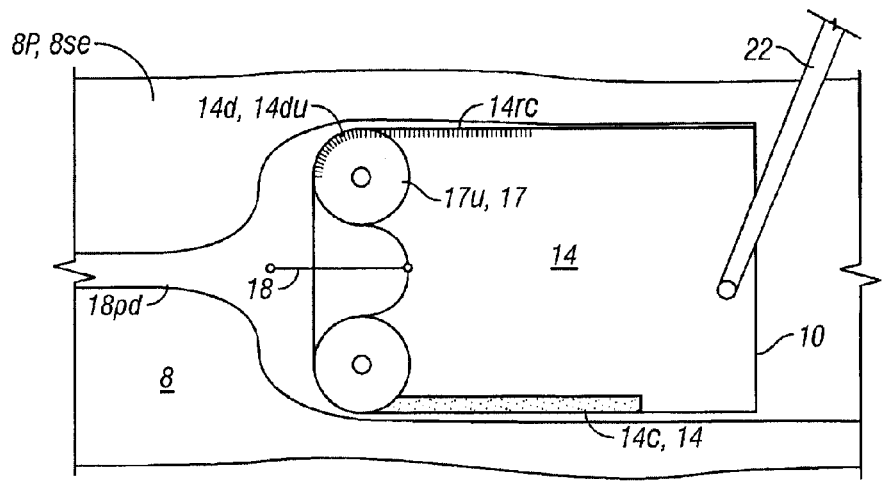
FIGS. 21 through 22(b) illustrate an apparatus of the present invention for dissecting or cutting tissue that provides a guarding function of the housing to protect the dermal and sub-dermal vascular and neural plexus or other selected layer of the skin envelope or tissue flap from thermal injury and/or necrosis.

In an embodiment shown in FIG. 21(embodiment of apparatus 10 with a roller positioned at top of housing 14), the skin envelope sliding process (and thus the shielding function of housing 14) can facilitated by the placement of a roller 17 on the distal upper portion 14du of housing 14 above and proximal to the electrode. The roller 17 serves to reduce friction between housing 14 and the skin envelope. In embodiments shown in FIGS. 4 and 22a, reduced friction between housing surface 16 and the skin envelope and thus smooth slide over can also be facilitated by use of a lubricous coating 14lc over the top 14t or other portions of housing 14, particularly the distal top portions to reduce friction between housing surface 16 and the skin envelope 8se.

Figure 4:
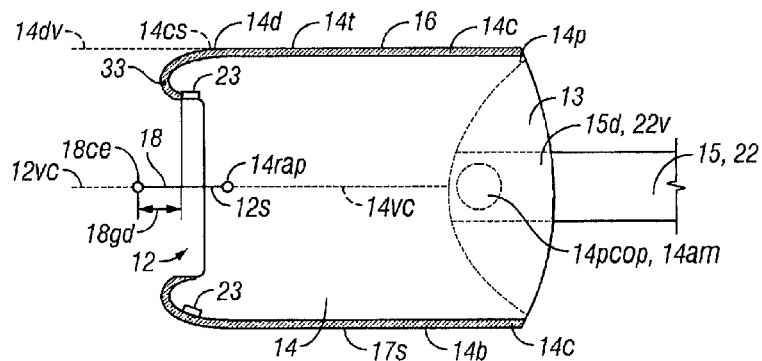
FIGS. 4 and 5(a) are cross-sectional views of an apparatus of the present invention for dissecting or cutting tissue with a housing that can function as a tissue guide and a tissue guard, or guide-guard to guide the electrode through tissue to produce a uniform plane of dissection.
Figure 22A:
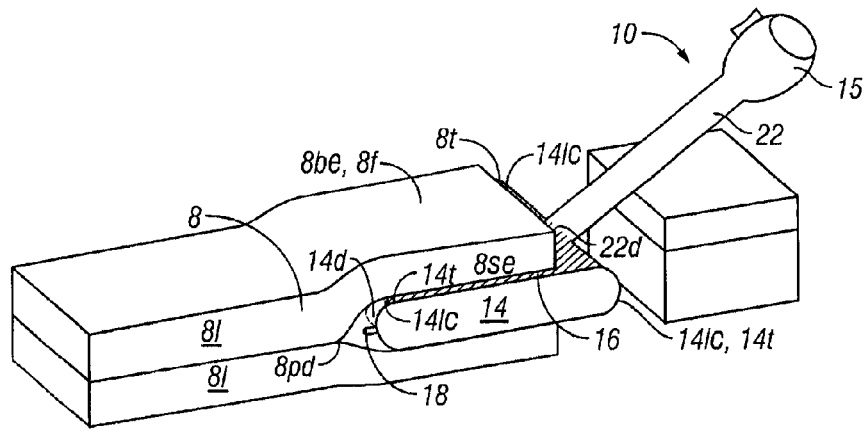
Figure 22B:
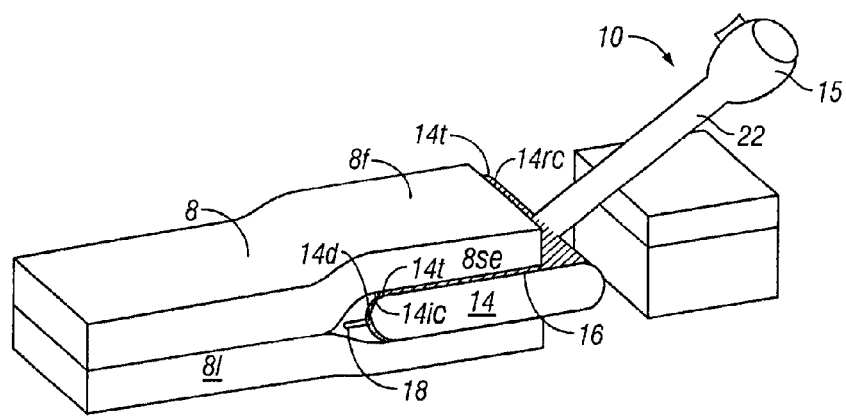

The shielding function of housing 14 can also be facilitated by configuring the distal 14d and top portions 14t of housing 14 surface to have a thermally and electrically insulative coating 14ic described herein which can be configured to shield the nascent skin envelope from direct ohmic heating by the electrode as well as conductive heating from one or more of the electrode, tissue vapor and heat of the surrounding tissue (see FIGS. 4 and 22b).

Figure 23:
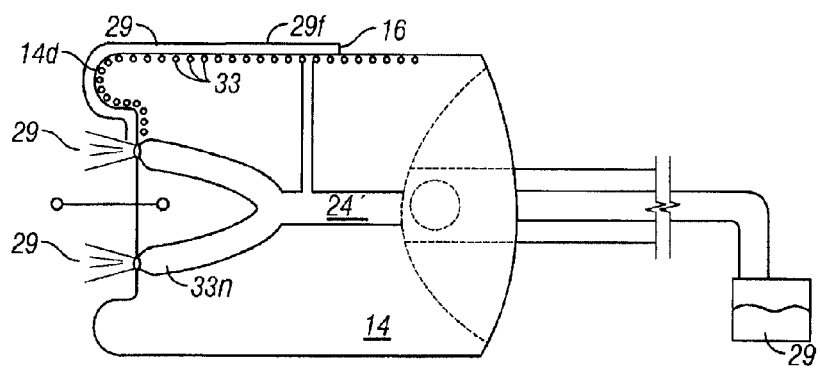
FIG. 23 through 25 illustrate an apparatus of the present invention for dissecting or cutting tissue that includes delivery of a cooling fluid.
Figure 24:
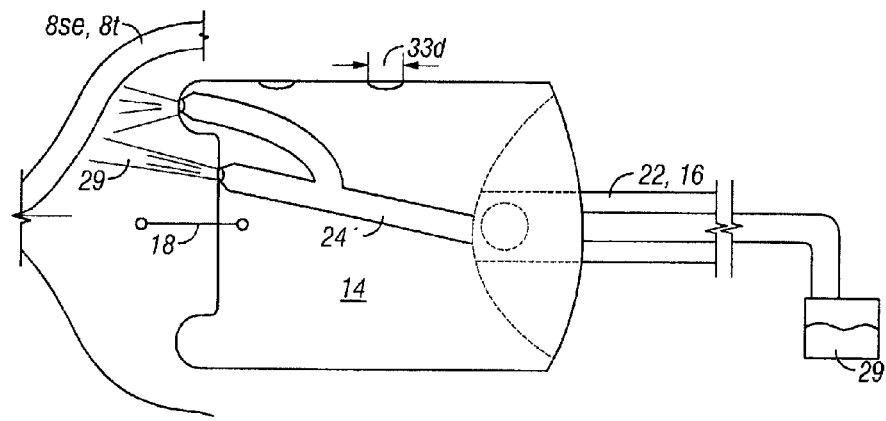
Figure 25:
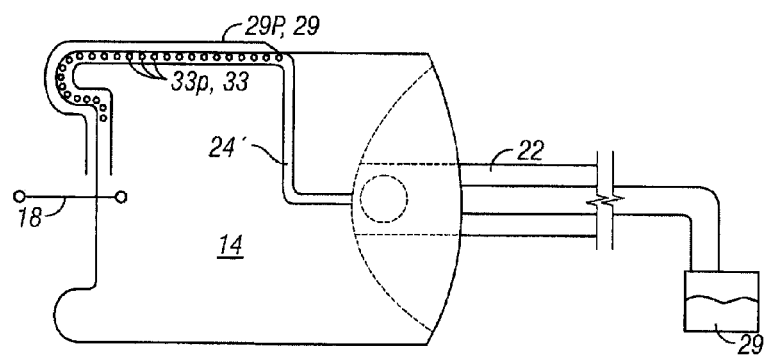

Referring now to FIG. 23-25 (Figure showing embodiments of housing 14 having fluid distribution ports) In various embodiments, the tissue protective or shielding function of housing 14 can also be accomplished by the delivery of cooling fluid through one or more fluid distributions ports or apertures 33 as is shown FIG. 23. Apertures 33 can be fluidically coupled to one or more lumens 24' and can be configured (by virtue of their size and shape) to ooze, infuse or spray a cooling fluid 29 to the cool all or selected portions of the overlying skin envelope/tissue flap and/or underlying tissue (e.g. muscle) as well. This and related embodiments can be configured to produce a reverse thermal gradient in the skin envelope or tissue flap. That is subjacent layers/or structures in contact with the cooling solution such as the dermal-subdermal plexus are cooled while the overlying collagen containing layers such as the dermis are at a selected elevated temperature due to conductive heat transfer from RF energy delivery from electrode 18.

In this way, embodiments using cooling solution can allow for collagen contraction of the dermis and, hence skin tightening, while preventing or minimizing damage of the dermal and sub-dermal plexus and thus facilitates or helps to maintain the viability of the newly dissected skin envelope or tissue flap both in the short after it is reattached and in the long term. Thus embodiment using cooling solution can be configured to improve the postoperative viability of the tissue flap or skin envelope. Moreover, embodiments of apparatus 10 and methods of the invention that employ cooling of the skin envelope via cooling solution or other cooling means can also be utilized to reduce the incidence of one or more post operative complications such as tissue necrosis, nerve or sensation loss, infection, skin dis-coloration or un even coloration which can occur due to damage of sub-dermal dermal plexus.

Apertures 33 can be positioned throughout the surface of housing 14 including tissue contact surface 16, singularly or in selectable patterns such as a substantially circular or linear pattern. In one embodiment apertures 33 can be configured and distributed on the surface of housing 14 to produce a film 29f of cooling fluid 29 that oozes or wicks out of the apertures and cools the skin envelope by combination of convective and conductive cooling. Film 29f can also be configured as a lubricous film that reduces the friction of housing 14 with overlying and underlying tissue layers and thus facilitates smooth advancement of housing 14 between tissue layers during dissection process or positioning of housing 14 within the tissue pocket.

All or portions of apertures 33 can also be configured as nozzles 33n to spray cooling fluid (which can be a liquid or a gas) onto the skin envelope and/or onto portions of electrode 18. In a particular embodiment apertures 33 or nozzles 33n can be positioned on the distal portions 14d of housing 14 so as to infuse or spray cooling solution onto the electrode to cool the electrode or otherwise prevent the buildup of charred tissue on the electrode. In another embodiment apertures or nozzles 33n can be positioned on the top and/or top distal portions of housing 14 to infuse or spray cooling solution onto the skin envelope or tissue flap which is in close proximity to the electrode so as to cool the skin envelope/tissue flap immediately or near immediately after it is dissected from underlying tissue layers.

In a related embodiment shown in FIG. 24, apertures 33 can positioned or otherwise directed to infuse or spray cooling solution onto the skin envelope or tissue flap at a selectable distance proximal from the electrode. In use this configuration can allow the skin flap to continue to be heated or otherwise remain at an elevated temperature (e.g. cook) for a selectable time sufficient to cause thermal collagen contraction but stay below a level of thermal injury to damage the subdermal plexus. In related embodiments apertures 33 or nozzles 33n can also be configured to provide irrigation within the pocket of dissection 8pd and/or surrounding tissue layers to remove debris and blood and assist in endoscopic visualization.

In various embodiments, apertures 33 can be substantially round, oval or other shape and can be produced by molding, machine drilling, laser drilling and like methods known in the medical device arts. Apertures 33 can have a diameter 33d in the range of 0.0001 to 0.5 inches with specific embodiments of 0.001, 0.005, 0.01, 0.05, 0.1 and 0.25 inches. Larger aperture diameters can used for infusing embodiments and smaller diameters for oozing embodiments. For oozing embodiments, apertures 33 can have a diameter 33d in the range 0.001 to 0.01 inches. Aperture 33 can also be configured for the delivery of other fluids as well such as electroconductivity enhancing solutions (e.g. saline), medicament solutions (e.g. anesthetics), irrigating solutions, and other solutions used in plastic surgery procedures.

In an embodiments shown in FIG. 25, apertures 33 can also comprise a porous section 33p coupled to surface of housing 14 and fluidically coupled to one or more lumens 24'. Porous section 33*p* can be configured (by virtue of their porosity, and wetting characteristics) to ooze or wick fluid 29 including a fluid film 29*f*. In an embodiment, porous section 33*p* can be made from a porous polymer membranes or polymer foam known in the art such including but not limited to knitted polyester, continuous filament polyester, polyester-cellulose, rayon, polyamide, polyurethane, polyethylene and the like. Suitable commercial products include, (i). OPCELL available from Centinal Products (Corp., Hyannis, Mass.), (ii). ULTRASORB, HC 4201 or HT 4644 MD available from Wilshire Contamination Control, (Carlsbad, Calif.) and polyethersulfone membranes (SUPER MEMBRANE) manufactured by the Pall Corporation (Ann Arbor, Mich. or East Hills, N.Y.).

Figure 26:
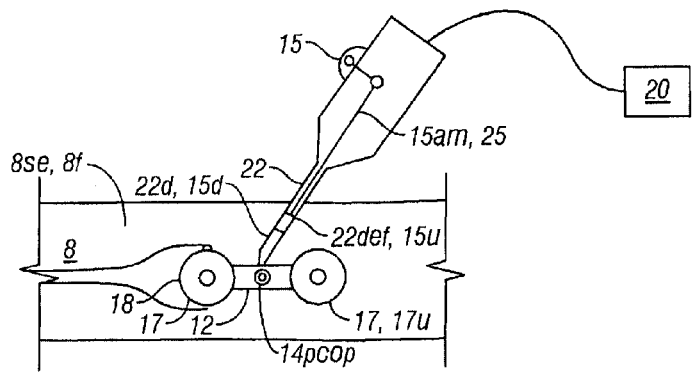
FIGS. 26 through 28 illustrate an apparatus of the present invention for dissecting or cutting tissue that is configured to dissect tissue in deeper planes of dissection than the dermis or superficial fascia.
Figure 27:
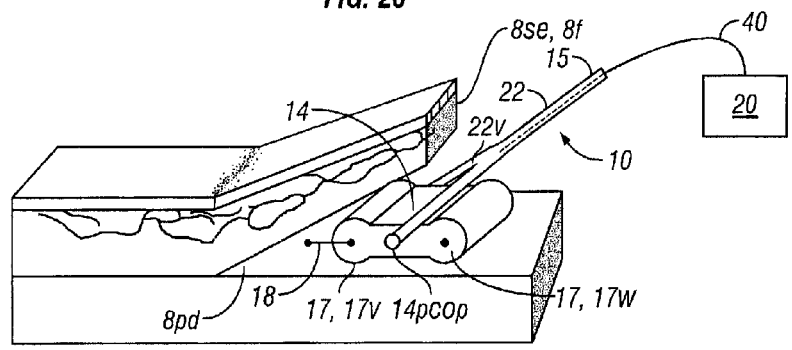
Figure 28:
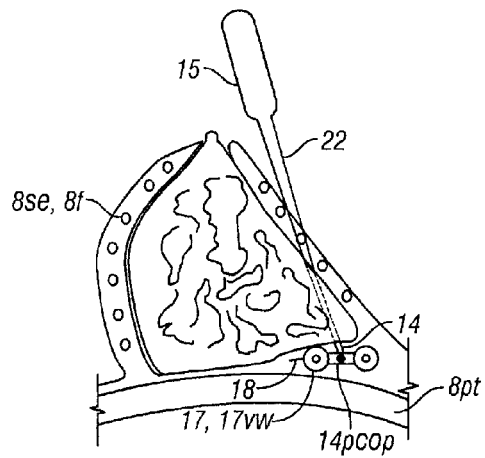

Referring now to FIGS. 26-28, in other embodiments apparatus 10 can be configured to dissect tissue in deeper planes of dissection than the dermis or superficial fascia. In one embodiment, apparatus 10 can be configured to produce a plane of dissection 8*pd* as deep as the muscle facial layer or deeper. In an and related embodiment shown in FIG. 26, housing 14 can include two rollers 17 or four wheels 17*w*. Hand piece 15 is pivotally coupling either directly to housing 14 at pivotal coupling 14*pcop* or indirectly via the coupling of extender 22 to housing 14 at pivotal coupling 14*pcop*. The pivotal coupling 14*pcop* can be configured to allow the hand piece and extender to swing through and arc of 180° or greater while housing 14 is located within the tissue pocket and under one or more tissue layers. Portions of the extender or hand piece, such as distal portions 15*d* and 22*d* can be configured to be deflectable portions 15*def* or 22*def* via means of an actuation member 15*am* (e.g. pull wires and the like) or other deflection mechanism 25

In use, deflectable embodiments of the hand piece or extender can be configured to allow the surgeon to gain access to obstructed or difficult to reach target tissue layers by deflecting the extender or hand piece around the obstruction (e.g. bone, blood vessels, cartilage, organs) and still transmit axial force to advance housing 14 through an embodiment of method for doing a deeper tissue dissections is illustrated in FIG. 28 here apparatus 10 can be utilized to produce a deep plane of dissection to dissect the glandular breast tissue from the *Pectoralis Fascia*. In this embodiment, dissection of the fascia can be initiated at a tissue perimeter 8*tp* where the skin envelope or tissue flap merges directly merges with the muscle fascia layer. This dissection of the muscle fascia can be done after or before the skin envelope is dissected from the tissue site. Embodiments of this method can be utilized for one or more of a skin sparing mastectomy, lumpectomy or even biopsy procedures. They can be utilized for skin sparing implant procedures of pace makers; cardiac device battery, power packs, energy converters, or control devices; or insulin pumps and the like in the breast, pectorolis or even other regions such as the abdominal regions through the selected tissue plane.

Figure 29B:
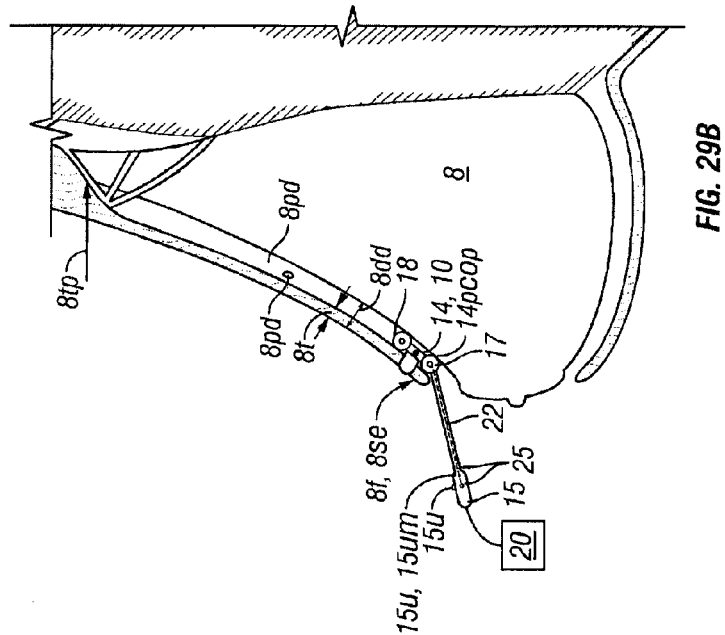
FIGS. 29(a) and 29(b) illustrate an apparatus of the present invention for dissecting or cutting tissue configured to dissect fascial layers by a variety of different approaches.
Figure 29A:
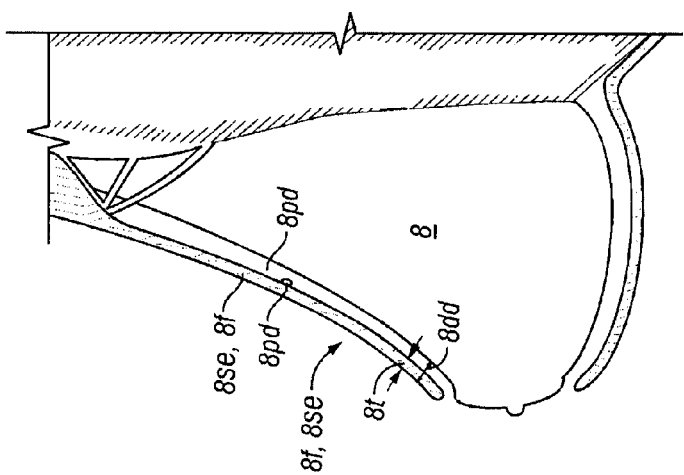
Figure 32:
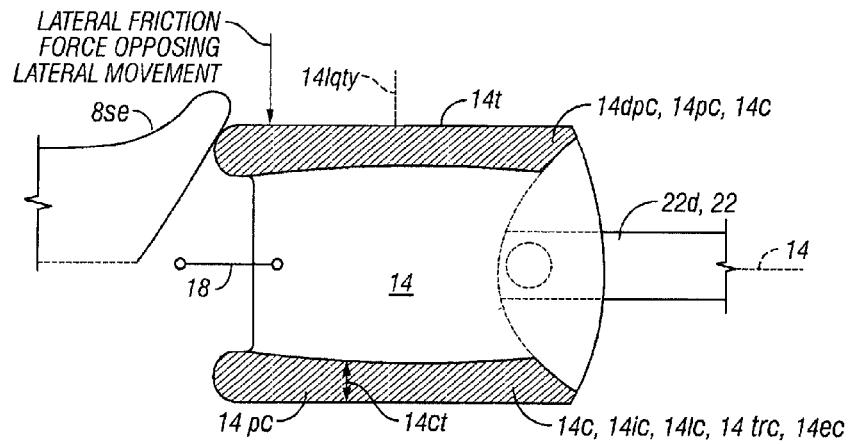
FIGS. 32 through 34 illustrate an apparatus of the present invention for dissecting or cutting tissue with a housing fabricated from any number of medical polymers.

In related method embodiments shown in FIGS. 29*a* and 29*b*, apparatus 10 can be configured to dissect fascial layers by several different approaches. One method is to start the facial dissection at a tissue perimeter where the fascia and the dermal layer/subcutaneous layers converge such as the perimeter of the breast. Another approach is make an angled dissection or cut down to the deeper layer using the transcutaneous markers to assess the dissection depth 8*dd* and the angle; the third approach is to make an incision down to the fascia or deeper tissue layer and then insert or advance housing 14 through incision to facial layer. In an embodiment, housing 14 can be inserted vertically through the incision and then pivoted or reoriented to a horizontal position on the selected tissue layer to be dissected using a pull/push wire or rod 15*w* or other actuating member 15*am* (or other deflection mechanism 25 known in the art) disposed within extender 22 or hand piece 15 and operable by actuator 15*a* on or coupled to the hand piece.

Pivoting of housing 14 can be configured to occur at pivotal coupling 14*cop* or other point. In a related embodiment using this approach (advancement through an incision), embodiments of apparatus 10 having a deployable housing 14 can be utilized whereby housing 14 is advanced through the incision in a non deployed state and then deployed to the deployed state (using a deployment mechanism described herein or known in the medical device arts such as a pull wire or deployable balloon) once the selected tissue layer is reached. Also in embodiments for doing deep plane dissection all, or portions of electrode(s) 18 can be wedge shaped (as described herein) to assist in applying force to initiate can continue the plane of dissection.

Referring now to FIGS. 30*a*-30*c* embodiments are illustrated showing use of apparatus 10 with a port device. In various embodiments, for doing deep plane dissection or even skin enveloped dissection, apparatus 10 can be configured to be introduced through a surgical port, sheath or other introducing device 30 known in the art. Port 30 can be configured to facilitate access and positioning of apparatus 10 within the tissue pocket 8*dp* at the target tissue site 8. This can be facilitated by fabricating all or portions of port 30 from lubricous biocompatible materials known in the art such as PTFE.

Port 30 can also be configured via its shape 30*s* and size to help initiate or define the dissection pocket 8*dp*. The port opening 30*o* can have a sufficient shape and diameter to allow passage of extender 22 and/or hand piece 15 and an endoscope, suction tube or laproscopic or surgical instrument The opening 30*o* of port device 30 can configured to have an entry diameter 30*d* in the range of 0.25 to 5 inches with specific embodiments of 0.5, 1, 2.5 and 4 inches. Also port opening 30*o* can have a variety of shapes including circular, semicircular, crescent, oval, square, rectangular and the like. In an embodiment, the port opening can include a openings 30*o* including a first port opening 30*o*1 and a second opening 30*o*2. The first opening can be configured for the introduction of a first device such as apparatus 10 and the second opening can be configured for the introduction of a second device such as an endoscope.

Port 30 can also be configured to stabilize unwanted movement of the extender or hand piece in one or more axises. This can be accomplished by selecting the entry diameter 30*d* to be slightly larger (e.g. by several mms) than the extender or hand piece diameter 22*dia* and 15*dia*. It can also be accomplished through selection of the shape of the port opening 30*o*. In an embodiment shown in FIG. 30*c*, port 30 can have a substantially rectangular or slot shaped opening 30*o* having a thickness 30*t* close to that of the extender or hand piece diameter 15*dia* or 22*dia* so as to substantially limit movement of either (and subsequently housing 14) in a direction parallel to the longitudinal axis 301*a* of opening 30*o*.

In other methods embodiments, apparatus 10 can be utilized to perform deep plane dissection for various procedures to create a full thickness subcutaneous flap by dissecting the deep aspect of the subcutaneous tissue (e.g. adipose tissue) from the subjacent muscle fascia. The deeper plane of dissection can be reached using one or more of the three approaches described above. In such embodiments trans-cutaneous markers 21 can be configured or adjusted to a selected height 21*h* sufficient to indicate the proper dissection depth 8*dd* and/or when the desired plane of dissection has, been reached. This depth can be determined by making an incision (at or near the target tissue site) down to the desired tissue layer and then measuring the proper dissection depth. The marker height 21h can then be adjusted accordingly accounting for the height of housing 14. In use, this approach compensates for variations in thickness in one or tissue layers including subcutaneous adipose tissue.

Other surgical method applications for utilizing embodiments apparatus 10 for doing deep plane dissection (e.g. to the facial or deep layers) can include, without limitation, abdominoplasty, buttock lift, thigh lift, subglandular breast augmentation with endoscopic visualization (through the axilla or umbilicus). Extender length 22l, electrode and housing 14 size can be sized to the needs of each procedure. In these and related embodiments apparatus 10 can be used to generate a plane of dissection 8pd by being configured to advance or mow over the muscle fascia or other desired subjacent tissue layer. Accordingly in these and related embodiments, apparatus 10 can include one or more rollers 17 and a pivotable hand piece 15 or extender 22, configured to allow housing 14 or roller to make multiple passes over the selected plane of dissection. Once the surgeon is finished going in one direction he/she can use the hand piece or extender to withdrawal housing 14 back over the selected plane in the opposite direction and make additional passes on the same tissue path or start a new tissue path. In use, this configuration allows the surgeon to go back over the dissection plane as many times as he or she desires to do one or more of the following: (i) smooth out the plane of dissection, (ii) widen the width of dissected skin envelope or other tissue flap; (iii) go back over the dissection plane to coagulate any bleeding tissue or vessels, (iv) deliver additional amounts of heat to the skin envelope or selected tissue flap to titrate the amount of collagen contraction and resultant skin tightening.

Referring now to FIGS. 31a-31c other embodiments provide methods and apparatus to provide a uniform surgical release and mass shifting of overlying soft tissue structures from subjacent tissue structures by uniformly dissecting the overlying structures from the underlying tissue. The uniform surgical release of soft tissue creates a separation interface or uniform plane of surgical dissection which allows for mass shifting of soft tissue in a uniform fashion. A related embodiment also provides a means to surgically shift soft tissue through smaller, less visible incisions 8is. This skin is then shifted to a more aesthetically pleasing location.

In related embodiments, apparatus 10 can also be configured and used to surgically alter or facilitate the surgical alteration of the subjacent soft tissue or tissue structure underlying the skin or the dissected skin envelope.

This can be done using apparatus 10 to dissect and release one or more tissue flaps that lie within or include the soft tissue structure to be modified or portions (e.g. layers) thereof using methods described herein. Such tissue flaps can include without limitation, the dissected skin envelope, cutaneous flaps (the skin and subcutaneous tissue), subcutaneous flaps, fasciocutaneous (the fascia, the subcutaneous layer and the skin) myocutaneous flaps, fascial subcutaneous flap (includes subcutaneous fat layer and the fascia, but not the skin) and myofascial-subcutaneous flaps (these include subcutaneous tissue or portions of it, the fascia and the muscle, but not the skin; subcutaneous means below the skin but above the fascia). The subjacent soft tissue structure can be shifted by plication where a flap is not raised but instead the tissue is tightened by stapling or suturing of adjacent tissue together.

After the flap 8f is released it can then be advanced to the desired attachment site 8a, the redundant tissue is excised and the flap is attached using surgical staples, mooring sutures or other surgical attachment means or procedure known in the art. Alternatively the excised skin need not be removed but can be folded or otherwise hidden within the attachment site depending on its size and shape. In an embodiment, apparatus 10 can be configured to allow such attachment with apparatus 10 in place or it can be removed. For the former case, this can be accomplished by configuring apparatus 10 to allow the passage in the dissection pocket of one or more surgical instruments over or through the apparatus. For example, instruments can be advanced through one or more lumens 24' which can have sufficient diameter for the passage of such instruments including endoscopic or laproscopic surgical instruments known in the art. For deployable embodiments of apparatus/housing 10, apparatus 10 can be put in the non-deployed state (or at least partially) to allow passage of appropriate surgical instruments.

In various method embodiments, apparatus 10 can be used to dissect a tissue flap using an incision and/or attachment site 8is, 8a that is more removed from the target tissue site to be reconstructed than is typical for standard face lift and other flap dissection related surgical procedures. This in turn allows for the incision and/or attachment site to be placed in a location that is hidden or less visible such as the scalp. Further in, apparatus 10 can also allow for the incision site to be much smaller and less obtrusive than current facelift and other flap dissection related surgical procedures.

In various method embodiments, apparatus 10 can be configured to dissect a tissue flap or skin envelope than can be re-attached via the use of mooring sutures. More specifically, mooring sutures can be used to moor or secure the dissected skin envelope down to the subjacent soft tissue structure with or without skin excision. Sutures are placed on the deep surface of the dissected skin envelope to secure or moor the advanced skin envelope to the deeper structures. The mooring suture is placed in the deep surface/or deeper aspects of the dissected skin envelope and secured down to the deeper structures. The sutures are placed just proximal to point of redundancy in the dissected skin envelope to hold it down in place at the point. This procedure serves to maintain the level of surgical advancement of the skin envelope or tissue flap and thus the aesthetic correction or new shape of the skin.

Turning now to a further discussion of housing 14 and with reference to FIGS. 2-5 and 32-33, in various embodiments, housing 14 can be fabricated from any number of medical polymers known in the art such as thermoset, or moldable polymers such as ABS, acrylic, polycarbonate and the like and other medical polymers known in the art. Also all or portions of housing 14 can also be made from materials having high dielectric strength and thermal resistance such as Ultem® 1000, available from the General Electric Corporation. Also housing 14 can be disposable and can include a tissue contact layer or surface 16 which can include one or more fluid distribution ports 33. Surface 16 can also be fabricated from material that is both thermally resistant and has a high dielectric strength. Surface 16 can also be configured to substantially atraumatic and can be made from biocompatible biomaterials known in the art.

Also in an embodiment all, or portions, of housing 14, including tissue surface 16 can have a coating 14c which can be an insulative coating 14ic, an electrical conductive coating 14ec, a lubricous coatings 14lc or a thermally reflective coating 14trc. These and other coatings can be applied using dip coating, spray coating, electro-deposition, plasma coating, lithographic and other coating methods known in the art.

For purposes of this application, an insulative coating is defined to be both an electrical and a thermal insulative coating. In an embodiment, housing 14 has an insulative coating 14ic that insulates against the transmission of RF energy.

Coating 14*ic* can be made from electrically and thermally insulative polymers known in the art including, but not limited to, TEFLON®, PTFE and other fluorocarbons known in the art, polyamide, polyamide and copolymers thereof. Such coatings can range in thickness 14*ct* from 0.0001 to 0.1 inches, which in an embodiment can be 0.001 to 0.003 inches In a related embodiment, coating 14*c* can be a non-stick or lubricous coating 14*lc* configured to keep surface 16 (or other portion of housing 14) from sticking to tissue in the dissection plane 8*p* or the skin envelope 8*se* before during or after, RF energy delivery (e.g. cutting) and/or advancement of housing 14. Such coatings can include PARALENE, PTFE, TEFLON® and other fluoro-carbon polymers, silicones, and other low surface tension non-stick coatings known in the art.

In still other embodiments coating 14*c* can be a patterned coating 14*pc* configured to increase the coefficient of friction with tissue layer 81 in one or more directions. In particular embodiments patterned coating 14*pc* can be a directionally biased pattern coating configured to increase the coefficient of friction in one direction and serve to stabilize or limit the movement of housing 14 in that direction. In an embodiment shown in FIG. 32, coating 14*pc* can be a direction pattern coating 14*dpc* configured to have an increased coefficient of friction with respect to the lateral axis 14*lata* of housing 14 (i.e. a lateral friction bias) but still permit free movement in the longitudinal direction. Coatings 14*dpc* configured in this manner provide a lateral stabilization function, that is they serves to stabilize or reduce side to side movement of housing 14 during movement of housing 14 over or through tissue. Further such coating 14*dpc* can also be configured on housing 14 to provide a lateral stabilization function to the developing skin envelope 8*se* to facilitate its sliding over housing 14 in a longitudinal direction with reduced or minimal lateral movement of the envelope. This can be accomplished by having directional coating 14*dpc* on top portions 14*t* of housing 14. Coating or pattern 14*pc* can also be configured to be substantially tissue atraumatic. This can be accomplished through the use of biocompatible materials described herein such as PTFE or silicone.

Figure 33A:
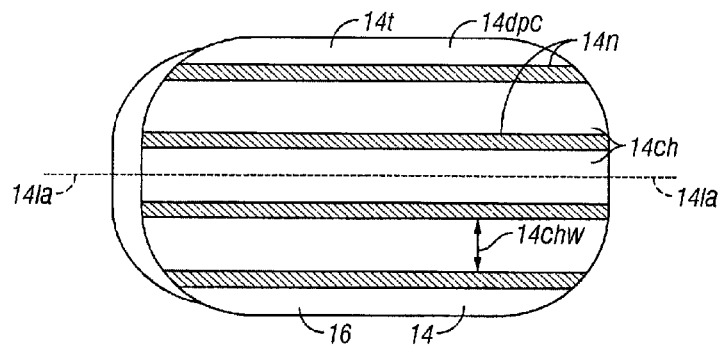
Figure 33B:
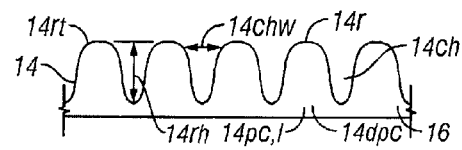

Suitable patterns for a directional coating can include a pattern of ridges 14*r* and channels 14*ch* oriented parallel to the longitudinal axis 14*la* of housing 14 as shown in FIGS. 33*a* and 33*b*. Ridges 14*r* can have a height 14*rh* from 0.001 to 0.025 inches with specific embodiments of 0.002, 0.005, 0.01, 0.05 and 0.1 inches. Also the distance between ridges or channel width 14*chw*, can be 0.0005 to 0.2 inches with specific embodiments of 0.001, 0.002, 0.005, 0.01, 0.05 and 0.1 inches. Suitable pattern coating materials can include polyethylene, HDPE, LDPE, polyurethane, acrylic and silicone. Ridges 14*r* can be formed using hot stamping or polymer molding methods known in the art. Ridges 14*r* can be flexible and can be fabricated from elastomeric polymers such as silicone and other resilient polymers known in the art. Ridges 14*r* can also have a curved tip 14*rt*. Also the channel width 14*chw*, can be sufficient to allow tissue to press into the channels so as to be able to exert a normal force against the longitudinal axis 14*la* of ridges 14*r* and in turn exert an opposing lateral force in response to lateral movement of housing 14. This opposing lateral force can configured to stabilize housing 14 in the lateral direction. In an embodiment, channel width 14*wch* can be 0.0005 to 0.01 inches.

Figure 34E:
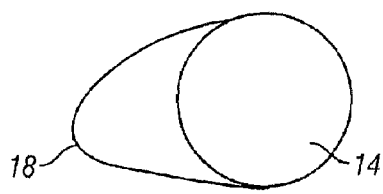
Figure 34E:
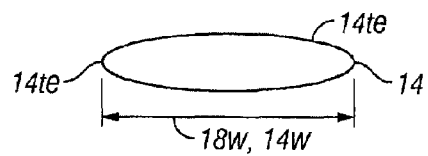
Figure 34E:
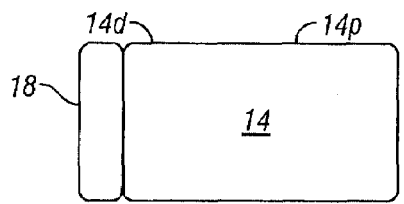
Figure 34E:
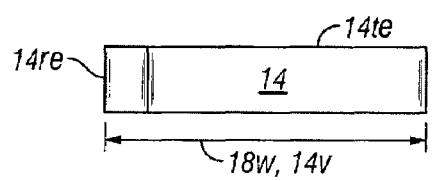
Figure 34E:
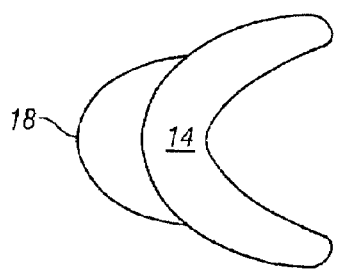

Housing 14 can have a variety of shapes depending upon the medical application or procedure. Referring now to FIGS. 34*a*-34*e*, in various embodiments, housing 14 can be disc, square, rectangular, spherical, semi-spherical shaped or crescent shaped and combinations thereof. In an embodiment, housing 14 can be rectangular shaped having side radiused edges 14*re* and a top raised edge 14*te* which can be radiused or not. Alternatively, housing 14 can be disc shaped again having a radiused perimeter edge 14*re* and one or more raised top edge 14*te* which is substantially straight. In either embodiment, the distance between the two top edges 14*w* can be configured to be greater than the working or cutting width 18*w* of electrode 18. In an embodiment housing 14 width and widths 14*w* and 18*w* can be configured to be provide a buffer space of housing 14 on either end of the electrode. This buffer space can be configured to reduces button-holing or lacerations of the skin envelope as is discussed herein. Another configuration for reducing button-holing is shown in FIG. 34*e* in which the distal end of housing 14 is flared back. In another embodiment 14*w* can substantially equivalent to the working or cutting width 18*w* of electrode 18.

As discussed herein in various embodiments, housing 14 can be adjustable to control a number of dimensional and other parameters relating to the dissection procedure. Referring now to FIG. 35, for example, in an embodiment, housing 14 can be configured to vary the amount that the electrode 18 including cutting edge 18*ce* can be advanced or retracted in an out of housing 14. This can be accomplished using an advancement/locking mechanism 25 known in the art such as a pull wire, cam mechanism, ratchet or gear driven mechanism.

Figure 36B:
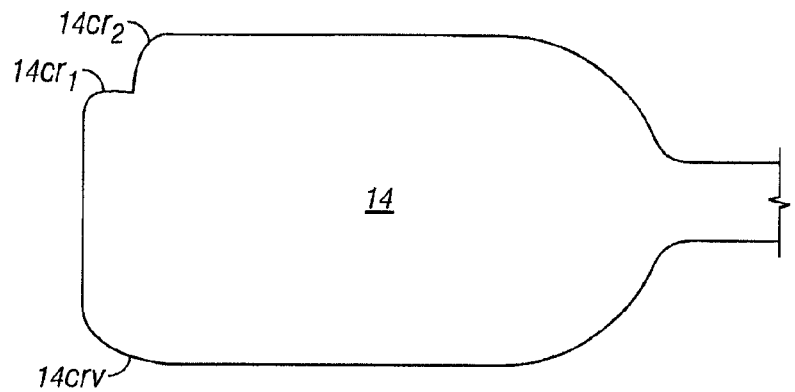
FIGS. 36(a) through 37 illustrate an apparatus of the present invention for dissecting or cutting tissue with a housing that can include one or both of a linear or curved or contoured portions.
Figure 37:
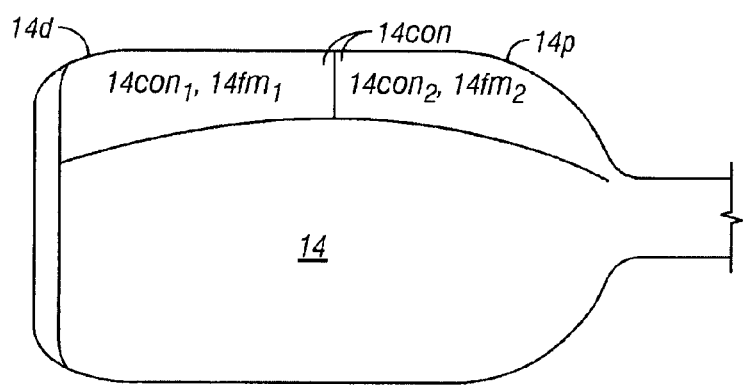
Figure 38:
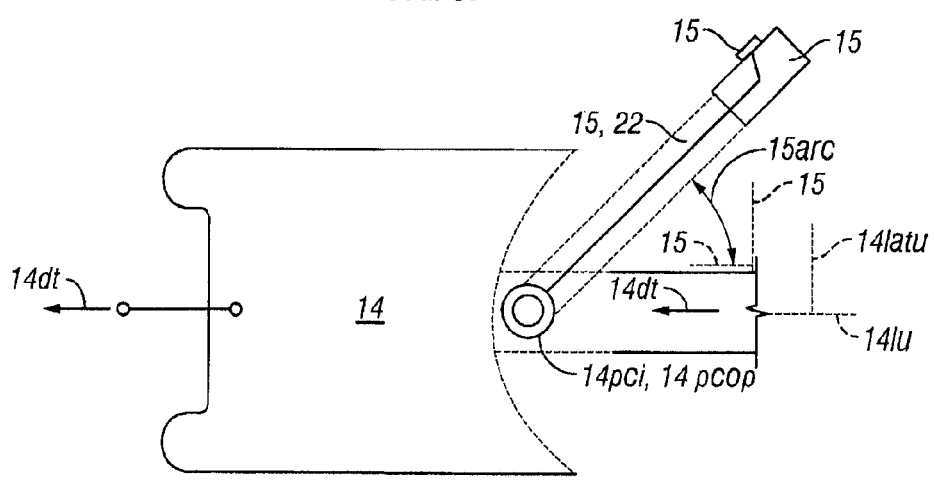
FIG. 38 illustrates an apparatus of the present invention for dissecting or cutting tissue that is configured to move over a curved tissue surface and still maintain a substantially uniform depth of dissection.

Referring now to FIGS. 36*a*, 36*b* and 37, in various embodiments, housing 14 can include one or both of a linear 14*lin* portion or curved or contoured portions 14*cp* as is shown in FIG. 36*a*. The curvature can be selected to substantially match or conform all or in part to the contour 8*c* of a selected tissue site 8.

In various embodiments, the curved portions 14*cp* can be configured to match one or more of the contours of the following anatomical sites: the face, the breast, the buttocks, the abdomen and the like. In an embodiment shown in 36*b*, the curved portion 14*cp* can include only a single radius of curvature, 14*cr*1, a second radius of curvature 14*cr*2, or a varying radius of curvature 14*crv* and combinations thereof.

The amount of curvature of housing 14 can be pre-selected or can shaped by the physician for malleable embodiments of housing 14 described herein. This can accomplished through the use of an articulated housing 14, or a housing 14 made from pliable, malleable and/or conformable polymers known in the art such as silicone rubber or polyurethane and copolymers thereof. In alternative embodiments, it can also be achieved through the use of shape memory metals and associated methods known in the art such as nickel titanium alloys.

Also all or portion of housing 14 can include a conformable portion 14 con made of conformable or malleable materials that are sufficiently flexible to conform to various anatomical contours. Examples of conformable materials include without limitation, silicone rubber, butyl rubber, polyurethane and copolymers thereof. The bending strength or flexural modulus (also known as a bending modulus) of the conformable portion can be selected to conform to the resistive forces offered by one of bone, cartilage, muscle, adipose or a skin layer. Accordingly, in various embodiments, the flexural modulus of conformable portion 14*con* can be selected to be below the bending or compressive modulus of bone, muscle, cartilage, fat or skin all of which are known in biomechanical arts. In various embodiments, the flexural modulus of conformable portion 14*con* can be in the range of 0.001 to 10 GPa with specific embodiment of 0.01, 0.05, 0.1, 0.5, 1 and 5 GPa.

Also in an embodiment shown in FIG. 37, conformable portion 14*con* can a plurality of conformable portions having different flexural moduli include a first portion 14*con*1 having a first flexural modulus 14*fm*1 and second portion 14*con*2 having a second flexural modulus 14*fm*2. In use, embodiments of housings 14 with multiple conformal portions 14*con*, can be configured to allow housing 14 to bend or otherwise conform different amounts for different tissue structures to facilitate movement of housing 14 over curved or irregular shaped anatomical surfaces such as the face having multiple tissue components (e.g. bone and cartilage) with different mechanical properties. This in turn facilitates maintenance of the dissection depth 8*dd* during advancement of housing 14 through or within the dissection pocket 8*dp* or tissues site 8.

In one embodiment of a method of shaping and using a pliable or moldable housing 14, the physician could shape a housing 14 made out of shapable metal such as spring steel by (i) shaping housing 14 by hand, (ii) shaping by pressing housing 14 against the contour of the desired tissue site, or (iii) shaping using a shaping template or tool or even a surgical tool. In another embodiment the medical practitioner could shape housing 14 by sufficiently heating housing 14 to make it pliable (e.g. heat above the glass transition temperature for the material selected) to (i) shape housing 14 by hand, (ii) shape by pressing housing 14 against the contour of the desired tissue site, or (iii) shape using a shaping template or tool or even a surgical tool and then after the shaping was completed cool housing 14 (below the glass transition temperature) to set the shape by quenching in chilled water, ice water, cryogenic gas or other cooling fluid or medium known in the art. The sequence of these steps is exemplary and need not be done in this order. In such embodiments housing 14 could be made of variety of resilient polymers or metals known in the art that have glass transition temperatures above room temperature.

Referring now to FIGS. 2-7, 36-38, apparatus 10 can also be configured to move over a curved tissue surface 8*c* and still maintain a substantially uniform depth of dissection. In an embodiment, this can be accomplished through the use of a movable or pivoting hand piece 15 coupled to housing 14 via a pivotal coupling 14*pcop*. Pivotal coupling 14*pcop* can be any pivoting device or mechanism known in the art including gimbals, ratchet, bearing and cam mechanisms known in the art. In use pivotal coupling 14*pcop* serves to maintain or assist in maintaining the tissue contacting portion of housing 14 in substantially parallel contact (or other selected orientation) with respect to a tissue plane 8*pd* as housing 14 is advanced along a contoured or uneven tissue plane using hand piece 15. This can be achieved for longitudinal, lateral or curvilinear translation of housing 14 along the tissue plane by configuring pivot coupling 14*pcop* to pivot in a longitudinal or lateral axis (or both) with respect to the direction of travel (e.g. advancement) 14*dt* of housing 14. In an shown in embodiments pivot mechanism 14*pcop* can include and indexing mechanism 14*pci* configured to allow the user to select the pivot axis(es) 15*pa* of hand piece 15 such that hand piece only pivots in the selected axis through an arc 15*arc*. Alternatively the mechanism can be configured to allow movement of hand piece 15 in multiple axes.

Figure 39A:
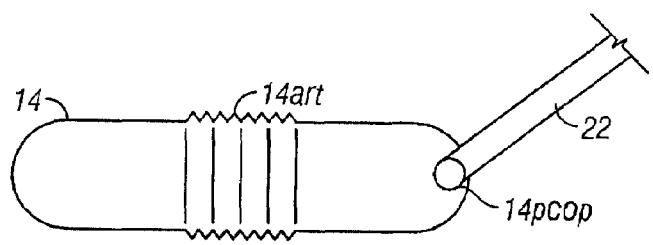
FIGS. 39(a) through 39(c) illustrate an apparatus of the present invention for dissecting or cutting tissue configured to provide advancement of housing on curved surfaces.
Figure 39B:
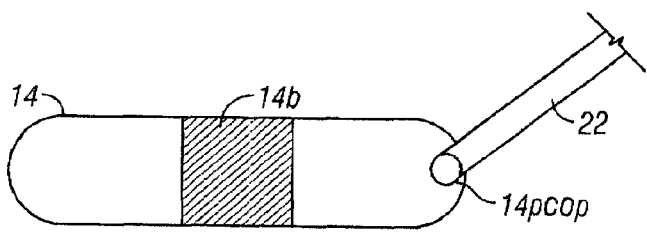
Figure 39C:
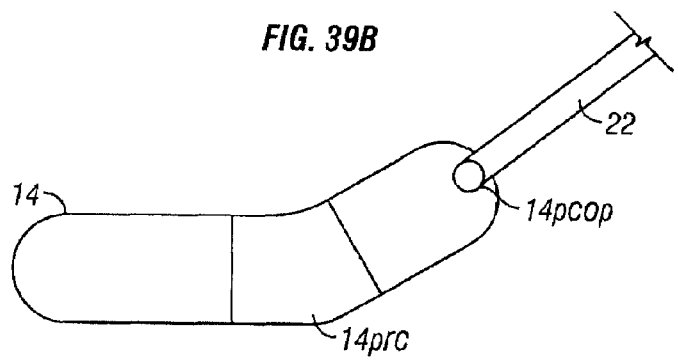
Figure 40:
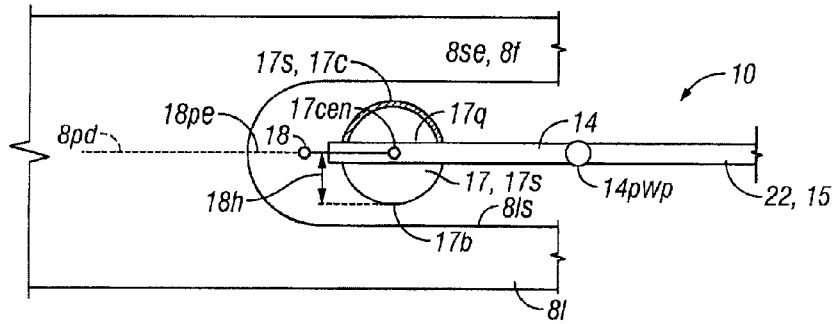
FIGS. 40 through 44 illustrate an apparatus of the present invention for dissecting or cutting tissue with one or more roller devices that can also be a sliding or linear translation device.
Figure 41:
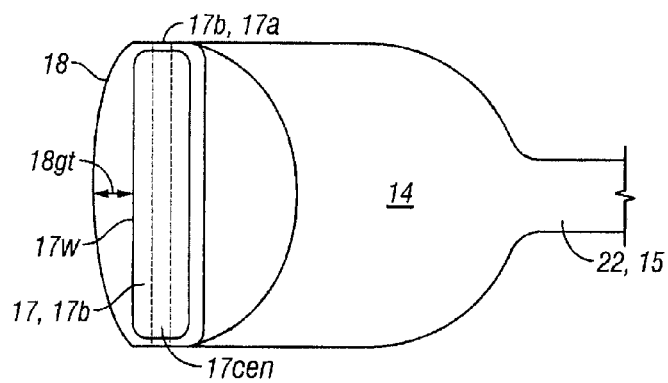

Referring now to FIGS. 39*a*-39*c*, other means for advancing housing 14 on curved surfaces can include housing 14 having an articulated portion 14*art*, a bendable elastic portion 14*b*, or a precurved portion 14*prc*. The bendable portion can be fabricated from bendable elastomers known in the art such as silicone, polyurethane or butyl rubber and the like. The curved portion can have a factory fabricated amount of curvature selected by the physician for the particular tissue site or can be shaped by the physician using procedures described herein.

In one method embodiment of using apparatus 10 to dissect tissue along a curved surface, the physician would select or shape housing 14 to have a degree of curvature corresponding to a tissue contour such as the contour of the fascia over the pectorolis muscle for mastectomy and related procedures. For use of a bendable housing 14 having bendable or articulated portion 14*b* or 14*c*, the physician could press or form fit the curvature of the bendable or articulated portion to match that of the desired contour.

Referring now to FIG. 2-3 and 40-44 in various embodiments, housing 14 can include on or more roller devices, 17 which can also be a sliding or linear translation device 17*s*. Roller or sliding device 17 functions to roll or move housing 14 smoothly along a tissue plane to allow the surgeon to advance housing 14 in a smooth lawn mover like fashion over a tissue plane. Roller device 17 can be configured to roll or glide in a substantially atraumatic fashion along a tissue plane or tissue surface 81*s* such as the subdermal, fascia, subfascia or muscle tissue layers. Also roller device 17 can be configured to substantially maintain the position of electrode 18 with respect to the plane of dissection 8*pd* so as to produce a substantially uniform dissection depth 8DD as the surgeon advances housing 14 over a selected tissue surface at a target tissue site 8.

Embodiments of roller device 17 can comprise one or more rollers movably or rotably coupled to housing 14. In various embodiments, roller device can comprise between 1-20 roller bearings, with specific embodiments of 2, 4, 6, and 10 roller bearings. In an embodiment, the roller can be located behind the electrode with the center of the roller 17*cen* corresponding to the height of the electrode 18*h* (with respect to the roller bottom 17*b*) or otherwise located on the electrode plane 18*pe*. In various embodiments, the gap distance or clearance. 18*gt* between the electrode and the face of the roller 17*w* can be between 0.01 and 1 inch with specific embodiments of 0.05, 0.1, 0.25 and 0.5 inches.

Figure 42:
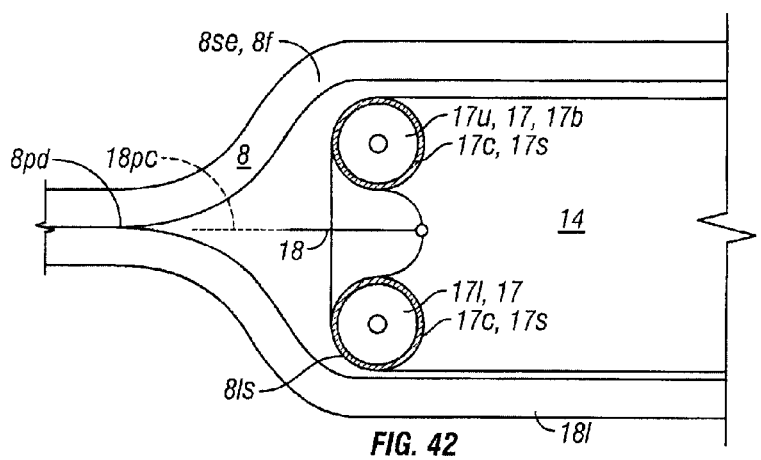
Figure 43:
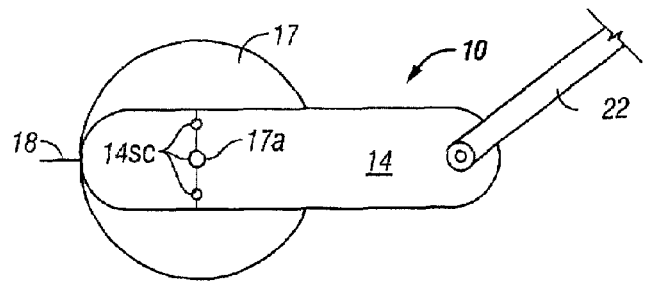

In an embodiment shown in FIG. 42, the rollers 17 can be located above and below the electrode 18 and the corresponding electrode plane 18*pe*. The upper roller 17*u* can be configured to roll or otherwise guide the nascent skin envelope 8*se*, or tissue flap 8*f* over the roller and away from the electrode (e.g. in a proximal direction) and thus protect the skin envelope from further thermal exposure. In performing this function, the upper roller also facilitates maintenance of the uniformity of the thickness 8*t* of the tissue flap 8*f* by doing one or more of the following: reducing the tendency of the nascent skin flap to bunch up, crimp or otherwise come back in contact with the electrode after the first pass and uniformly guide the skin flap away from the electrode after the first pass. The lower roller 17*l* is configured to smoothly advance housing 14 over the selected tissue plane.

Examples of suitable rollers include roller bearings known in the art including needle bearings. Rollers 17 can be fabricated from bearing metals known in the art or polymers such as acrylic, polycarbonate, PTFE or other bearing polymers known in the art. Examples of suitable bearing include those manufactured by the SKF Corporation and the Timken Corporation. In a embodiment shown in FIG. 42, rollers 17 can be movably coupled to housing 14 using a spring coupling mechanism 14*sc* known in the art. Spring coupling mechanism 14*sc* can be configured to perform a stabilizing or shock absorbing function to allow housing 14 to maintain a substantially horizontal and/or parallel alignment with a tissue layer 81 despite roughness or unevenness on tissue layer surface 81*s*. In various embodiments, spring coupling mechanism 14*sc* can include a coiled spring, a leaf spring and other springs known in the art.

Spring mechanism 14sc can be configured to have sufficient spring force to compensate for protuberance or unevenness in the tissue plane and allow housing 14 to maintain a substantially parallel orientation with respect to all or portions of the tissue plane as housing 14 is advanced over the tissue plane. In various embodiments, spring mechanism 14sc can have between about 0.01 and about 1 lb of spring force or more, with specific embodiments of 0.05, 0.1, 0.2, 0.5 and 0.7 lbs of force.

In various embodiments, all or portions of rollers 17 or slide 17s can be thermally or electrically insulative or both. In a particular embodiment, all or portions of rollers 17 or slide 17s can be insulative to RF energy. An example of a suitable thermally and electrically insulative material includes polyetherimide, other materials can include polyimide, polycarbonate and insulative ceramics known in the art.

In other embodiments, device 17 can be include a low friction coating or layer 17c configured to allow housing 14 to slide smoothly along a tissue plane. Coating 17c can include low surface tension coatings configured to have both low coefficients of friction and/or minimize or substantially prevent tissue adhesion to housing 14. Examples of low surface energy materials are described above and can include TEFLON® or other PTFE polymer or copolymer known in the art. Also layer 17c can include surface modification coatings known in the art such those produced using, plasma treatment, vacuum sputtering, chemical vapor deposition, and electro deposition methods known in the art to reduce the surface energy of coating 17c. Also, layer 17c can also be thermally and/or electrically insulative.

Also all or portions of rollers 17 can be fabricated from low surface energy materials to minimize or substantially prevent tissue adhesion to rollers 17 or housing 14. Examples of low surface energy materials or coating include Polytetraflouroethylene (PTFE) available as TEFLON® from the Dupont Corporation, silicone rubber (including RTV and silica free silicon), polyurethane, polyethylene, HDPE, and copolymers thereof known in the art. Coatings 17c can also include surface modification coatings.

In use, roller device 17 can be configured to allow the surgeon to smoothly and atraumatically advance housing 14 over a tissue surface 81s or layer 81 within the dissection pocket 8dp and use electrode 18 to produce a tissue flap having a substantially uniform dissection depth 8dd. Embodiments of apparatus 10 having rollers 17 can be adapted for a number of surgical or minimally invasive surgical procedures including without limitation, plastic surgery procedures such as face lifts, breast lifts, liposuction, eyelifts and the like, dermatological procedures such as biopsies, mole or tissue removal and other surgical procedures such as removal of tissue masses such as lipomas, cysts and the like as well as other procedures described herein.

The dissection depth 8dd can be selected for each procedure and controlled by physician manipulation of housing 14 within the dissection pocket, as well as by selection of the configuration of housing 14, roller device 17 or both.

In various embodiments, different rollers 17 or roller mechanisms can employed for different dissection procedures and tissue locations as needed. Also the number and frictional characteristics of rollers 17 or roller bearing 17b can be varied depending on the procedure. For example, more rollers can be employed for rough or uneven tissue surfaces such as dissection through muscular or fibrous tissue. Similarly, lower friction materials (e.g. PTFE) can employed in such settings or other tissue locations to reduce rolling friction and/or reduce tissue adhesion to the rollers or surface 17s. In various embodiments, the surface energy of the materials in rollers can be less about 50, 40, 30, or 20 dynes/cm.

Figure 44:
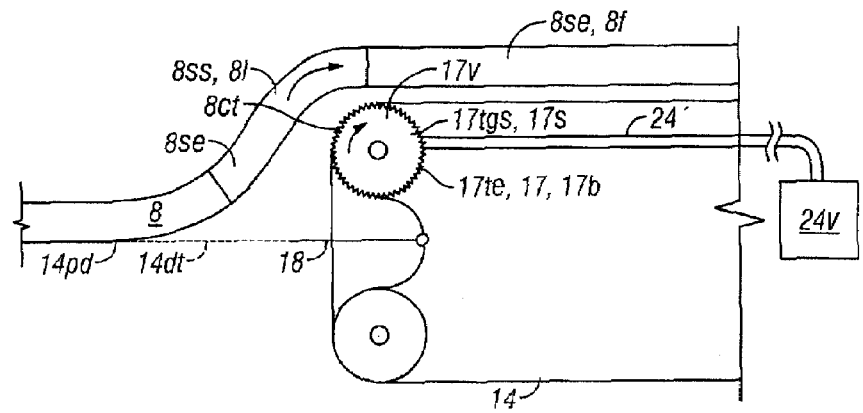

Referring now to FIG. 44, in other embodiments the frictional or material properties of roller 17 or surface 17s can be configured to generate sufficient frictional force with the contacting tissue so as to put all or a portion of the subjacent tissue layers in contact with housing 14 in tension. This can be accomplished by configuring all or portions of roller 17 or surface 17s to have sufficient friction to grip and pull the contacting tissue 8ct in an opposite direction to the direction of travel 14dt of housing 14. This puts the segment of skin 8ss and/or contacting layer 8l between roller 17 or surface 17s and electrode 18 in tension. Thus, roller 17 or surface 17s can be so configured to act as tissue tensioning element 17te via a tissue gripping portions 17tgs.

Means for tensioning by tensioning element 17te or tissue gripping surface 17tgs can include one or more the following configurations: (i) use of a textured surface over all or a portion of roller 17 or surface 17s (ii) use of rubberized otherwise compressible gripping layers over all or a portion of roller 17 or surface 17s, (iii) use of a gripping fiber surface over all or a portion of roller 17 or surface 17s, (iv) use of vacuum ports over all or a portion of roller 17 or surface 17s to adhere the tissue against roller 17 or surface 17s via vacuum pressure, wherein the ports are coupled to a vacuum source 24v via lumens 24'. Examples of texturized surface can include knitted or woven DACRON®, or texturized rubber having a criss-cross, diamond or other pattern known in the art. Also in these and related embodiments higher coefficients of friction of surface 17tgs, by selection of the material properties of roller 17 or 17s including use of materials with higher surface energies.

Higher surface energies can be achieved by vacuum sputtering, CVD, electrodeposition, plasma, chemical etching, shot-peening and other surface modification coating treatments known in the art for plastics or metals. In various embodiments, the surface energy of gripping portion 17tgs can be above 50 dynes/cm, above 80 dynes/cm or above 100 dynes/cm.

Figure 45A:
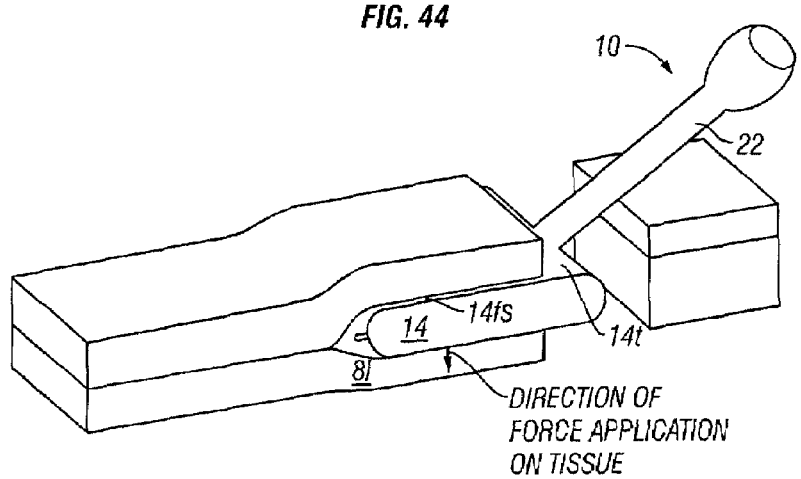
FIGS. 45(a) through 45(b) illustrate an apparatus of the present invention for dissecting or cutting tissue with a housing that provides a force application surface configured to allow the physician to press down on the housing to apply a downward force from the rollers to the underlying tissue layer.
Figure 45B:
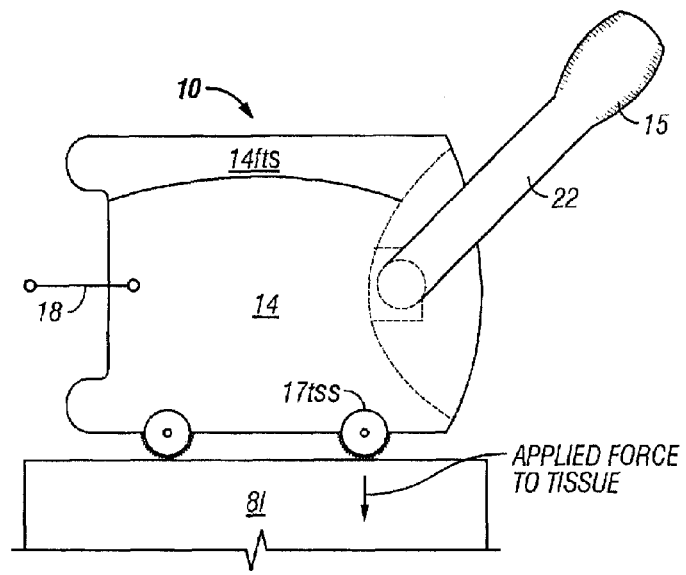

In various embodiments, tensioning element 17te can be configured to maintain tissue layers 81(either or super or subjacent) in between 0.01 and 3 lbs of tension with specific embodiments of 0.1, 0.2, 0.5, 1 and 2 lbs of tension. Tissue tensioning can be facilitated by the application of downward force (e.g. a force normal to tissue layer 8l or dissection plane 8pl) on housing 14. Referring now to FIGS. 45a-45b, this can be accomplished by the physician pressing down on the top portions 14t of housing 14, or use of the downward force from the overlying tissue layers 8l (which may be in a condition of tension as housing 14 is advanced into the tissue plane) or both.

Accordingly, in embodiments shown in FIGS. 45a-45b, housing 14 can have a force application surface 14fs or fixture configured to allow the physician to press down on housing 14 to apply a downward force from rollers 17 to the underlying tissue layer 8l. Force application surface/fixture 14fs can be located on the top or other portion of housing 14 and can also be located on or coupled to hand-piece 15 or extender 22.

In an embodiment, all or portions of housing 14, such as top 14t or bottom 14b, can be configured as a force application surface 14fs. Surface 14fs can be substantially flat, concave, convex and combinations thereof. Force application surface 14fs can be configured to apply a downward force over all or portion of subjacent tissue layer 8l in contact with the bottom of housing 14. In an embodiment shown in FIG. 45b, surface 14*fs* can be configured to substantially only a apply a downward force to tissue gripping surface 17*tgs* and the underlying tissue.

Figure 45C:
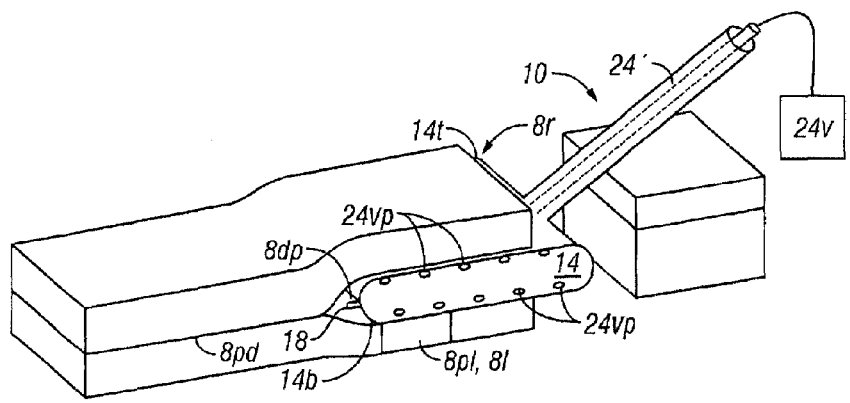
FIG. 45(c) illustrate an apparatus of the present invention for dissecting or cutting tissue with other means for force application.

Referring now to FIG. 45*c*, other means for force application can include use of vacuum ports 24*vp* located on all or portions of housing 14 as is shown in FIG. 45*c*. Vacuum ports 24*vp* can be configured to be coupled to vacuum source 24*v*. The placement and number of ports 24*vp* can be further configured to apply a vacuum force to a selected portions 8*pl* of layers 8*l* to at least partially adhere those layers to all or portions of housing 14 such that when housing 14 is advanced, layers 8*l* are put in tension.

In use, the physician can employ the tensioning element 17*te*, or vacuum ports 24*vp* to put selected portions of a tissue layer in tension before, during or after the application of RF energy to the tissue site. In one method embodiment the physician can use apparatus 10 to pre-stress the selected tissue 81 before the application of RF energy for cutting or skin tightening. This can be accomplished by advancing the front of housing 14 into the developing dissection pocket 8*dp* or incision site 8*is* while maintaining a slight downward pressure on housing 14 to keep the roller in contact with subjacent tissue layers and so generate friction between the roller and subjacent tissue.

Also in use, embodiments having a tensioning element 17*te* can be configured to facilitate the dissection of tissue layers 8*l* at tissue site 8 by keeping the selected tissues layers 8*l* in tension and preventing them from bunching up or otherwise deforming as electrode 18 is advanced through the plane of dissection. This in turn facilitates maintenance of a substantially uniform dissection depth 8*dd*.

Turning now to a discussion of electrode 18 and with reference to FIGS. 2-5 and 46-48, in various embodiments, electrode 18 can be fabricated from a variety of conductive materials known in the art including stainless steel, 304*v* stainless steel, shape memory metals and alloys thereof. Electrode 18 can also have one or more lumens 18*l* for passage of fluids and/or gases for cooling, heating, conduction, irrigation or aspiration. In various embodiments, electrode 18 can have a variety of shapes and geometries including but not limited to a blade or scalpel configuration, ring-like, ball, hemispherical, cylindrical, conical, needle or needle-like.

Figures 46A, 46B:
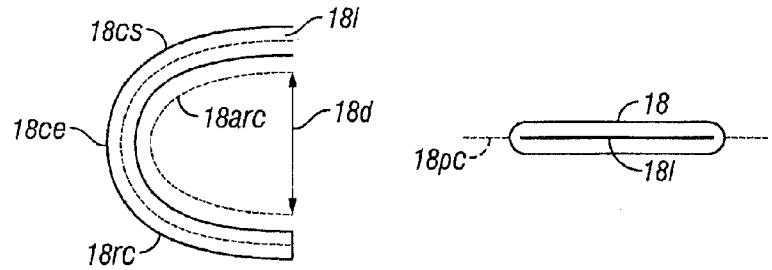
FIGS. 46 through 48 illustrate an apparatus of the present invention for dissecting or cutting tissue with an electrode 18 that is fabricated from a variety of conductive materials.

In an embodiment shown in FIGS. 46*a* and 46*b*, electrode 18 can be made from conductive wire and can be fabricated to have a curved shaped 18*cs* using wire or metal working methods known in the art. Shape 18*cs* can be semicircular, U-shaped, parabolic, or any curve with a selectable amount of arc 18*arc* (e.g. degrees). In an embodiment, shape can 18*cs* can also be configured to be substantially contained or bounded in single plane, also called electrode plane 18*pe*. In other embodiments shape 18*cs* can be in two or more planes.

Also in various embodiments, shape 18*cs* can have a single radius of curvature, 18*rc* or multiple radii of curvature 18*rc*. The diameter 18*d* of curve 18*cs* can be in the range of 0.1 to 5 inches with specific embodiment of 0.25, 0.5. 1, 1.5, 2, 3 and 4 inches. For face lift applications diameter 18*d* can be about 0.4 to about 1 inch and for abdominal and other large tissue sites, such as the abdomen diameter 18*d* can be in the range of about 2 to about 4 inches. Electrode 18 can also be configured to allow the diameter 18*d* to be adjusted by the physician depending upon the tissue site and procedure. This can be accomplished by electrode adjusting means described herein.

In these and related embodiments electrode 18 can be configured to have sufficient strength including bending strength (e.g. bending or flexural modulus) to substantially maintain its curved shape as its through tissue and/or maintain the electrode plane 18*pe*. In an embodiment, the bending modulus is selected to substantially maintain shape 18*cs* as it is advanced through soft tissue such as the skin, adipose tissue, fascia and muscle but to deform upon contact with more rigid tissue such as bone. In other embodiments, electrode 18 can be configured to maintain its shape on contact with skin and adipose tissue but deform upon contact with muscle and/or other harder tissue such as bone, cartilages. In use this selectable deformability of electrode 18 can be configured to provide the physician with tactile feedback of the tissue type that electrode 18 is being advanced into. The bending strength of electrode 18 can be controlled through the selection of one or more of the 18 wire diameter 18*d*, material composition (e.g. alloys) and metal treatment (e.g. annealing, work hardening etc.)

Electrode 18 can be spring-loaded or otherwise have shape memory such that if it is deformed due to tissue-applied forces it will substantially reassume its shape upon removal of the force. In these and related embodiments, where the electrode is configured to have a shape memory it fabricated from spring steels or shape memory materials such as nickel titanium alloys using shape memory processing methods known in the art. In these and related embodiments electrode 18 can have sufficient spring force to substantially maintain its shape as it cuts or dissections through a variety of soft tissues such skin, adipose tissue, fascia and the like. In various embodiments, electrode 18 can be configured to have between 0.1 to 5 lbs of spring force with specific embodiments of 0.2, 0.5, 1 and 2.5 lbs of force.

Figure 47:
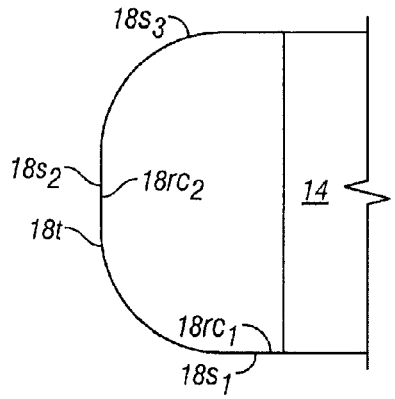

In an embodiment shown in FIG. 47, shape 18*cs* can consist of three sections, a first section 18*s*1, attaching to a first side 14*s*1 or front edge of housing 14, a second section 18*s*2 and a third section 18*s*3 attaching to the other side or front edge of housing 14*s*2, wherein sections 18*s*1, 18*s*2 and 18*s*3 have radii of curvature 18*rc*1, 18*rc*2 and 18*rc*3. In an embodiment, sections 18*rc*1 and 18*rc*3 can be substantially more curved than section 18*rc*2; in another embodiment this configuration can be reversed. Also radii of curvature 18*s*1 and 18*s*3 can be substantially less than 18*s*2. In an embodiment, the electrode 18 can be configured to have camber, which is configured to substantially maintain its shape in response to a selectable amount of normal or other force tending to deform the electrode as the electrode is advanced through tissue.

Figures 48A, 48B:
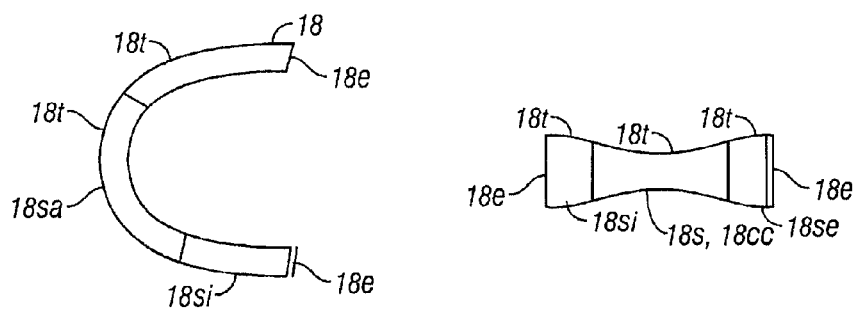

Also, in an embodiment shown in FIGS. 48*a*-48*b*, all or portions of electrode 18 can be tapered portions 18*t*. The taper can be produced using wire grinding and drawing methods known in the art. In one embodiment the tapered portion 18*t* can have a decreasing taper (e.g. decreasing diameter) moving in a direction from section 18*s*1 to 18*s*2. In another embodiment, the taper can be increasing. The taper can be configured to control the rigidity of portions of the electrode, for to provide increased strength or rigidity to side sections 18*rc* 1 and 18*rc*3 by having making those sections have a larger diameter.

The taper can also be configured to vary the electro-cautery cutting characteristics of the electrode. A decreasing taper can be used to increase the current density over selected portions of the electrode, for example section 18*s*2 so as to increase the "cutting current" in that portion. In other embodiments curved electrodes 18 can be configured to have a cutting or sharpened edge 18*ce* on the leading edge of the electrode. Cutting edge 18*ce* facilitates dissection through tissue by acting like a knife-edge as well as increasing the cutting current at the edge.

Figure 49:
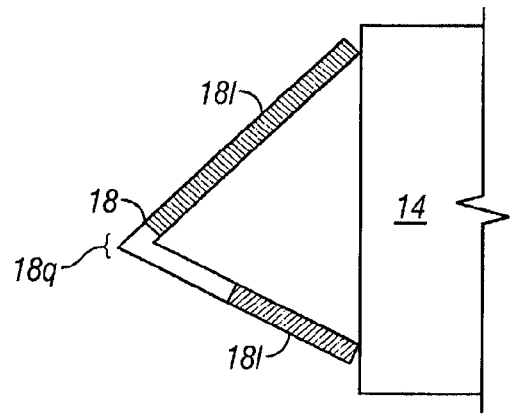
FIG. 49 illustrate an apparatus of the present invention for dissecting or cutting tissue with an electrode that has a wedge shaped or "cow catcher shaped" that provides a wedge or force concentration affect in cutting through the tissue.

Referring now to FIG. 49, in an embodiment shown in FIG. 49, the electrode can be wedge shaped or "cow catcher shaped" to have a wedge or force concentration affect in cutting through the tissue. This shape can be configured to simultaneously cut and undermine or separate tissue layers 8*l* by cutting the tissue at the point or apex 18*a* of the electrode wedge and then force the tissue over wedge. This shape can be particularly useful when starting the beginning of the dissection. Also selected portions of the wedge can have an electrical and/or thermally insulative layer 18*l*. In an embodiment, the point portion 18*a* of the electrode can be conductive and the remainder insulated, this configuration serves to provide a cutting force concentration affect and thermally shield or otherwise minimize heat transfer to the nascent tissue flap in close proximity to the electrode.

Figure 50:
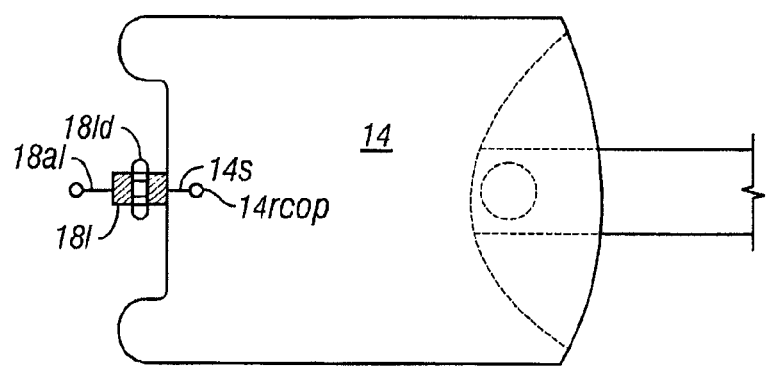
FIG. 50 illustrate an apparatus of the present invention for dissecting or cutting tissue with one or both ends of the electrode attached to the sides of the housing.

Referring now to FIG. 50, one or both ends 18*e* of electrode 18 can be attached to the sides 14*s* of housing 14, either directly or via an insulative coupling 14*icop*. Examples of insulative coupling can ceramics, insulative polymers and other insulators known in the art having a high dielectric strength. In related embodiments insulative coupling can comprise an insulative coating on the electrode portion in proximity to housing 14. Examples of suitable insulative coatings can include, polyimide, polyamide, TEFLON, NYLON PARALENE and other insulative polymers known in the art. In various embodiments, insulative coatings 18*l* can extend a selected length over the electrode and can be slidably movable over the length of the electrode (e.g. by sliding in and out of the interior of housing 14) in order to select a length of active electrode 18*ae*. The coating can be configured to be slid or advanced a fixed length and held in place by virtue of friction between the coating and the electrode or locking device 18*ld* positioned at the juncture between the electrode and housing 14 or insulative coating. Examples of locking devices can include a bolt, screw or clamp known in the art.

Figure 51A:
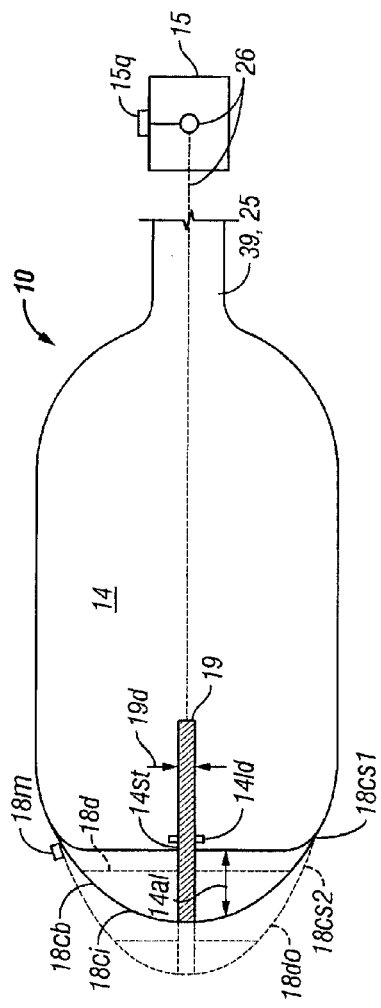
FIGS. 51(a) through 51(b) illustrate an apparatus of the present invention for dissecting or cutting tissue with the electrode coupled to the housing with a strut member.
Figure 51B:
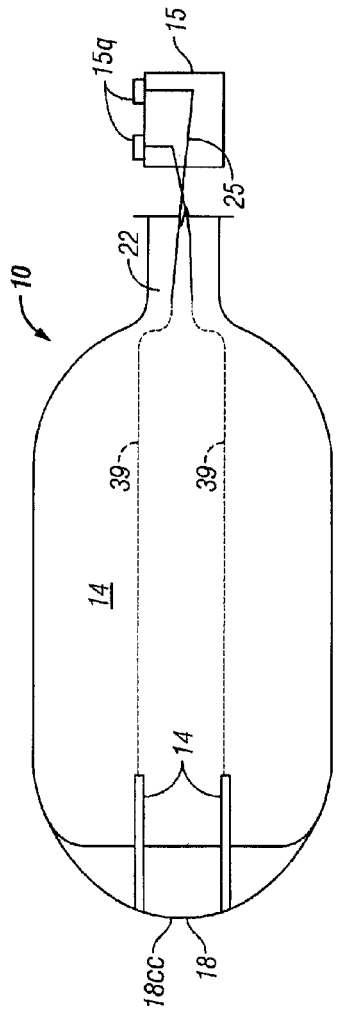

Referring now to FIGS. 51*a* and 51*b*, in various embodiments, electrode 18 can be coupled to housing 14 via a strut member 19. Strut member 19 can be configured to provide sufficient structural support to electrode 18 to substantially maintain the shape of the electrode (e.g. in a U shape) as the electrode is advanced through tissue. In various embodiments, a single strut member 19 can be located at a locus 18*loc* of the center curve of the electrode. In another embodiment, two strut members can be coupled to electrode 18 and can be substantially equidistant from each In or embodiments three or more strut member can employed strut members can be of metals such as steel, 304*v* steel or tool steel, or rigid polymers such as polycarbonate, acrylic, or Nylon. Member 19 can also have sufficient column strength to substantially maintain the shape of electrode 18 in response to forces applied by tissue (e.g. normal forces) tending to deform the shape of the electrode as the electrode is advanced through issues.

In an alternative embodiment, the column strength and position of strut member(s) 19 can be also configured to provide for some flex in the shape or camber of electrode 18. The amount of flex can be configured to provide the surgeon with tactile feedback of the resistance encountered by the electrode as it is advanced through tissue. Further this amount of flex can be configured to allow the surgeon to discriminate between softer tissue such as dermal adipose tissue, less soft tissue such as muscle, vascularized, fibrous and cartilage tissue and rigid tissue such as bone.

In an embodiment, electrode 18 and strut member(s) 19 can be configured to vary the shape of the cutting surface of the electrode 18*ce* in response to tissue applied forces. In another embodiment, electrode 18 and strut member 19 be configured to have electrode 18 deform into a pointed or curved arrow head shape in response to a selectable amount of applied tissue force as the electrode is advanced into tissue. These and related embodiments can be configured to facilitate smoother advancement of the electrode and/or a more uniform width of dissection 8*wd* (also called dissection swath 8*wd*) particularly for tissue non-uniformities (e.g. scar tissue), uneven tissue, or anatomical deformities.

This can be accomplished by having the electrode assume a pointed shape when encountering more resistance from tissue, thus concentrating the current density (due to edge effects) and the cutting or tissue shearing force in the tip or point of the electrode. This biases cutting or dissection in the horizontal center of the plane of dissection and in so doing, facilitates a more even horizontal dissection and reduces the likelihood of the electrode veering out of the selected plane of dissection. Once the more resistive tissue is cut through, the electrode is configured to have sufficient spring force to spring back to its original curved shape or degree of camber.

In these and related embodiments electrode 18 can be fabricated from flexible wire, spring steel or nickel titanium alloys. This can be accomplished by positioning a single strut member 19 in the center or locus 18*loc* of curved electrode 18 and can configuring the electrode to have sufficient elasticity to deform inwardly in one of a curved, a convex curved, inward parabolic curved, or hyperbolic curved manner in response to a selected amount of force.

In an another embodiment, member 19 can be advancable in and out of housing 14 in order to change the advanced length 19*al* of the strut member. This can be accomplished by virtue of slot 14*st* in housing 14 and a locking device 14*ld*, such as a locking screw, or bolt positioned at the slot opening 14*st* in housing 14. Embodiments having an advancable strut member 19 can be configured to change the shape and overall dimensions of the electrode. More specifically the amount of curvature 18*cs* of the electrode can be varied as well as the diameter 18*d*, for example from a first curvature and diameter 18*cs*1, 18*d*1 to a second curvature and diameter 18*cs*2, 18*d*2.

Housing 14 can also have slots 14*so* for advancement and retraction of the electrode as well in and out of housing 14 as well as an associated locking mechanisms. Other electrode adjusting means can include an actuation member 15*am* such as pull wires and the like coupled directly or indirectly to the electrode.

In use, an advancable member 19 can allow the physician to change the shape so as to in turn vary one or more of the electro-cautery, cutting or dissection characteristics of electrode to meet the needs of the a selected tissue site and tissue type. For example member 19 can be extended to produce a more oblong shape for tougher more fibrous tissue and retracted to produce a flatter curve for softer tissue. Embodiments of apparatus 10 having an extendable electrode can also be configured to vary the amount of tension in electrode 18 and hence the stiffness of the electrode as well. By extending member 19, the tension in electrode 19 can be increased making the electrode stiffer (e.g. less deformable) and better able to hold its shape in response to tissue-applied forces. Similarly electrode 18, the electrode can be made more flexible by the shortening or withdrawal of member 19 back into housing 14.

In another embodiment member 19 can be configured to be reciprocating in and out housing 14 to during the dissection procedure and facilitate cutting or dissection by acting in a jackhammer like fashion. This can be accomplished by coupling member 19 to a reciprocating mechanism known in the art, which can include a pneumatic mechanism coupled to a pneumatic pressure source.

The column strength of member 19 can be manipulated by selection of the diameter and material strength (e.g. compressive modulus) for member 19. The diameter 19*d* of member 19 can be in the range of 0.005 to 0.3 inches with specific embodiments of 0.05, 0.1, 0.2 inches. Also the column strength of the strut member can be in the range of 0.1 to 10 lbs, with specific embodiments of 0.5, 1, 2, 5 and 7.5 lbs. Strut members 19 can be made from insulative material or can be coating with an electrically insulative coating 19$l$ described herein.

Electrode 18 can be made of a variety of conductive materials, both metallic and non-metallic. Suitable materials for electrode 18 include, steel such as 304 stainless steel of hypodermic quality, platinum, gold, silver and alloys and combinations thereof. Also, electrode 18 can be made of conductive solid or hollow straight wires of various shapes such as round, flat, triangular, rectangular, hexagonal, elliptical and the like. In a specific embodiment all or portions of electrodes 18 can be made of a shaped memory metal, such as NiTi, commercially available from Raychem Corporation, Menlo Park, Calif. A radiopaque or echogenic marker 18$m$ can be coated on electrodes 18 for visualization purposes using x-ray, ultrasound and other medical imaging methods known in the art. Marker 18$m$ can be made from radio-opaque and/or echogenic materials known in the art.

In various embodiments, energy delivery device 18 and power source 20 can be configured to operate within the following parameters: (i) provide a controlled delivery of electromagnetic energy to the skin surface that does not exceed, 1,000 joules/cm2, or 500 joules/sec/cm2; (ii) provide a controlled delivery of electromagnetic energy to the skin surface not exceeding 2000 joules/cm2 during a single treatment session (during a twenty-four hour period); provides a controlled delivery of electromagnetic energy to the skin surface not exceeding 200 joules/cm2 during a single treatment session, or not exceeding 10 joules/sec/cm2; (iii) operate in an impedance range at the skin surface of, 70 ohms cm2 (measured at a frequency of 88 Hz) to 40 Kohms cm2 (measured at a frequency of 10 KHz); (iv) provides a controlled delivery of electromagnetic energy to operate in a range of skin thermal conductivities (at or near the skin surface) of 0.20 to 1.2 k (where k=1*[W/(m° C.)]); and (v) operate in a range of compression forces applied to the skin surface and/or the underlying soft tissue anatomical structure not exceeding 400 mmHg, not exceeding 300 mm, not exceeding 200 mmHg or not exceeding 100 mmHg.

Suitable energy sources 20 that may be employed in one or more embodiments of the invention include, but are not limited to, the following: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz, (xii) a microwave source or (xiii) a fluid jet.

Figure 52:
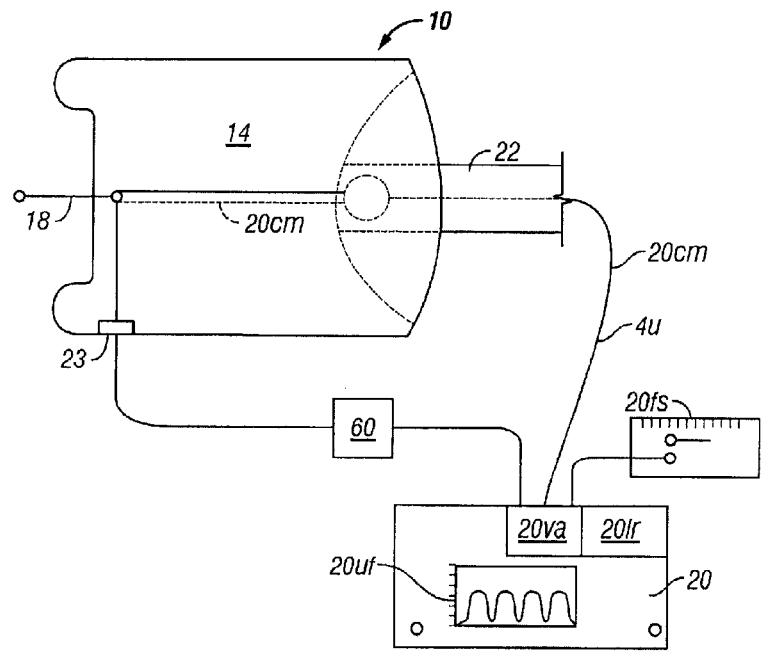
FIG. 52 illustrate an apparatus of the present invention for dissecting or cutting tissue with an electrode that is electromagnetically coupled to an energy source.

For ease of discussion, the energy delivery device 18 is one or more RF electrodes 18 and the power source utilized is an RF power supply. However, all other energy delivery devices and power sources are equally applicable. Referring now to FIG. 52, electrode(s) 18 are electromagnetically coupled to energy source 20. The coupling can be direct from energy source 20 to each electrode 18 respectively, or indirectly by using connector member 20$cm$ such as a collet, sleeve, connector, cable, cord 40$w$, and the like which couple electrodes 18 to energy source 20. Electrodes 18 can also be multiplexed to power source 20 through a multiplexing device 20$m$ and associated multiplexing methods known in the art.

In various embodiments, RF power source 20 and electrode 18 can be configured to deliver RF energy in one of a monopolar mode or a bipolar mode, as is known in the art. Further RF power source can be configured to switch or toggle back and forth between monopolar and bipolar mode on operator command or via control system 60. In various embodiment RF electrode 18 and power source 20 can be configured to delivery RF energy to perform one or more surgical procedures including without limitation cutting, coagulation, ablation and combinations thereof. Accordingly, power source 20 can be configured to generate RF energy in one or more procedural modes known in the electro-surgical arts including without limitation, cut mode, coagulation mode and blended mode. In each of these modes RF generator 20 can be configured to generate a waveform 2$xw$A that has specific shape, frequency, voltage and current properties to produce selected tissue effects. Again generator 20 can be configured to switch back and forth among these or other electro-surgical modes known in the art. This switching can be automatically controlled by logic resources 20$lr$, or a control system integral or coupled to generator 20 or manually by the surgeon, (e.g. using a foot switch 20$fs$) or both.

In the cut mode, energy (current) is delivered continuously delivery with a waveform having an undamped sinusoidal shape. The intracellular fluid in the targeted tissue heats to the vaporization state causing cells in the affected tissue to explode which disrupts/destroys the structure of the affected tissue.

Coagulation mode is characterized by a discontinuous waveform that consists of a dampened cut wave that is duty cycled (e.g. has an on time then an off time) and has higher voltages than a cut waveform. The off time allows cell to cool between heating which in turn allows for the formation of a coagulum and providing a high degree of hemostasis. The blended mode can have a waveform that combines features of the cut and coagulation waveform allowing for an RF current that cuts with varying degrees of hemostasis. The blended wave has an increased duty (e.g. more on time) and lower voltages than a coagulation wave form but higher voltage than a pure cut waveform. Increased levels of coagulation can be obtained by lowering the duty cycle and vice versa. Example blended wave forms can have duty cycles that include but are not limited to the following on off ratios: 50% on 50% off; 40% on 60% off; and 25% on 75% off.

Apparatus 10 can be configured to operate with numerous conventional, commercially available, electro-surgical energy generators.

An example of a suitable electro-surgical or RF energy generator 20 can include a unitary mono-polar-bipolar RF generator, such as the Valleylab "FORCE 2" RF Generator manufactured by Valleylab, a division of Tyco Healthcare Group LP, 5920 Longbow Drive, Boulder, Colo., 80301-2199, U.S.A. Apparatus 10 can be coupled to power source 20 using a conventional power cord 40, which may be long (for example, over two meters) and connect directly to electrosurgical energy generator 20 via standardized, monopolar or bipolar connectors, which are well-known in the art. Power cord 40 may also be short (less than one third of a meter, for example) and have a standardized, conventional monopolar or bipolar connection (also well-known in the art) to another, longer power cord, which is normally reusable and available with electro-surgical energy generator 20. An operator uses a foot-activated switch of electro-surgical energy generator 20 to supply energy through instrument 20 to the electrode 18 and the tissue being treated. The operator can adjusts one or more power settings on electrosurgical energy generator 20, such as the wave form, maximum power setting to be in a sufficiently effective range (e.g. 10 to 100 watts) depending upon the type of tissue to be dissected (e.g. the skin envelope v.s. the fascial layer), size of the dissection path, and amount of skin tightening desired. The foot switch may also have a multi-pedal design to allow the operator to both initiate the delivery of RF energy as well switch between RF wave forms (e.g. thus for cut, versus coagulation or collagen tightening.

In another embodiment, apparatus 10 can be configured to use high frequency high power RF energy and thus can be configured to be coupled to high power high frequency electro-surgical energy generator. In these and related embodiments apparatus 10 can be configured to utilize RF energy having a frequency range of about 1 to about 15 MHz with specific embodiments of 2.5, 3.5, 10 and 14 MHz; voltage up to about 700 volts rms, a current up to about 2 amps and a delivered power up to about 500 or up to about 1000 watts. The delivered power can be pulsed or continuous, with peak pulsed power capable of exceeding 1000 watts. Further description of high frequency, high power RF generators and their use in electro-cautery and other RF medical procedures is found in PCT application No. PCT/US01/149207 (Publication No. WO 02/053048) and U.S. patent application Ser. No. 09/752,978 which are fully incorporated by reference herein.

Figure 53A:
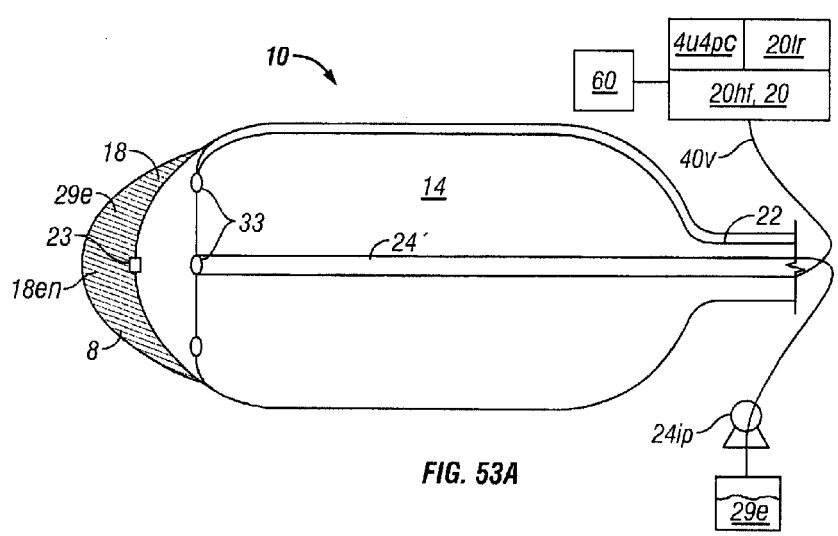
FIGS. 53(a) and 53(b) illustrate an apparatus of the present invention for dissecting or cutting tissue configured to use high frequency, high power RF energy in conjunction with injection or infusion of an electro-conductive or electrolytic solution.
Figure 53B:
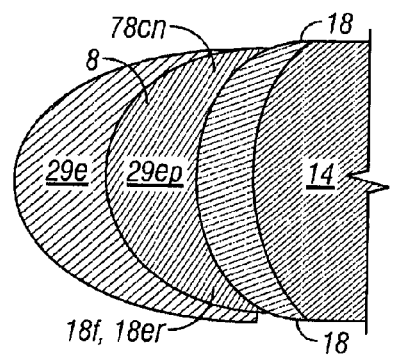
Figure 54:
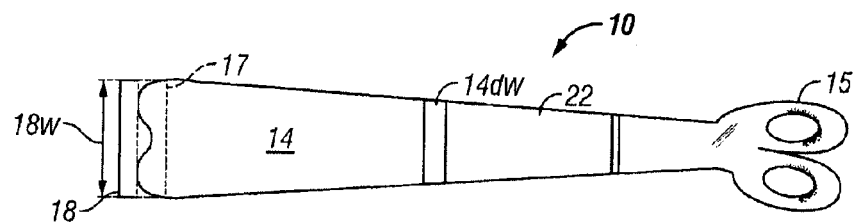
Figure 55:
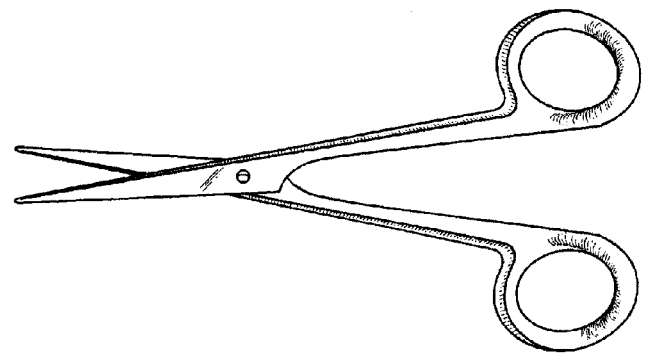

Referring now to FIGS. 53*a* and 53*b* in related embodiments apparatus 10 can be configured to use high frequency high power RF energy in conjunction with injection or infusion of an electro-conductive or electrolytic solution 29*e* at the tissue site to create an enhanced or tumescent electrode 18*en*. Enhanced electrode is created by the delivery of sufficient RF power to increase the current density in the electro-conductive fluid surrounding or adjacent electrode 18 to the point where that fluid acts as an electro-cautery electrode or energy delivery device to cut, ablate, vaporize or coagulate tissue in contact with or proximate to the enhanced electrode.

In various embodiments, electro-conductive solution 29*e* can include various saline solutions known in the medical arts including, buffered saline solutions, 0.9% saline solutions and carrier saline solutions such as tumescent saline carrier solutions infused as part of a liposuction procedure (containing epinephrine and anesthetic such as lidocaine) or saline carrier solution used for injection of local anesthetics such as lidocaine as part of face lift and other plastic surgery procedures using localized injection of an anesthetic. Additionally, the solutions (saline or non-saline solutions) containing lidocaine and/or its chemical derivatives can also be used as electro-conductive solutions by virtue of the electro-conductivity of lidocaine which is itself electro-conductive in solution.

In an embodiment of a method of using high power/high frequency RF energy for flap dissection, the surgeon would pre-infuse the target tissue site with tumescent saline solution, a saline-based anesthetic solution or other saline or electro-conductive solution 29*e*. The amount of infused saline can vary depending upon the procedure from 0.001 to 5 liters, with specific embodiment of 0.005, 0.1, 0.5, 1 and 2.5 liters. For liposuction the infused volume can be between 0.5 to 4 liters, for face lift procedures it can be between 0.05 to 0.5 liters.

An incision would be made and the apparatus 10 placed within the incision with subsequent saline infusion or injection as needed. Electrode 18 would then be energized by high frequency power source 20*hf* with the power levels and frequencies adjusted manually or automatically to produce enhanced electrode 18*en*. After energizing the electrode and generating the enhanced electrode, the surgeon would then advance apparatus 10 within the tissue pocket and use the enhanced electrode 18*en* to dissect one or more selected tissue flaps. (Alternatively the surgeon could start the dissection procedure with electrode 18 configured as a normal RF electrode and convert to enhanced electrode 18*en* via manual command or automatic control of power source 20 or control system 60).

Additional saline infusion or injection could be made as needed and could be done so responsive to monitored impedance and/or temperature levels at the tissue site using impedance and/or temperature sensors including the electrode. The infusions/injection could be done under manual control using an infusion pump 24*ip* or could be controlled using a control system described herein. In an embodiment, continuous, duty cycled or intermittent infusion could be done throughout the period of RF energy delivery.

To facilitate use of the above and related methods using an enhanced electrode for more commonly performed plastic surgery procedures that utilize saline infusion or injection such as liposuction, face lifts and the like, in various embodiments, power source 20 can be configured to allow the surgeon to enter the type of infusion/injection solution used including the saline and/or other solute concentration. The power source 20 could then use a power control algorithm or computer program 404*pc* to adjust the RF power levels (e.g. voltage and current) and frequencies based on the electro-conductivity and/or solute concentrations of the infused solution 29*e* to produce the desired enhanced electrode or enhanced electrode effect (e.g. increased tissue temperatures, etc.). Program 404*pc* could be resident within processor that is part of power source 20 or could be resident within a processor that is part of control system 60 that is coupled or integral to power source 20.

Enhanced electrode 18*en* comprises both the original metal or wire electrode 18 and charged or electrically energized fluid 29*ef* surrounding the electrode, known as the fluidic component 18*f*. In various embodiments, enhanced electrode 18*en* can also be configured to generate higher tissue temperatures than standard RF electrode and thus provide an enhanced electro-cautery cutting and ablation effect. This is due to the fact that: (i) the use of the infusion solution with the enhanced electrode reduces or prevents the buildup of charred matter on a wire or metal electrode 18 which can cause a shut down of the generator due to the development of excessive impedance and (ii) the fluidic component 18*f* of the enhanced electrode is itself not subject to the buildup of charred matter.

These two factors singularly or combined allow for greater amounts of current and hence power to be delivered to the enhanced electrode resulting in higher temperatures (due to Ohm's law) at the electrode and surrounding tissue.

In an embodiment, the delivered power levels to create an enhanced electrode 18*en* can be about 500 watts or greater at a frequency of about 1 MHz or greater. The size and/or shape of the enhanced electrode can be controlled or modulated by control of one or more of the frequency, power, voltage or current of the RF signal from RF generator. The size of the enhanced electrode can be increased by increasing the RF power, frequency or both. Increasing of one or both of these parameters also serves to increase the electrodes tissue cutting, dissection and ablation and abilities by producing higher current densities and thus higher electrode/tissue temperatures which vaporize, cut or ablate contacting tissue faster and more thoroughly. In various embodiments, enhanced electrode 18en can have the same basic shape or proportions as electrode 18 only larger depending upon the delivered power. Alternatively the enhanced electrode can be a different shape such as spherical, cylindrical depending upon the distribution of the electrolytic fluid 29e and RF parameters.

Thus embodiments of the invention utilizing an enhanced electrode can be configured to allow or facilitate faster more uniform tissue flap dissections by virtue of one or more of the increased temperature, size and electro-cautery properties of the enhanced electrode.

Figure 3:
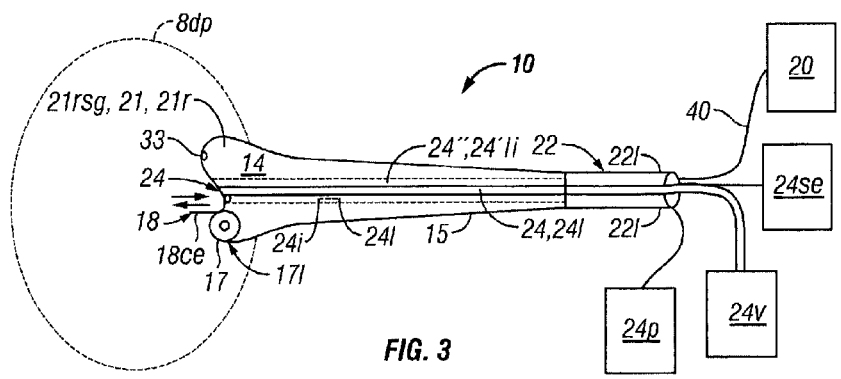
FIG. 3 is a cross-sectional view of an apparatus of the present invention for dissecting or cutting tissue that includes suction capability.

Turning now to a discussion of extenders 22 and referring to FIG. 3, in various embodiments, extenders 22 can be attached to the electrode housing 14 and/or hand piece 15. Extenders 22 can also be of variable length. This can be achieved by configuring extenders 22 to be telescoping or otherwise having a slidable extension mechanism known in the art. In an embodiment, this can be accomplished through telescoping sections 22t which are coaxial and/or swaged or are otherwise attached together. Extenders 22 can be made from thermoset, thermoplastic or moldable polymers known in the art such as ABS, acrylic, polystyrene, polyetherimide and the like. Extenders 22 can also be made from metal such as steel, 304v steel or tool steel and can be coated with a thermally and/or electrically insulative layer 22l. Alternatively, all or portions of extenders 22 can be fabricated from superelastic metals known in the art Referring now to FIGS. 2 and 3, in an embodiment, apparatus 10 can be configured to have a suction capability via a suction device 24 which can include a suction lumen or port 24' running through all or a portion of apparatus 10. This can include portions of housing 14 and/or the extender 22. Suction device 24 can be configured to be coupled to a vacuum source known 24v in the art. Suction device 24 can also be configured to have sufficient suction to suction off steam, water vapor or gases created during use of apparatus 10 in an electro-surgical procedure. Suction can be configured to minimize thermal damage from steam created in a closed system during use of the device. Also suction can be incorporated into apparatus 10 (via suction device 24 other suction means known in the art) as a means of convection cooling of the dissection pocket 8dp created during use of apparatus 10. In an embodiment, suction device 24 can configured to provide between 1 and 760 torr of vacuum. Also all or portions of suction device 24 can be made from heat resistant polymers known in the art such as polyetherimides, polyethers, polyesters, polyamides, polyimides and polybenzoxazole. An example of suitable heat resistant polymer includes Ultem®, available from the General Electric Corporation. Suction device 24 can also be an aspiration device known in the art and in an embodiment, can be the same aspiration device used to perform the liposuction. In an embodiment, suction device 24 or ports 24' can be coupled to a smoke evacuation device 24se known in the electro-surgical arts.

In related embodiments suction device 24 can also be configured as insufflation device 24i to allow the surgeon to insufflate all or portions of the tissue site 8 including the dissection pocket 8dp and the skin envelope 8se. In use insufflation can allow the surgeon to observe the developing plane of dissection 8pd and adjacent tissue either directly or using an endoscope or other viewing device known in the art. Insufflation device 24i can be configured to be coupled to a pressure source 24p such as compressed air source known in the medical arts.

In various embodiments, apparatus 10 can be configured for endoscopic viewing capability or to be used in conjunction with an endoscope. This can be achieved through use of an endoscopic or viewing device 24e that is integral to or movably positionable within apparatus 10 or used as separate adjunct device. In various embodiments, endoscopy can also be performed through lumen 24' or another lumen 24" which can each be configured to allow the passage of an endoscopic device, viewing scope and the like. In an embodiment, apparatus 10 and/or endoscopy device 24e, or an adjunct endoscopy device can be configured to allow endoscopic visualization of subcutaneous tissue sites in the operating site including the subcutaneous plane of dissection. These and related embodiments can be configured to be utilized during electro-cautery procedures such as electro-cautery hemostasis to allow the surgeon to view all or a portion of the subcutaneous plane of dissection to ascertain hemostasis and other tissue conditions. Alternatively, a suction assisted lipectomy canula or lumen 24'lc can also be employed.

Figure 56:
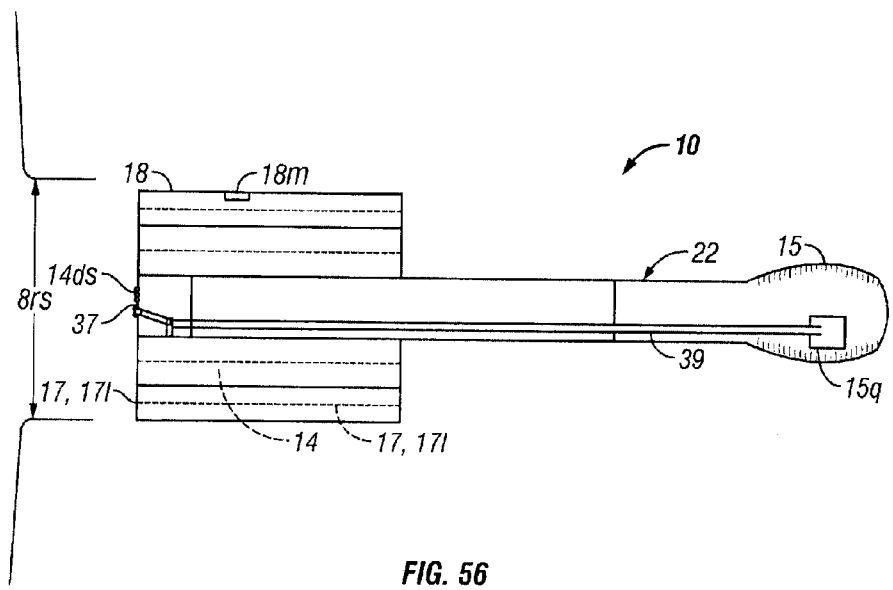
FIGS. 56 through 57 illustrate an apparatus of the present invention for dissecting or cutting tissue with a hand piece configured to be attached to the electrode housing to provide similar tactile sensation.
Figure 57:
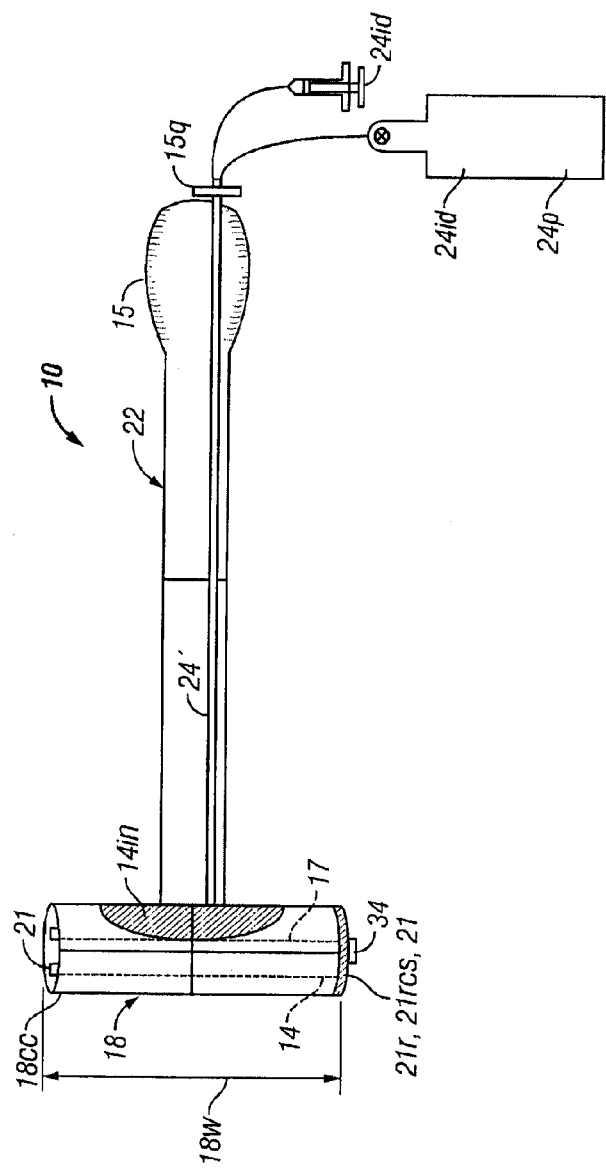

Referring now to FIGS. 56-57, in an embodiment, hand piece 15 can be configured to attached to the electrode housing 14 and can be configured to provide similar tactile sensation (e.g. feel and visual appearance) as standard surgical instruments such as a Metzenbaum scissors (see FIG. 3). This can be accomplished by having hand piece 15 have a similar grip as Metzenbaum scissors and/or similar mechanical properties. Hand piece 15 can also be configured to attach to a disposable housing 14 and can include a quick detach mechanism 14dm described herein or known in the art. In use, detach mechanism 14dm can be configured to allow the physician to rapidly detach and replace housing 14 the same or different housing (e.g. having a different height or electrode shape) depending upon the requirements of the procedure. In one embodiment the physician could detach housing 14 when switching from an dissection procedure to an excision procedure or when switching from performing a procedure on a subcutaneous flap to a myocutaneous flap and vice a versa.

Figure 58:
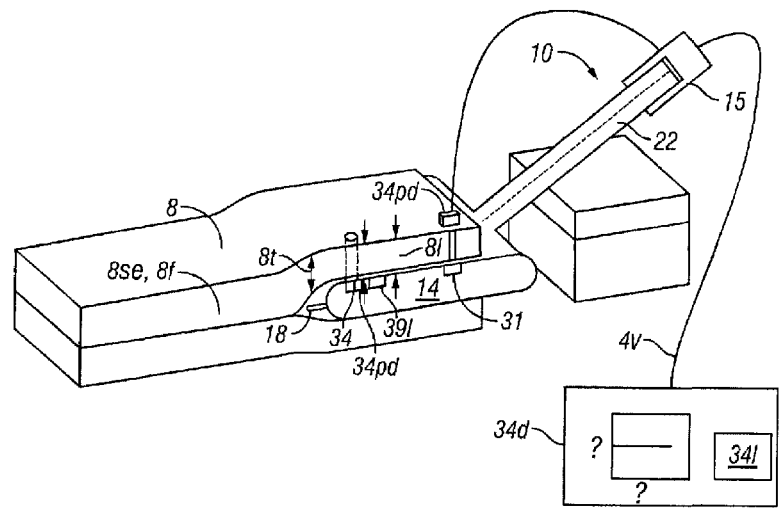
FIGS. 58 through 59 illustrate an apparatus of the present invention for dissecting or cutting tissue with a housing configured to be deployable in situ to allow subcutaneous insertion of all or portion of the housing 14 through a single incision.
Figure 59:
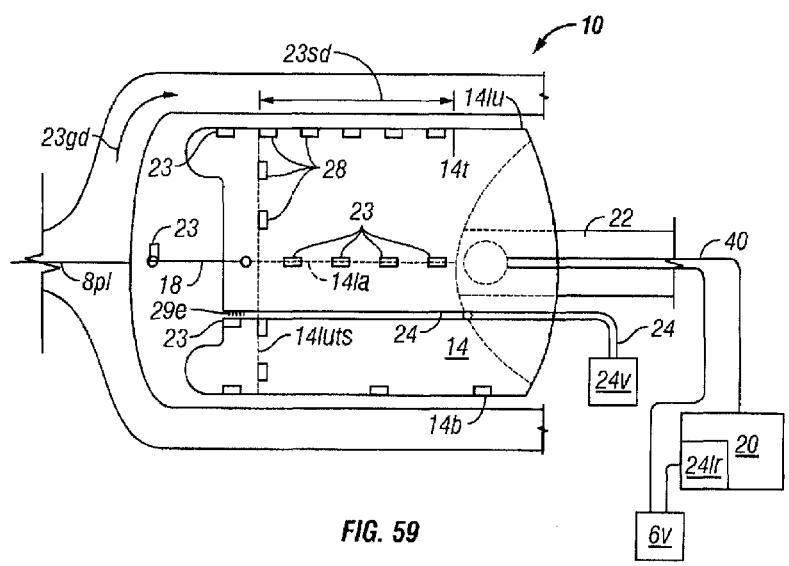

Referring now to FIGS. 58-59, in various embodiments, electrode-housing 14 can be configured as to be deployable in situ to allow subcutaneous insertion of all or portion of housing 14 or apparatus 10 through a single incision can be in the range of 0.25 to four inches in length. After insertion, deployment of housing 14 or portions thereof creates an initial dissection pocket 8dp for the deployed dissector. Thus, housing 14 can have a non-deployed state shown in FIG. 58 and a deployed state shown in FIG. 59. This can be accomplished having all or portions of housing 14 pivotally coupled to extender 22 using a pivot, hinge or cam mechanism known in the art. Also, all or a portion, of housing 14 can be articulated to be movable from a non-deployed state to a deployed state. This can be accomplished by means of pull wire/rod or pull mechanism known in the medical device/catheter art. It can also be accomplished pneumatically or hydraulically by configuring all or portions of housing 14 to be actuable by pneumatic or hydraulic means such as the use of a hydraulic or pneumatic device or force application device (e.g. a hydraulic press).

In an embodiment, this can this can be accomplished by use of using an inflatable member 14im known in the medical device arts (such as inflatable polyethylene or silastic or latex balloon) which is disposed or otherwise coupled to the interior of housing 14. In another means for deployment, housing 14 can include a deployment spring 14ds (either a coil or leaf spring) which can be actuable by an actuating member wire 39 coupled to hand piece 15.

Deployable embodiments of apparatus 10 can be configured to have a non-deployed profile or footprint to allow access through small incision sites directly or through surgical sheaths and introducing devices known in the art. Thus in use, deployable embodiments of apparatus 10 can also allow for reduction of the size of the incision site 8*is* to access the target tissue site 8 versus standard plastic surgery procedures such as face lift. This reduced incision size can also allow the incision site to less visible upon healing as well as placed in less visible locations such as the scalp Apparatus 10 can be used by the surgeon to dissect and separate selected tissue layers 8*l* in a selected plane of dissection 8*pd*. This can be done in one pass to dissect a skin envelope 8*se* or tissue flap 8*f* corresponding in width to the width of 18*w* of electrode 18 or can be done in multiple passes for larger tissue flaps.

The larger the advancement flap, the greater the number of passes that can be done. Although multiple passes may be needed, the overall thickness of the flap will be uniform. This allows the surgeon to preserve or substantially preserve the subdennal vascular plexus of the advancement flap and also avoid or substantially avoid damage to vital subjacent structures such as muscles, nerves and blood vessels.

After the surgeon has dissected a desired area of a selected tissue layer 8*l* such as the skin envelope 8*se*, the surgeon can then make further passes at substantially the same site to dissect subjacent or deeper tissue layers such as the adipose layers, breast tissue, or scar layers or transect the fibrous septae to correct cellulite or other selected such as a keloid scar, or cyst or lipoma. Also multiple passes can be done over the same area to sculpt or contour a selected layer, such as an adipose layer to produce a desired contour such as the contour in the buttocks or breast area. In use these and related embodiments can allow the surgeon to produce a desired skin contour by controlling one or more of (i) the depth of dissection and (ii) the number of layers dissected. Further such embodiments can also allow the surgeon to produce a varying contour such as that in the buttocks. area by varying the thickness of dissected adipose or tissue layers. This can be done by doing one pass in one location and/or multiple passes in another adjacent or other location.

Referring back to FIGS. 14-18, in various embodiments, apparatus 10 can be configured to allow a surgical dissection to be performed in a closed or 'blind' fashion without the surgeon needing to directly visualize the plane of dissection. Instead, the prominence of the superficial guide in situ can be visualized through the skin by the surgeon. As discussed herein this can be facilitated by configuring housing 14 to have a raised side contour 21*rsc* or ridges 21*r* which can function as transcutaneous markers 21 discussed. Raised side contour 21*rcs* or ridges 21*r* can be curved, u-shaped, triangular, square and combinations thereof.

Figure 60:
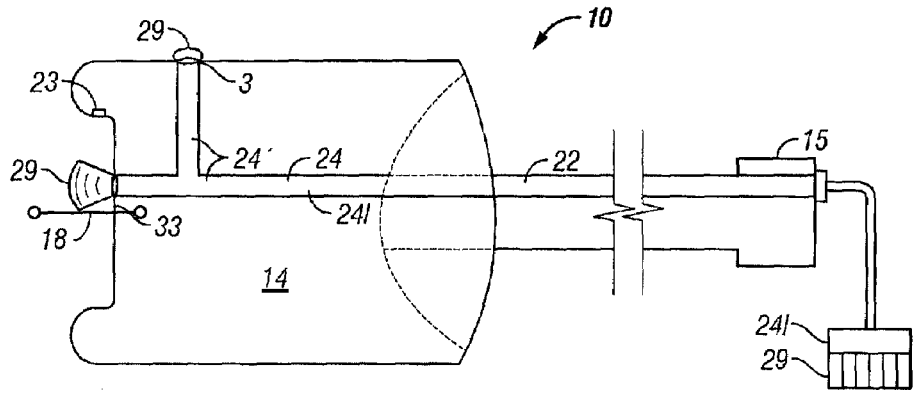
FIG. 60 illustrates an apparatus of the present invention for dissecting or cutting tissue that provides transcutaneous visualization.

Referring now to FIG. 60, in another embodiment, transcutaneous visualization can be accomplished by use of an LED or other light source 34 integral or attached to housing 14. Light source 34 can configured to have a wavelength and intensity sufficient to illuminate through the skin. Suitable lights sources 34 include LEDs used for pulse oximeters as known in the art. In a related embodiment, light source 34 can also be configured as a thickness measurement device 34*t* to provide a measurement of the thickness 8*t* of the skin envelope 8*se* or selected tissue flap. This can be accomplished using optical range/thickness finding technology known in the art. In an embodiment, this can be accomplished using a light source 34 such as a LED (which can be in the red or infrared range) and photo-detector 34*pd* to measure the amount of light absorbed by the skin.

A correlation can be established between the amount of light absorbance and skin thickness using one or more numerical or curve fitting methods known in the art such as cubic spline, least squares and polynomial curve fitting methods. In various embodiments, photo-detector 34*pd* can be configured to be placed on top of the skin or substantially adjacent light source 34 where it is configured to measures reflected/scattered light from skin envelope, where the amount of reflected light is proportional (inversely or otherwise) to skin envelope thickness.

Measurement device 34*t* can be configured to provide the physician with a real time indication of the skin envelope or tissue flap thickness 8*t* and thus the dissection depth 8*dd* as well. Measurement device 34*t* can be coupled to a display instrument which 34*d* can include associated logic resource 34*lr* and an optical power source. Optical measurement device 34*t* can be pre calibrated or can be configured to be calibrated using the patient's skin to account for variations in skin composition (e.g. pigmentation, vascularity, etc.).

By providing feedback of skin envelop thickness, measurement device 34*t* can be configured to allow the physician to one or more of the following: (i) have finer control over the dissection procedure including the skin envelope/flap thickness, (ii) make adjustment of apparatus 10 as needed to maintain the selected thickness (iii) obtain a more uniform or precise thickness of the skin envelope or tissue flap over a selected length of dissected tissue; (iv) controllably vary the envelope/flap thickness over a selected length of tissue.

In a related embodiment, light source 34 or measurement device 34*t* can be configured to detect for the preservation or damage of the dermal or sub-dermal vascular plexus. This can be accomplished by using LEDs or laser diode in the a red (660 nm) and/or an infrared (940 nm) range to detect the presence of blood in the plexus. Should the should the oxygenated signal drop or decrease in slope the surgeon is provided with an indication of thermal affects to the plexus before significant damage occurs and can thus stop the dissection procedure, decrease the power levels from the RF or other energy source, increase the level of cooling to tissue site, or a combination thereof.

In various embodiments, apparatus 10 can be configured to treat one or more of the following anatomical or dermatological deformities, including without limitation, Facial Cervical Rhytids, Breast Ptosis, Brachial Skin Redundancy, Post Partum Laxity of the Abdomen with Lipodystrophy, Lipodystrophy of the Hips and Thighs With Skin Laxity, Buttock Ptosis and Knee Ptosis with Lipodystrophy. Accordingly, in related method embodiments of the invention, apparatus 10 can used to perform one or more of the following surgical or medical procedures including, without limitation, Liposuction (Suction Assisted Lipectomy), Face lift (Rhytidectomy), Breast Reduction (Reduction Mammoplasty), Tummy Tuck (Abdominoplasty), Buttock Lift and combinations thereof. Liposuction (Suction Assisted Lipectomy), Face lift (Rhytidectomy), Mastectomy, Breast Reduction (Reduction Mammoplasty), Tummy Tuck (Abdominoplasty), Buttock Lift and combinations thereof.

Referring back to FIGS. 2-7, apparatus 10 can be configured to produce a substantially uniform depth of dissection for one or more of theses procedures. This can be achieved by selection of the size and shape of housing 14 (e.g. height), electrode 18 and extenders 22. For example, the height 14*h* of housing 14 can be adjusted (increased or decreased using embodiments described herein) to produce different depths of dissection for a breast reduction vs. a tummy tuck procedure. Also a smaller housing 14 can be used for procedures with smaller tissue flaps and/or dissection pockets and requiring more precise control of the area or plane of dissection such as face lift procedure. Further housing 14 can be narrow for target tissue areas having tight or narrow access.

In various method embodiments, apparatus 10 can be used to perform one or more surgical techniques that can be useful for producing a desired aesthetic tissue affect. For example, in an embodiment, apparatus 10 can be used to correct buttock ptosis with reduced or minimal scarring as well as produce diminishment of cellulite in the plane of dissection. This can be accomplished by using apparatus 10 to transect eliminating or reducing dimpling of the skin in the dissected area.

In another embodiment, apparatus 10 can be used as an adjunct to aesthetic procedures such as liposuction where contour reduction from liposuction can be accompanied with smoothing and tightening of the overlying skin envelope. In these and related procedures apparatus 10 can be configured to be used to produce tightening of the undermined skin envelope. This can be accomplished from one or more effects of closed electro-surgical dissection including but not limited to: (i) closed advancement and (ii) thermal tightening of the tissue flap. Thermal conductive tightening of the skin envelope occurs from primary collagen contraction of the released fibrous septae of the subcutaneous tissue and from primary collagen contraction of the dermis due to heating of the these tissues at or above the temperature of collagen contraction.

Energy can also be delivered to produce a delayed wound healing tightening of the skin envelope that will occur during subsequent months. Also the combined procedure can function as a portal for closed application contouring of the subcutaneous tissue with endoscopic staples. In these and related embodiments, apparatus 10 can be configured for the use of an endoscope as well as introduction of endoscopic staples. This can be accomplished by configuring one or more lumens 24' to have sufficient diameter to allow the passage of an endoscope. In such embodiments lumens can be 5-20 french in diameter.

In an embodiment, the RF energy delivered to the tissue site to dissect the tissue plane can also be configured to heat the developing tissue flap immediately overlying the electrodes. This in turn, heats the skin envelope directly or indirectly through conduction, convection or both. This heating in turn will result in contraction, causing tightening of the skin envelope because of tightening of the dermis and fibrous septa. Subjacent tissue can be electro-surgically dissected and contoured and during this process the overlying skin envelope/tissue flap can be tightened by thermal conduction to selected portions of the skin envelope.

The delivery of energy can be titrated to on the one hand, raise collagen components of the flap to a temperature sufficient to cause shrinkage collegenous matrix of the overlying dermis with a subsequent wound healing response, but on the other stay below a temperature and/or total heat delivery that would cause damage or necrosis of the subdermal plexus.

In various embodiments, configuration of RF energy for skin tightening can be accomplished by manipulation of the RF energy waveform (e.g. frequency, amplitude, duty cycle etc). In an embodiment, the RF generator can be configured to have two modes of power delivery, one configured for cutting and the second configured for heating of the skin envelope to collagen contraction for skin tightening. The heating waveform can have lower power levels and lower frequencies than the cut waveform. In various embodiments, the power level and frequency of the heating waveform can be in the range of about 5 to about 30 watts and about 250 to about 750 kHz respectively.

Power source 20 or a coupled control system 60 (described herein) can be configured to alternate between two wave forms in selected duty cycle or alternatively the physician can manually toggle back and forth between the two via means of a foot switch or other manual control means. Further description of methods and techniques of tissue tightening and remodeling the skin through heating of collagen containing tissue (e.g. the skin) by RF energy and other means is found in U.S. Pat. Nos. 5,919,219, 6,241,753, 6,311,090 and 6,350,276, which are all fully incorporated by reference herein.

Referring back to FIGS. 23-25, reduction or prevention of thermal injury or necrosis of the subdermal plexus and/or dermal layers can be further facilitated by use of cooling fluid 29 that can be delivered to tissue layers and structures above and below the plane of dissection such as sub-dermal plexus or even to the skin surface to prevent excessive thermal injury (e.g. erythemia, blistering, burns etc.) to the dermal layer or skin surface. In various embodiments, cooling fluid 29 can be delivered through lumens 24' or via one or more fluid distributions ports or apertures 33 position on housing 14. Further description of methods and techniques of tissue tightening and remodeling through heating of collagen containing tissue (e.g. the skin) by RF energy and other sources and mechanisms is found in U.S. Pat. Nos. 5,919,219, 6,241,753, 6,311,090 and 6,350,276, which are all fully incorporated by reference herein.

Figure 61:
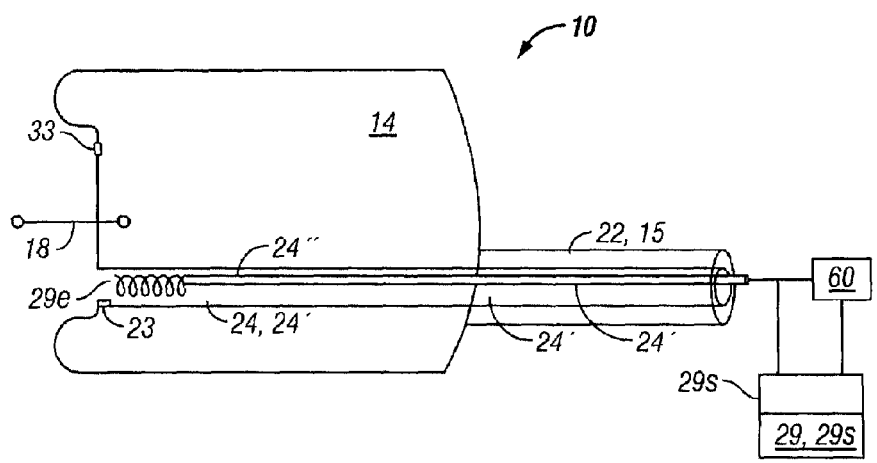
FIG. 61 illustrates an apparatus of the present invention for dissecting or cutting tissue that is configured to be monitor by temperature of tissue adjacent or near the housing.
Figure 62A:
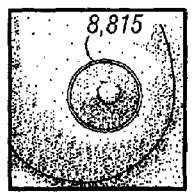
FIG. 62 illustrates an apparatus of the present invention for dissecting or cutting tissue with cooling that can be achieved by irrigation of the tissue surface or selected portions of the tissue site with a cooled fluid.
Figure 62B:
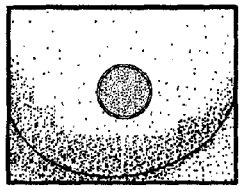
Figure 62C:
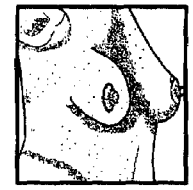
Figure 62D:
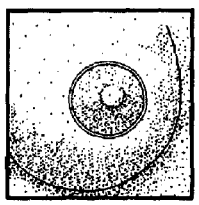
Figure 62E:
Figure 62F:

Referring now to FIG. 61, in various embodiments, apparatus 10 can be configured to monitor the temperature of tissue adjacent or near housing 14. This can be accomplished by the use of one or more temperature sensors 23 coupled, integral or disposed on within housing 14. Temperature sensors 23 can the be coupled to a feedback control system described herein or logic resources 20*lr* coupled to the power source 20 to regulated the delivery of energy to electrode 18 and tissue site 8.

In use, temperature monitoring can be configured to titrate or otherwise control the delivery of energy to the target tissue site 8.

Further, in various method embodiments temperature monitoring can be used to control energy delivery to the tissue site to perform or facilitate of one or more of the following: (i) tightening of the skin envelope via collagen contraction, (ii) tightening of the skin envelop via a wound healing response, (iii) produce a substantially uniform plane of tissue dissection using electro-cautery or other EM cutting energy; and (iv) prevent or minimize thermal injury or necrosis to selected tissue layers such as the subdermal plexus, musculocutaneous and perforator arteries.

In a particular embodiment, temperature monitoring can be used to titrate the delivery of energy to tighten the skin from thermal collagen contraction and wound healing while minimizing or preventing thermal injury to the dermal-subdermal plexuses.

Suitable temperatures sensors 23 that can be employed include thermisters, thermocouples and other solid state or optical temperature sensors known in the art. In various embodiments, sensors 23 can be positioned on the top 14*t*, bottom 14*b* or sides 14*s* of housing 14 as well as on or near suction device 24.

In a particular embodiment sensors 23 can be positioned on both the top and bottom of housing 14 so as to provide simultaneous temperature monitoring capability of both superior tissue layers (e.g., the skin envelope) and subjacent or inferior tissue layers. These and related configuration can be used to control delivery of energy to the tissue site to dissect out a selected tissue plane using electrode 18 and deliver energy to the skin envelope to tighten the envelope (via thermal contraction of collagen) while minimizing injury to the subdermal plexus and/or other subjacent tissue structures.

In related embodiments, sensors 23 can be distributed along a longitudinal axis 14*la* and/or lateral axis 14*lata* of housing 14 with the distribution configured to generate a lateral or a longitudinal temperature profile 23*p* of superior or subjacent contacting tissue layers. The temperature profile can used to monitor, control or perform one or more of the following functions: (i) delivery of energy to the tissue site, (ii) delivery of cooling to the tissue site, (iii) rate of advancement of housing 14 by the physician, (iv) direction of advancement of housing 14 (iv) positioning of housing 14 by the physician.

In other embodiments sensors 23 can be positioned to measure one or more temperature gradients 23g such as temperature gradient between tissue in contact with the electrode and tissue in the nascent skin envelope or tissue flap. Accordingly in such embodiments sensors 23 can be positioned on or near electrode 18 and also on the top portions 14t of housing 14 or the roller. Such temperature gradients can be utilized by the physician and/or a control system to monitor the delivery of energy for one or more of the following: (i) assure sufficient temperature at or near the electrode for electro-surgical cutting, (ii) assure proper temperature for collagen contraction of selected portions of the skin envelope/tissue flap or (iii) assure temperatures stay below a threshold that would cause thermal damage or severe thermal damage to flap layers containing the sub-dermal plexus or other tissue structures.

In related method embodiment, the delivered RF power levels can be controlled (by a control system, by the physician, or combination of both) to maintain a selected temperature gradient, such as the gradient between the tissue proximate the electrode and superior tissue in the developing skin envelope. This type of control and associated control systems and algorithms can be employed independently or in conjunction with control systems and/or algorithm that utilize absolute temperature as an input. In another method embodiment, temperature a gradient across the horizontal surface of the electrode can be monitored to assure a substantially uniform (or other selected temperature profile) cutting temperature across the electrode. If a portion of the electrode becomes too hot or too cool, the control system can figured to dynamically respond by changing one or more of the following (i) the delivered RF power level, (ii) the RF wave form or shape, (iii) the power duty cycle, (iv) the shape of the electrode (via strut member 19 or other mechanical means) to alter the current density at that portion of the electrode; or (v) the rate of cooling fluid delivered to selected portions of the electrode (e.g. the hot portions) via cooling apertures or other directed cooling or cooling means.

In other embodiments, sensors 23 can also be positioned adjacent or near electrode 18 such as on or in the suction device 24 to monitor the temperature of the vapor being generated at the tissue site. This temperature can be utilized to control a vapor cooling element 29e and/or the delivery of cooling fluid 29 to portions of apparatus 10 and the tissue site.

Tissues temperatures that can be monitored include without limitation that of superior layers such as the skin envelope including dermal-sub-dermal plexus and subjacent layers such as subcutaneous layer, fascial and muscular layers. Suitable temperature sensors can include thermisters, thermocouples, fiber optic, solid state or other temperature sensors known in the art.

In various embodiments, adjacent tissue and superjacent skin can be cooled by one or more methods to prevent or minimize thermal injury, damage or tissue necrosis to selected tissue layers in the tissue flap and/or subjacent layers. Cooling can be accomplished by the use of a cooling media 29 to cool non-target tissue by convection, conduction or a combination of both. The cooling media 29 can be a fluid 29 which can be a liquid or a gas, or a combination of both. Examples of suitable cooling fluids include, water, saline solution and ethanol and combinations thereof. Other embodiments can utilize a cooling fluid or gas which serves to cool adjacent tissue by ebullient cooling or Joule Thomson Effect cooling as well as the mechanisms described above. Embodiments utilizing Joule-Thomson Effect cooling can have a nozzle-shaped aperture 33n to provide for expansion of a cooling fluid 29. Examples of cooling fluid 29 include, but are not limited to, Freon, $CO_2$, and liquid nitrogen. The amount of cooling can be controlled by control of one or more of the following parameters (i) temperature of the cooling solution (ii) flow rates of the cooling solution (iii) heat capacity (e.g. specific heat) of the cooling solution.

Referring now to FIG. 62, in another embodiment, cooling can be achieved by irrigation of the tissue surface or selected portions of the tissue site with a cooled fluid 29 as is used during lavage and related surgical procedures known in the art. Accordingly in these and related embodiments, apparatus 10 can include be configured to be used in conjunction with an irrigation device 24i, or suction device 24 can also be configured as an irrigation or lavage device 24i. In an embodiment, the lavage device can be a pulsatile lavage irrigator known in the art. Examples of suitable pulsed lavage irrigators include, but are not limited to, the Davol® Simpulse® Solo (Manufactured by the Davol Corporation), the Stryker Surgilav® Plus® (Manufactured by the Stryker Corporation) and the Zimmer Pulsavac® III (Manufactured by the Zimmer Corporation).

Figure 63:
FIG. 63 illustrate an apparatus of the present invention for dissecting or cutting tissue that provides cooling of the skin and adjacent tissue by suctioning off, capturing or cooling a vapor produced from vaporization of tissue during energy delivery.
Figure 64:
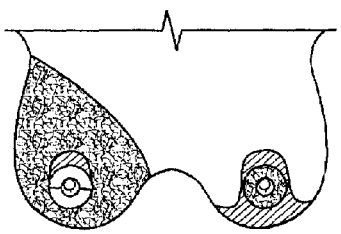
FIGS. 64(a) through 64(f) illustrate use of an apparatus of the present invention in the performance of a skin preservation mastectomy in which no breast skin is resected.

Referring now to FIG. 63, in an embodiment, cooling of the skin and adjacent tissue can be achieved by suctioning off, capturing or cooling the vapor (steam etc) produced from vaporization of tissue during energy delivery (e.g. via electro-cautery) to the tissue site from electrode 18 or other energy delivery device described herein. Suctioning of steam can be accomplished using suction device 24 or a separate suction or device coupled to a vacuum source. In an embodiment, suction can be performed by the same aspiration device used to perform liposuction. Alternatively, a cooling element 29e can utilized to condense or otherwise cool vapor produced during energy delivery from energy delivery device 18 to the tissue site such as during cutting or coagulation from electro-cautery procedures. Cooling element 29e can be coupled to or positioned sufficiently proximate to energy delivery device 18 to condense and cool the generated vapor. In an embodiment, cooling element 29e can itself be cooled by a cooling fluid source 29s, such as a cryogenic gas 29g, coupled to element 29e. Cooling element 29e can have a variety of shapes including a coiled shape, spiraled helical shape, or a fin-shape, one or more configured to maximize surface area for conductive and/or convective heat transfer.

Apparatus 10 can also be configured to provide cooling of electrodes 18 via lumens 24' to prevent tissue from the development of excessive impedance at electrode 18 from the deposition of charred tissue on the surface of electrode 18. Further description of tissue and skin cooling methods are found in U.S. Pat. Nos. 6,350,276 and 6,377,854 which are fully incorporated by reference herein.

As discussed herein, in various method embodiments, apparatus 10 can be used to perform one or more surgical techniques that can be useful for producing a desired aesthetic tissue affect. Further, by maintaining a substantially uniform skin envelope thickness during dissection, apparatus 10 facilitates the removal or reduction of contour irregularities for example, the dimpled skin appearance resulting from cellulite. This can be accomplished by configuring apparatus 10 to produce a uniform skin envelope, transect the fibrous septae that are attached to the skin and muscle fascia and deliver thermal energy from the electrode to substantially uniformly tighten the released skin envelope by thermal collagen contraction and a subsequent wound healing response discussed herein. By applying RF energy to a skin envelope having a substantially uniform thickness, as opposed to a non-uniform thickness, the resulting tightening of the skin by RF energy application is itself made more uniform. More simply put, starting with a more uniform tissue layer to be tightened results in a more uniformly tightened layer. Apparatus 10 can be configured to facilitate this process by providing the physician qualitative and/or a quantitative assessment of the uniformity of skin envelope thickness pre and/or post tightening through either the use of trans-cutaneous visualization of the developing skin envelope and/or use of skin thickness measurement methods both described herein.

Skin deformities can be further improved by using apparatus 10 to uniformly transect the fibrous septae at the tissue site with each pass of apparatus 10 through the selected plane of dissection. Accordingly, apparatus 10 can be specifically configured to transect the fibrous septae by configuration of one or more of the electrode dimensions (e.g. diameter), shape, stiffness, edge and electro-cautery properties. For example, the electrode stiffness can be increased and/or the electrode can have a sharpened edge. By providing a means for uniformly transecting the fibrous septae, apparatus 10 facilitates more uniform tightening because the skin is no longer being pulled down or constrained at intermittent locations to the underlying facia.

In an embodiment of a method for using apparatus 10 to correct a skin deformity, the surgeon makes an incision at or adjacent the tissue site. The surgeon then selects the desired tissue plane to dissect for example, the skin envelope from the underlying subcutaneous layers such as facia. The surgeon can visually acquire the desired dissection plane through direct visualization of the tissue within the incision site or through use of endoscopic visualization. If needed the surgeon can pre-adjust apparatus 10 to produce the desire depth of dissection by manipulation of one or more of the electrode, housing 14 or the roller.

If desired, the surgeon can manually start the plane of dissection and isolate or separate the respective tissue layers using his/her hands or via means of a surgical instrument such as scalpel, scissors or bovie and the like. The surgeon then inserts apparatus 10 through the incision and into the tissue pocket. For deployable embodiments, the surgeon inserts apparatus 10 in a non-deployed state and then deploys apparatus 10 within tissue pocket. The surgeon can adjust apparatus 10 in situ to produce the desired depth of dissection by manipulation of one or more of the electrode, housing 14 or the roller. Alternatively, the surgeon can remove apparatus 10 to make such adjustments. After connection to an RF power source (via the hand piece), the surgeon then energizes the electrode (using a footswitch or other activating means) to deliver RF energy and advances apparatus 10 through the selected dissection plane to dissect and separate the skin envelope (or other tissue layer) and transect the fiber septae. Advancement can be done by gripping the hand piece or the extender.

As discussed above, the surgeon can pre-isolate and start the plane of dissection manually or he/she can do so using apparatus 10. As the skin envelope is dissected by the RF electrode, delivery of thermal energy from the electrode cause thermal contraction of collagen within the skin envelope causing immediate tightening of the skin and subsequent tightening from a wound healing response. As the skin envelope is dissected and separated by the electrode it is guided (by the shape of housing 14 or roller) to slide over housing 14 or roller and is shielded from further heating; thus, protecting the dermal and subdermal plexes from thermal injury and necrosis.

This shielding can be further facilitated by the use of a cooling fluid delivered to the skin envelope from an irrigation means (e.g. apertures 33, nozzles 33n, lumens 24', etc.) coupled to housing 14 (e.g. via irrigation ports on the surface of housing 14) or an external irrigation means. The surgeon can continuously ascertain one or more of the path and depth of the developing dissection plane as well as the amount of skin tightening by transcutaneous visualization of marker ridges or bumps on housing 14 or roller or by using tissue thickness monitor.

This information is used by the surgeon can make adjustments as need to either the path of dissection or the depth of dissection by manipulation of one or more of the hand piece, extender or RF energy level. There is no need stop advancement or otherwise remove a hand from the hand piece to palpitate the skin to determine the path or depth of dissection (although the surgeon can do this if he/she desires. This results in one or more of (i) a more uniform dissection and uniform tissue flap/skin envelope, (ii) a better aesthetic outcome with smaller incisions and (iii) well as faster procedure times then procedures where it is necessary to stop advancement to palpitate the skin or otherwise remove one or both hands from a dissection instrument to do so.

The surgeon can advance apparatus 10 to stop at a selected end point within the tissue site. Then using the hand piece, the surgeon can withdraw housing 14 back to the incision site or some selected point in between. The surgeon can then observe the dissection plane either transcutaneously or through endoscopic visualization. Observation can be facilitated by using apparatus 10 or adjunct device(s) to irrigate and/or aspirate the newly dissected tissue plane as well insufflate the dissected area of tissue. If desired, the surgeon can then make multiple passes over the same area of the dissection plane to do one or more of the following: (i) smooth out the plane of dissection, (ii) widen the width of dissected skin envelope or other tissue flap; (iii) go back over the dissection plane to coagulate any bleeding tissue or vessels, (iv) deliver additional amounts of heat to the skin envelope or selected tissue flap to titrate the amount of collagen contraction and resultant skin tightening, or (v) dissect out a deeper tissue plane. For the last step, the surgeon can, if desired, readjust apparatus 10 to change the depth of dissection.

After completion of dissection within a given tissue area or path, the surgeon can then reposition housing 14 either at the existing incision to start a new path or swath of dissection or make a new incision and reposition housing 14 within the new incisions and then repeat one or more of the preceding steps to dissect a new area of tissue to create a continuous skin envelope (either in width lengths or both) or separate skin envelopes. One or more dissected skin envelopes or flaps can be advanced and surgically reattached (e.g. by suturing, stapling etc.) to a different tissue site, or alternatively separate envelopes can themselves by surgically reattached. Prior to attachment a selected area (e.g. length) of the skin envelope can be removed in order to create a selected contour or tightening affect at the target tissue site.

Accordingly, in various embodiments, housing 14 or roller can be configured to facilitate the attachment by serving as an underlying support for suturing, stapling or otherwise attaching the skin envelope or tissue flap to the edge of another incision or another tissue flap. In an embodiment, that incision can be in a concealed site such as the temporal scalp above the ear or occipital scalp behind the ear. Housing 14 or roller can also be configured to actually cut or transect sections of the skin envelope 8se either using electrode 18 or again serving as a support or guide for another surgical instrument such as a scalpel or surgical scissors.

Once the surgeon has completed the desired procedure, he/she can remove apparatus 10 through the original incision site or through another incision. In the latter case the surgeon advances housing 14 or roller to the second incision and then pulls it out directly or using forceps or other surgical tool. In these embodiments the hand piece or extender can be configured to be sufficiently flexible and atraumatic to be advanced under the skin through the dissection plane and then pulled out the second incision site. This can be accomplished by (i) fabricating the hand piece from flexible polymers and/or metals described herein otherwise known in the art such as superelastic metals (e.g. nitinol) and/or (ii) configuring the diameter of the hand piece or extender to fit through a small incision site (e.g. less 1, 0.5 or 0.25 inches). Once the surgeon has removed housing 14 and apparatus 10 he or she can then suture the incision site(s). The order of the above steps is exemplary and other order are equally applicable.

The following examples illustrate embodiments of methods of use of the invention using one more embodiments of apparatus 10.

EXAMPLE 1

Referring now to FIGS. 64a-64f, an application of an embodiment of apparatus 10 can be the performance of a skin preservation mastectomy in which no breast skin is resected . . . only the nipple areolar complex is resected with the subjacent breast tissue. With a uniform flap dissecting embodiment of apparatus 10, a subcutaneous flap of the preserved breast skin is 'closed dissected' without direct visualization of the plane of dissection. Due to the superficial guide component of the electrode housing, a uniform flap thickness if created with the dissection of the breast skin envelope. The predetermined flap thickness will preserve the subdermal vascular plexus and thereby limit breast skin envelope necrosis. The correct flap thickness will also enhance the oncological effectiveness of the procedure by not leaving breast tissue on the breast skin flap. In other words, an uneven dissection with the side effects of a too thin or a too thick plane of dissection will be avoided. Lastly, scarring is reduced; the entire procedure is performed through a small periareolar incision instead of a larger standard mastectomy incision that extends across the chest.

EXAMPLE 2

Figure 65:
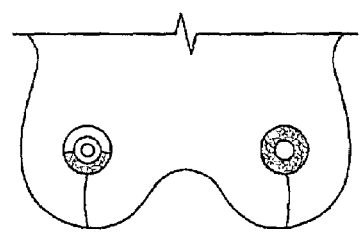
FIG. 65 illustrate use of an apparatus of the present invention for a facelift patient with redundant skin the cheeks, jowls and neck.

Referring now to FIG. 65, for a facelift patient with redundant skin the cheeks, jowls and neck, a large continuous incision is made that starts in the temporal scalp, extends around the ear and ends in the occipital scalp. With a uniform flap dissecting embodiment of apparatus 10, only 3 small (2 cm) incisions are made as insertion portals for the device. A continuous uniform flap of the scalp, face and neck is developed. With a process termed 'closed advancement', the uniform subcutaneous flap is then advanced upwards (superiorly) on the face and temporal scalp and the flap is advanced backwards (posteriorly) on the neck and occipital scalp.

Without resection of skin, the flap is secured in an advanced position with subdermal sutures at the incision portals. With this technique, a more youthful appearance of the face and neck can be achieved without the unsightly scars of the atypical facelift incision. Because the advancement is maintained with a series of subdermal fixation sutures in the temporal and scalp, any skin redundancy will be hidden in those areas. To provide additional postoperative support and compression, an elastic garment can be worn by the patient until the flap has adhered in an elevated position. As a surgical adjunct, the procedure can use liposuction to jowls and neck through the same incisions.

EXAMPLE 3

Figure 66:
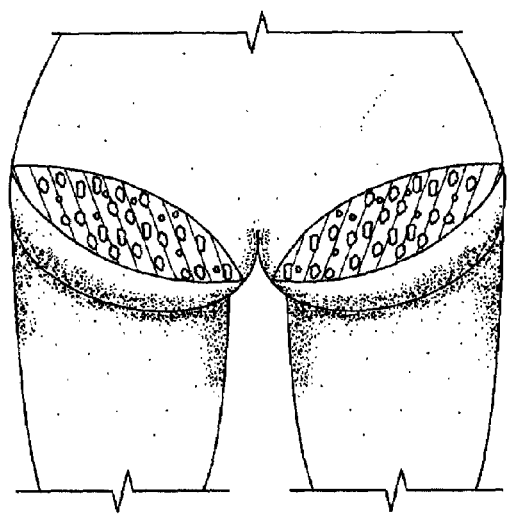
FIGS. 66 and 67 illustrate the use of an apparatus of the present invention for a patient with breast ptosis.
Figure 67:
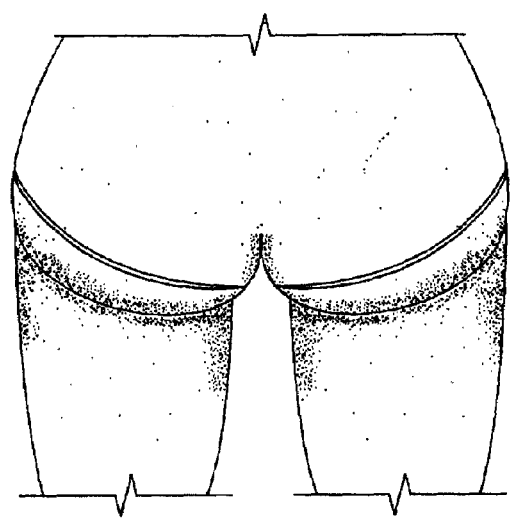
Figure 68:
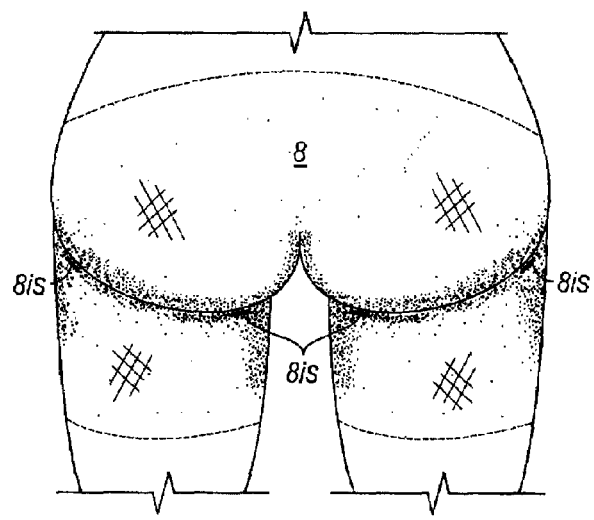
FIGS. 68 through 71 illustrate the use of an apparatus of the present invention for the aesthetic surgical discipline of 'closed advancement' using a closed flap dissection with a uniform flap.
Figure 69:
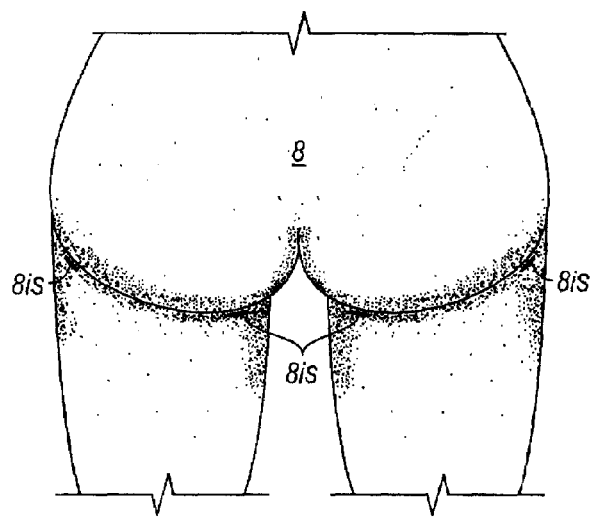
Figure 70:
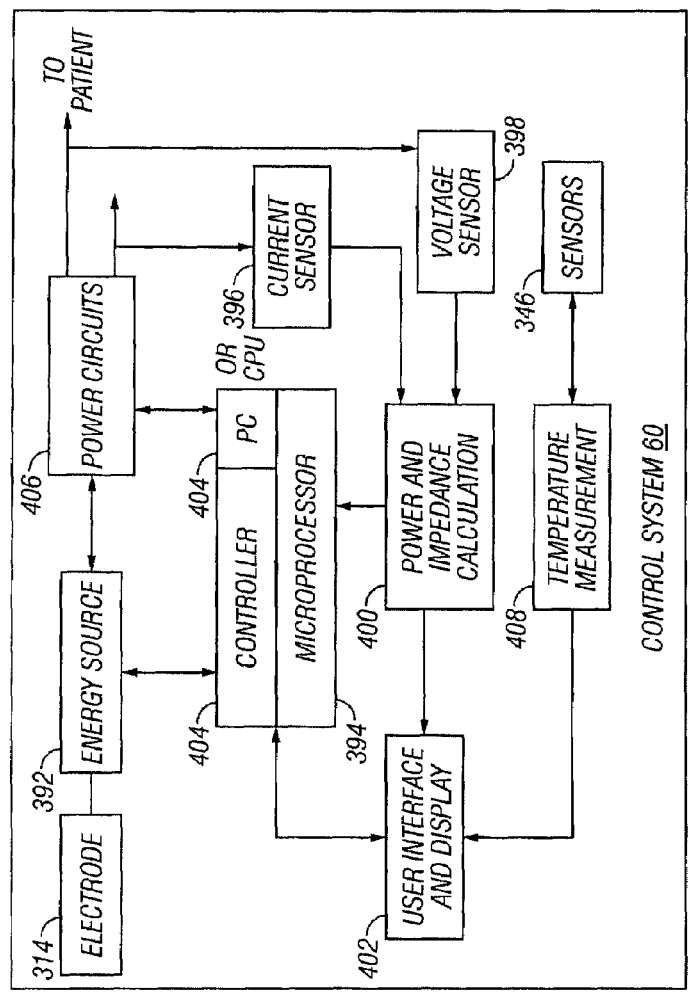
Figure 71:
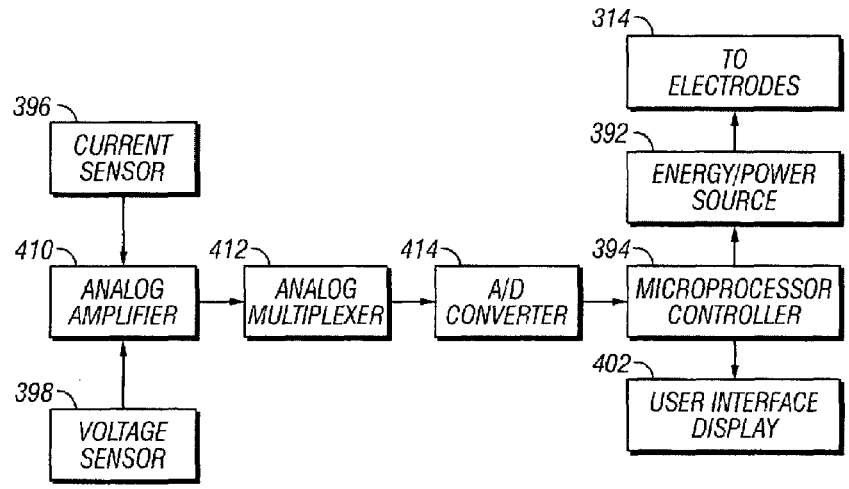

Referring now to FIGS. 66 and 67, for a patient with breast ptosis, large mastopexy (breast uplift incisions that are anchor shaped) incisions can be avoided with closed dissection of the breast skin envelope. Leaving the nipple-areolar complex attached to the underlying breast tissue, the entire breast skin envelope is closed dissected with a uniform flap dissecting embodiment of apparatus 10. For more severe cases of breast ptosis, the entire breast skin envelope including the nipple areolar complex is dissected as a uniform breast skin flap. The uniform breast skin envelope is then advanced superiorly to provide an uplifted contour of the breast. A specifically designed supportive bra can be worn by the patient for 24 hours a day for 3 weeks until adherence of the breast skin flap occurs.

EXAMPLE 4

Referring now to FIGS. 68-71, the aesthetic surgical discipline of 'closed advancement' using a closed flap dissection with a uniform flap dissecting embodiment of apparatus 10 can create new aesthetic procedures in areas that are currently off limits to standard skin resection procedures because the trade off between an unsightly scar is poor in comparison to the Aesthetic benefit. For a patient with buttock ptosis, a uniform subcutaneous flap is raised with closed dissection over the buttocks and the superior aspect of the posterior lateral thigh. The flap is then advanced superiorly, securing the flap in an elevated position with subdermal mooring sutures in the infragluteal fold. Additional support is provided with a specifically designed girdle that is worn by the patient 24 hours a day for 3 weeks.

EXAMPLES 5

In this example the patient is an elderly woman who required a mastectomy for extensive in situ ductal carcinoma of the right breast. During the reconstruction of the right breast, the patient also requires a mastopexy/repositioning of the left breast to achieve symmetry with the reconstructed right breast. A closed electro-surgical dissection with upward advancement and thermal conductive tightening of the dissected breast envelope could provide necessary repositioning of the left breast for symmetry with the reconstructed right breast. The typical inverted 'T" shaped scar was avoided on the repositioned breast.

EXAMPLES 6

In this example the patient is a middle-aged man with transaction of the left facial nerve from a motor vehicular accident. Surgical repair of the nerve was performed initially but the patient was left with a residual paresis that produced a severe facial deformity with ptosis of the left face and hyperactivity of the non-injured right face. To correct the post traumatic deformity, a facial reconstruction could be performed on the left face that involved a closed electro-surgical dissection with upward advancement and thermal conductive tightening of the dissected skin envelope of the left. Visible preauricular incisions were avoided and the post surgical scars were hidden in the temporal and occipital scalp.

EXAMPLES 7

In this example the patient is a young woman who sustained a severe contusion to the left lateral thigh from a bicycle accident. As result, a contusion lipolysis occurred that resulted in a traumatic contour depression of the left lateral thigh. To correct the contour depression, a thigh reconstruction could be performed that involved liposuction of the adjacent subcutaneous tissue surrounding the contour depression with closed electrosurgical dissection with redistribution and thermal conductive tightening of the dissected skin envelope of the thigh. The reconstruction could be performed through small incisions that are typically used for liposuction.

(1) OTHER EXAMPLES

Various embodiments of apparatus 10 can be configured to assist the surgeon in generating a variety of types of tissue flaps and flap patterns known in the surgical arts depending upon the tissue site and/or tissue condition. Apparatus 10 can be configured to facilitate dissection without limitation of a myocutaneous flap, a random patter skin flap, an omental flap, an axial flap and the like all known in the surgical arts. Also apparatus 10 can be configured to allow the surgeon to substantially preserve all portions or the vasculature in the flap such as a musculocutaneous artery, a perforator artery, a segmental artery, or a subdermal plexus. This can be accomplished by embodiments of apparatus 10 having endoscopic viewing capability (described herein) as the use of sensors (such as thermal, ultrasound or optical sensor) coupled to the front or other portion of housing 14 to detect the presence of an artery. In a specific embodiment an ultrasound sensor can be coupled to housing 14 and configured to detect the presence of the flowing blood in artery by virtue of a Doppler ultrasound signal using gated ultrasound technology known in the art. In another embodiment an infrared sensor 23 can be used to detect the higher concentrations of oxygenated blood within the artery (versus other tissue) using pulse oximetry technology known in the art.

Figure 72:
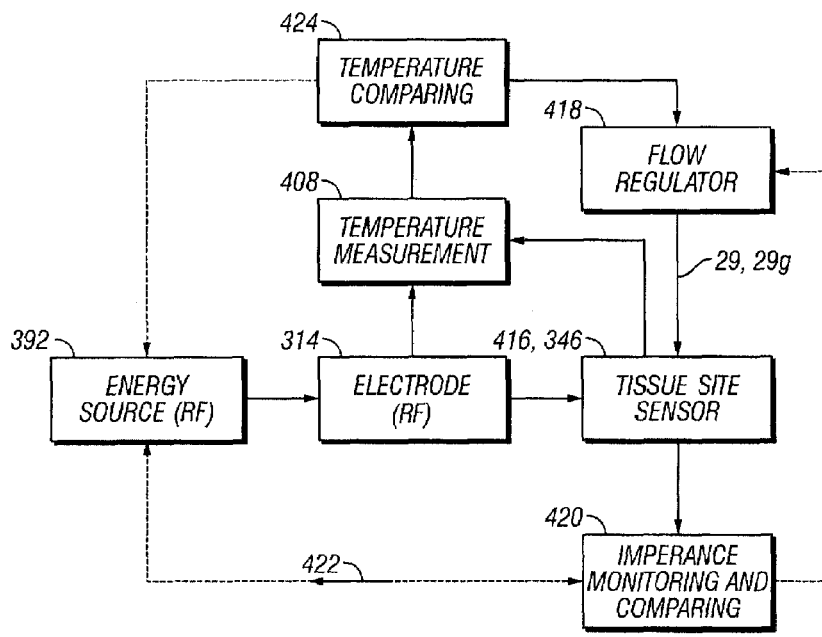
FIG. 72 illustrates the use of an apparatus of the present invention with an open or closed loop feedback system/resources.

Referring now to FIG. 72, in an embodiment, apparatus 10 can be coupled to an open or closed loop feedback system/resources 60. As shown in FIG. 72, feedback system 60 couples sensor 346 to power source 392. For purposes of illustration, energy delivery device 314 is one or more RF electrodes 314 and power source 392 is an RF generator, however all other energy delivery devices and power sources discussed herein are equally applicable.

The temperature of the tissue, or of RF electrode 314 is monitored, and the output power of energy source 392 adjusted accordingly. The physician can, if desired, override the closed or open loop system. A controller 394 or microprocessor 394 can be included and incorporated in the closed or open loop system 60 to switch power on and off, as well as modulate the power between one or more modes or waveforms (e.g. monopolar, bipolar; cut and coagulate etc). The closed loop system utilizes microprocessor 394 to serve as a controller to monitor the temperature, adjust the RF power, analyze the result, refeed the result, and then modulate the power. More specifically, controller 394 governs the power levels, cycles, and duration that the radio frequency energy is distributed to the individual electrodes 314 to achieve and maintain power levels appropriate to achieve the desired treatment objectives and clinical endpoints such as tissue dissection and conductive heating skin tightening. Controller 394 can also in tandem, govern the delivery of cooling fluid. Controller 394 can be integral to or otherwise coupled to power source 392 and can also be coupled to a fluid delivery apparatus. In one embodiment controller 394 is an Intel® Pentium® microprocessor, however it will be appreciated that any suitable microprocessor or general purpose digital or analog computer can be used to perform one or more of the functions of controller 394 stated herein.

With the use of sensor 346 and feedback control system 60 tissues layers (adipose tissue, fascia etc.) adjacent to RF electrode 314 can be maintained at a desired temperature for a selected period of time without causing a shut down of the power circuit to electrode 314 due to the development of excessive electrical impedance at electrode 314 or adjacent tissue. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output in an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of energy when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output in an appropriate amount in order to maintain the desired temperature delivered at the sensor 346. A multiplexer can be included to measure current, voltage and temperature at sensor 346. Energy can be delivered to RF electrode 314 in monopolar or bipolar fashion.

Controller 404 can be an analog or digital controller, or a computer with driven by control software. When controller 404 is a computer it can include a CPU coupled through a system bus. On the system can be a keyboard, disk drive, or other non-volatile memory systems, a display, and other peripherals,
as are well known in the art. Also coupled to the bus are a program memory and a data memory. Also, controller 404 can be coupled to imaging systems including, but not limited to, ultrasound, thermal and impedance monitors.

The output of current sensor 396 and voltage sensor 398 are used by controller 404 to maintain a selected power level at RF electrode 314. The amount of RF energy delivered controls the amount of power. A profile of the power delivered to electrode 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 73:
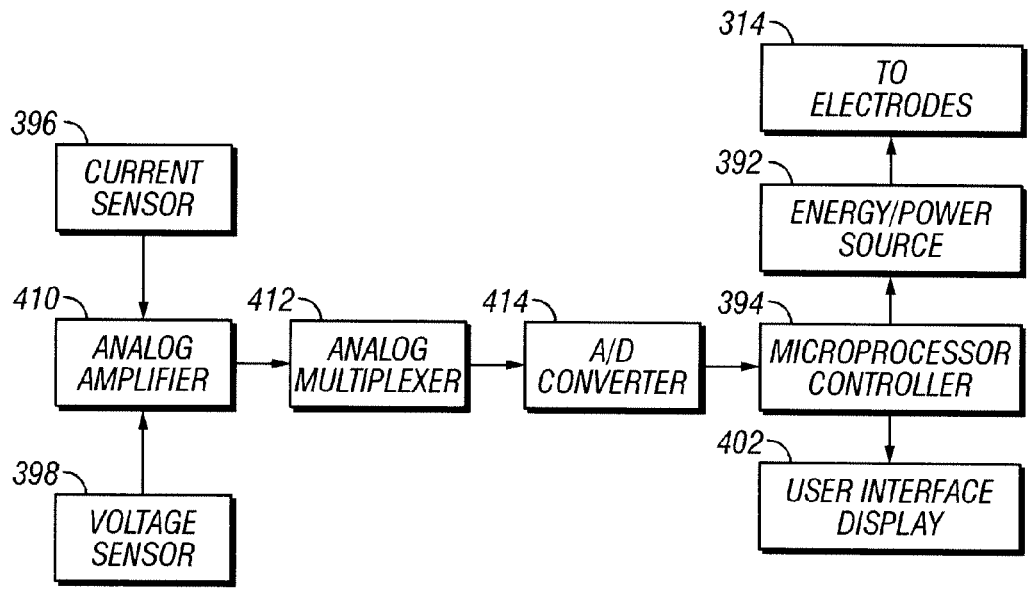
FIG. 73 illustrates the use of an apparatus of the present invention with a current sensor and voltage sensor.

Referring now to FIG. 73, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394.

Microprocessor 394 sequentially receives and stores digital representations of impedance and temperature. Each digital value received by microprocessor 394 corresponds to different temperatures and impedances. Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 74:
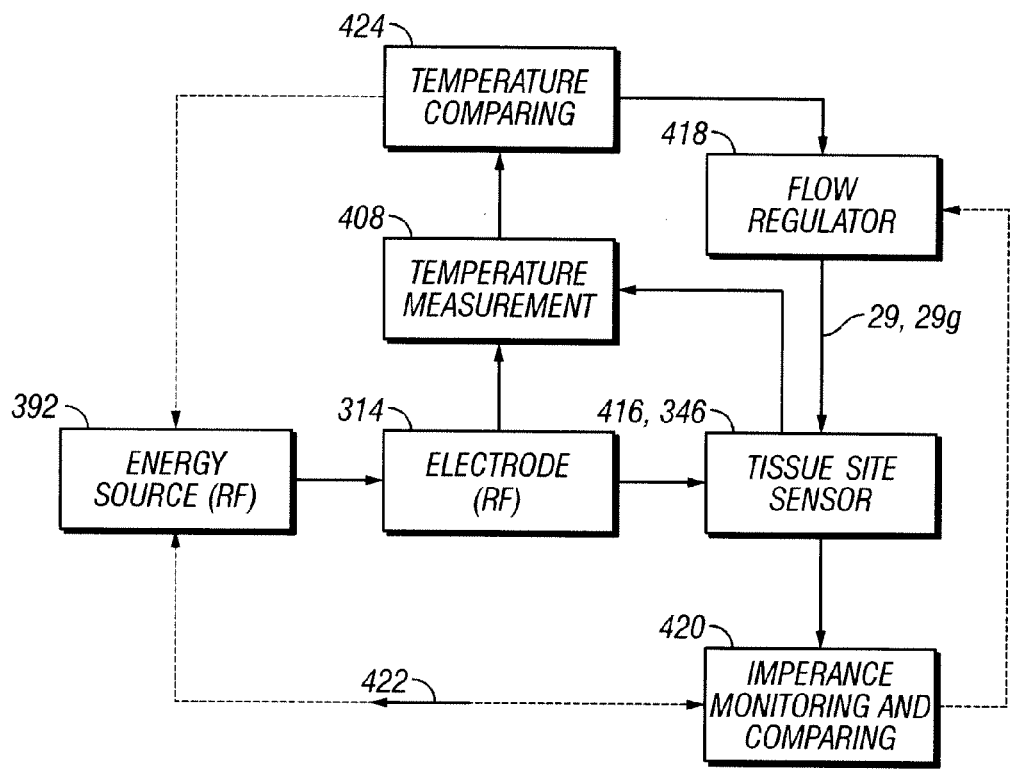
FIG. 74 illustrates the use of an apparatus of the present invention with a temperature and impedance feedback system.

FIG. 74 illustrates a block diagram of a temperature and impedance feedback system that can be used to control the delivery of energy to tissue site 416 by energy source 392 and the delivery of cooling solution 29 or gas 29g to electrode 314 and/or tissue site 416 by flow regulator 418. Energy is delivered to RF electrode 314 by energy source 392, and applied to tissue site 416. A monitor 420 ascertains tissue impedance, based on the energy delivered to tissue, and compares the measured impedance value to a set value. If the measured impedance exceeds the set value, a disabling signal 422 is transmitted to energy source 392, ceasing further delivery of energy to RF electrode 314. If the measured impedance is within acceptable limits, energy continues to be applied to the tissue.

The control of the flow of cooling solution 29 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the tissue temperature is too high, comparator 424 sends a signal to a flow regulator 418 (which can be integral to a pump 418) representing a need for an increased cooling solution flow rate. If the measured temperature has not exceeded the desired temperature, comparator 424 sends a signal to flow regulator 418 to maintain the cooling solution flow rate at its existing level.

The foregoing description of various embodiments of the invention has been presented for purposes of illustration and description. Various methods of the invention are applicable to variety of medical, dermatological and surgical methods including reconstructive and plastic surgery procedures and minimally invasive procedures. It is not intended to limit the invention to the precise forms disclosed. Many modifications, variations and different combinations of embodiments will be apparent to practitioners skilled in this art. Further, elements from one embodiment can be readily recombined with one or more elements from other embodiments.

What is claimed is:

1. An electro-surgical apparatus, comprising:
an electrode with a cutting edge; and
a housing coupled to the electrode and including a top with a top proximal section and a bottom with a bottom proximal section, the top proximal section having a geometry that facilitates creation of a skin flap with a substantially uniform thickness that includes a skin layer and an adjacent layer of subcutaneous tissue, the bottom proximal section having a geometry that preserves a plane of tissue that is positioned adjacent to the adjacent layer of subcutaneous tissue, the bottom proximal section having a most proximal point at "A", and the top proximal section having a most proximal point at "B" with A being more proximal than B, bottom proximal section defined by point A and a more distal point "C" with the electrode extending from point A to point B, the electrode forms a hypoteneus of a triangle defined by points A, B, and a point D that is positioned at a more proximal position than point B, bottom proximal section forming a hypotenuse of a triangle defined by points A, C and a point E with point E being more proximal than point C, a distance between points D and A being 1 mm to 2.5 cm, a distance between points D and B can being 0 mm to 1.5 cm, a distance between points A and E being 0 mm to 1.5 cm, and a distance between points E and C being 0 mm to 1.5 cm.

2. The apparatus of claim 1, wherein the housing includes a gap between the top proximal section and the bottom proximal section.

3. The apparatus of claim 1, wherein the housing includes a chamber that facilitates creation of the skin flap.

4. The apparatus of claim 1, further comprising:
an insulator coupled to at least a portion of the electrode.

* * * * *